US005879896A

United States Patent [19]
Hinuma et al.

[11] Patent Number: 5,879,896
[45] Date of Patent: Mar. 9, 1999

[54] METHOD OF SCREENING FOR INHIBITORS OF HUMAN THYROTROPIN RELEASING HORMONE (TRH) RECEPTOR

[75] Inventors: Shuji Hinuma; Masaki Hosoya, both of Tsukuba; Haruo Onda, Tsuchiura, all of Japan

[73] Assignee: Takeda Chemical Industries, Ltd., Osaka, Japan

[21] Appl. No.: 288,663

[22] Filed: Aug. 9, 1994

[30] Foreign Application Priority Data

| Aug. 10, 1993 | [JP] | Japan | 5-198309 |
| Nov. 16, 1993 | [JP] | Japan | 5-286986 |
| Dec. 22, 1993 | [JP] | Japan | 5-325215 |
| Mar. 16, 1994 | [JP] | Japan | 6-044497 |

[51] Int. Cl.$^6$ .................. G01N 33/53; G01N 33/566
[52] U.S. Cl. .................. 435/7.2; 435/7.1; 435/7.21; 435/69.1; 530/350; 536/23.5; 436/500
[58] Field of Search .................. 435/7.2, 7.1, 7.21, 435/69.1; 436/500; 530/350; 536/23.5

[56] References Cited

U.S. PATENT DOCUMENTS 5,288,621  2/1994  Gershengorn et al. ........... 435/69.4

FOREIGN PATENT DOCUMENTS

WO 92/10565  6/1992  WIPO.
WO 94/29447  12/1994  WIPO.

OTHER PUBLICATIONS

Dorland's Illustrated Medical Dictionary (1994) W. B. Saunder's Company, Philadelphia, pp. 1714–1715.
Le Dafniet, M. et al. (1985) Horm. Metabol. Res. 17:476–479.
Watson, S. et al. (1994) The G–Protein Linked Receptor Factsbook, Academic Press, San Diego, pp. 275–277, 297, 335–339.
Drummond, A. H. (1985) Biochem. Biophys. Res. Comm. 127:63–70.
De Marinis, L. et al. (1990) Acta Endocrinol. 122:433–449.
Endocrinology vol. 128 No. 2, 1991, pp. 1204–1206 Gershengorn M.C. et al. Regulation of Thyrotropin–Releasing Hormone Receptors in Cell Type Specific Comparison of Endogenous Pituitary Receptors and Receptors Transfected into Non–Pituitary Cells.
Ann New York Acad Sci vol. 553, May 8, 1989, pp. 147–175; Sharif. N.A. Quantitative Autoradiography of TRH Receptors in Discrete Brain Regions of Different Species.
Brain Research 563 vol, Jun. 1991, pp. 66–76 Najimi et al. Autoradiographic distribution of TRH binding sites in the Human Hypothalamus.
V. Matre et al., *Biochemical and Biophysical Research Communications*, 195(1): 179–185 (1993).
P. Pena et al., *The Journal of Biological Chemistry*, 267(36): 25703–25708 (1992).
Pamphlet of Medical Research Council (MRC) "Human TRH Receptor".
M. Yamada et al., *Biochemical and Biophysical Research Communications*, 195(2): 737–745 (1993).
R. Straub et al., *Proc. Natl. Acad. Sci. USA*, 87: 9514–9518 (1990).
P. de la Peña et al., *Biochemical Journal*, 284: 891–899 (1992).

*Primary Examiner*—Lila Feisee
*Assistant Examiner*—Michael D. Pak
*Attorney, Agent, or Firm*—David G. Conlin; David S. Resnick; Dike, Bronstein, Roberts & Cushman, LLP

[57] ABSTRACT

A human receptor protein capable of binding TRH, a DNA coding for said protein, use of the proetin and DNA, a method for preparing said protein, and antibodies to the protein are described.

The human TRH receptor protein and the DNA coding for the protein of the present invention are useful as (1) a diagnostic composition for neuropathy (particularly, dementia), (2) a pharmaceutical composition for neuropathy and (3) a material used for screening a TRH receptor agonist or antagonist.

19 Claims, 20 Drawing Sheets

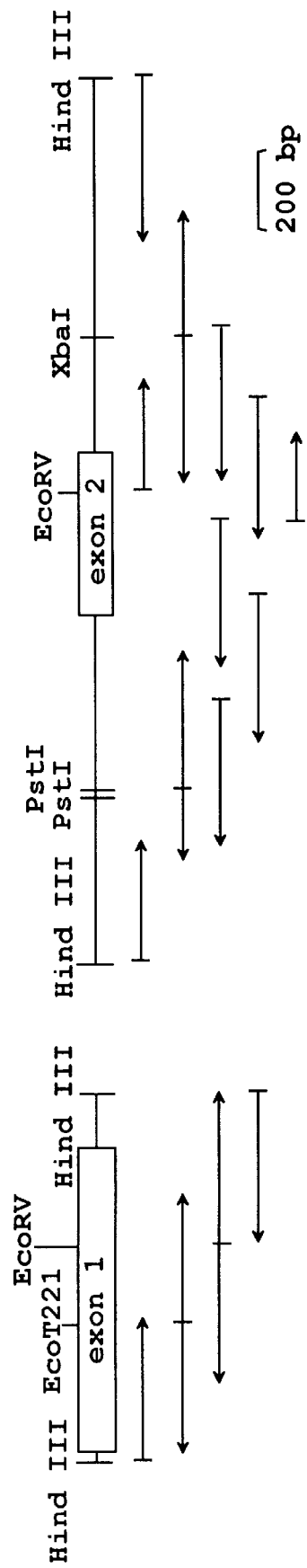

|     | 10         | 20         | 30         | 40         | 50         | 60    |
AAGCTTCTAAAG<u>ATG</u>GAAAACGAGACAGTCAGTGAACTGAACCAAACACAGCTTCAGCCA
HindIII

|     | 70         | 80         | 90         | 100        | 110        | 120.  |
CGAGCAGTGGTGGCCTTAGAATACCAGGTGGTCACCATCTTACTTGTACTCATTATTTGT

|     | 130        | 140        | 150        | 160        | 170        | 180   |
GGCCTGGGCATTGTAGGCAACATCATGGTAGTCCTGGTTGTCATGAGAACCAAGCACATG

|     | 190        | 200        | 210        | 220        | 230        | 240   |
AGGACCCCCACAAACTGCTACCTGGTGAGCCTGGCAGTAGCTGATCTCATGGTCTTGGTG

|     | 250        | 260        | 270        | 280        | 290        | 300   |
GCCGCAGGCCTCCCCAACATAACAGACAGTATCTACGGTTCCTGGGTCTATGGCTATGTT

|     | 310        | 320        | 330        | 340        | 350        | 360   |
GGATGCCTCTGCATTACTTACCTCCAGTATTTGGGAATTAATGCATCCTCTTGTTCAATA

|     | 370        | 380        | 390        | 400        | 410        | 420   |
ACAGCCTTTACCATTGAGAGGTACATAGCAATCTGTCACCCCATCAAAGCCCAGTTTCTC

|     | 430        | 440        | 450        | 460        | 470        | 480   |
TGCACATTTTCCAGAGCCAAAAAGATTATCATCTTTGTCTGGGCTTTCACATCTCTTTAC

|     | 490        | 500        | 510        | 520        | 530        | 540   |
TGTATGCTCTGGTTCTTCTTGCTGGATCTCAATATTAGCACCTACAAAGATGCTATTGTG

|     | 550        | 560        | 570        | 580        | 590        | 600   |
ATATCCTGTGGCTACAAGATCTCCAGGAATTACTACTCACCTATTTACCTAATGGACTTT

|     | 610        | 620        | 630        | 640        | 650        | 660   |
GGTGTCTTTTATGTTGTGCCAATGATCCTGGCTACCGTCCTCTATGGATTCATAGCTAGA

|     | 670        | 680        | 690        | 700        | 710        | 720   |
ATCCTTTTCTTAAATCCCATTCCTTCAGATCCTAAAGAAAACTCTAAGACATGGAAAAAT

|     | 730        | 740        | 750        | 760        | 770        | 780   |
GATTCAACCCATCAGAACACAAATCTGAATGTAAATACCTCTAATAGATGTTTCAACAGC

|     | 790        | 800        | 810        | 820        | 830        | 840   |
ACAGTATCTTCAAGGAAGCAG<u>GTAAGC</u>AAAACTGAAACTCCAAGTCAATAGAGGAAATGT

|     | 850        | 860        | 870        | 880        | 890        | 900   |
GGGATAGAGTTCCTTGGAGATGGGAAACAACTTTTCCCTGTTTAGCTGATGGCGAAACCA

|     | 910        | 920        | 930        |
AAATACAATCATGCAAATGTTTCACAGTGTAAGCTT
HindIII

FIG. 2

```
AAGCTT--------------(about 900 bp)------------------------
HindIII
        10        20        30        40        50        60
GTTTGTACAGCATTTCTCTCTATTTCTCCCTAGGTCACCAAGATGCTGGCAGTGGTTGTA 70        80        90       100       110       120
ATTCTGTTTGCCCTTTTATGGATGCCCTACAGGACTCTAGTGGTTGTCAACTCATTTCTC 130       140       150       160       170       180
TCCAGTCCTTTCCAAGAAAATTGGTTTTTGCTCTTTTGCAGAATTTGCATTTATCTCAAC 190       200       210       220       230       240
AGTGCCATCAACCCGGTGATTTACAATCTCATGTCCCAGAAATTCCGTGCAGCCTTCAGA 250       260       270       280       290       300
AAGCTCTGCAACTGCAAGCAGAAGCCAACAGAGAAACCTGCTAACTACAGTGTGGCCCTA 310       320       330       340       350       360
AATTACAGCGTCATCAAGGAGTCAGACCATTTCAGCACAGAGCTTGATGATATCACTGTC 370       380       390       400       410       420
ACTGACACTTACCTGTCTGCCACAAAAGTGTCTTTTGATGACACCTGCTTGGCTTCTGAG 430       440       450       460       470       480
GTATCCTTTAGCCAAAGTTGATTCATGAATTAGAAGAAAATGGATGACAAAGAAAATGAG -----------------------(about 1000 bp)------------------AAGCTT
                                                        HindIII
```

```
   1 AAGCTTCTAAAGATGGAAAACGAGACAGTCAGTGAACTGAACCAAACACAGCTTCAGCCA    60
     .........MetGluAsnGluThrValSerGluLeuAsnGlnThrGlnLeuGlnPro      16

61 CGAGCAGTGGTGGCCTTAGAATACCAGGTGGTCACCATCTTACTTGTACTCATTATTGT   120
  17 ArgAlaValValAlaLeuGluTyrGlnValValThrIleLeuLeuValLeuIleIleCys    36

121 GGCCTGGGCATTGTAGGCAACATCATGGTAGTCCTGGTTGTCATGAGAACCAAGCACATG   180
  37 GlyLeuGlyIleValGlyAsnIleMetValValLeuValValMetArgThrLysHisMet    56

181 AGGACCCCCACAAACTGCTACTGGTGAGCCTGGAGCCTGATCTCATGGTCTTGGTG   240
  57 ArgThrProThrAsnCysTyrTrpLeuValSerLeuAlaAlaAspLeuMetValLeuVal    76

241 GCCGCAGGCCTCCCCAACAGACAGTATCTACGGTTCCTGGGTCTATGGCTATGTT   300
  77 AlaAlaGlyLeuProAsnIleThrAspSerIleTyrGlySerTrpValTyrGlyTyrVal    96

301 GGATGCCTCTGCATTACTTACCTCCAGTATTTGGGAATTAATGCATCCTCTGTTCAATA   360
  97 GlyCysLeuCysIleThrTyrLeuGlnTyrLeuGlyIleAsnAlaSerSerCysSerIle   116

361 ACAGCCTTTACCATTGAGAGGTACATTGCTATCTGTCACCCATCCAAGCCCAGTTCTC   420
 117 ThrAlaPheThrIleGluArgTyrIleAlaIleCysHisProIleLysAlaGlnPheLeu   136

421 TGCACATTTTCCAGAGCCAAAAGATCTTCTTGCTTTCACATCTCTTTAC   480
 137 CysThrPheSerArgAlaLysLysIleLeuLeuValTrpAlaPheThrSerLeuTyr   156

481 TGTATGCTCTGGTTCTTCTTGCTGGATCTCAATATTAGCACTCACCTATTACCTAATGGACTTT   540
 157 CysMetLeuTrpPhePheLeuLeuAspLeuAsnIleSerThrTyrLysAspAlaIleVal   176

541 ATATCCTGTGGCTACAAGATCTCCAGGAATTACTACTACCTATTCTCCTATCTAATGGACTTT   600
 177 IleSerCysGlyTyrLysIleSerArgAsnTyrTyrSerProIleTyrLeuMetAspPhe   196

601 GGTGTCTTTATGTGTGCCAATGATCCTGGCTACCGTCCTCTATGGATTCATAGCTAGA   660
 197 GlyValPheTyrValValProMetIleLeuAlaThrValLeuTyrGlyPheIleAlaArg   216

661 ATCCTTTTCTTAAATCCCATTCCTCAGATCCTAAAGAAAACTCTAAGACATGGAAAAAT   720
 217 IleLeuPheLeuAsnProIleProSerAspProLysGluAsnSerLysTrpLysAsn   236
```

FIG. 4A

```
721  GATTCAACCCATCAGAACACAAATCTGAATGTAAATACCTCTAATAGATGTTTCAACAGC   780
237  AspSerThrHisGlnAsnThrLysAsnValAsnThrSerAsnArgCysPheAsnSer      256
                          ▼INTRON

781  ACAGTATCTTCAAGGAAGCAGGTCACCAAGATGCTGGCAGTGGTTGTAATTCTGTTTGCC   840
257  ThrValSerArgLysSerArgLysGlnValThrLysMetLeuAlaValValIleLeuPheAla   276

841  CTTTTATGGATGCCCTACAGGACTCTAGTGGTTGTCAACTCATTCTCTCCAGTCCTTC    900
277  LeuLeuTrpMetProTyrArgThrLeuValValValAlaAsnSerPheLeuSerSerProPhe   296

901  CAAGAAAATTGGTTTTTGCTCTTTTGCAGAATTTGCATTTATCTCAACAGTGCCATCAAC   960
297  GlnGluAsnTrpPheLeuPheCysArgIleCysIleTyrLeuAsnSerAlaIleAsn     316

961  CCGGTGATTTACAATCTCATGTCCCAGAAATTCCGTGCAGCCTTCAGAAAGCTCTGCAAC  1020
317  ProValIleTyrAsnLeuMetSerGlnLysPheArgAlaAlaPheArgLysLeuCysAsn  336

1021 TGCAAGCAGAAGCCAACAGAGAAACCTGCTAACTACAGTGGCCTAAATTACAGCGTC    1080
337  CysLysGlnLysProThrGluLysProAlaAsnTyrSerValAlaLeuAsnTyrSerVal  356

1081 ATCAAGGAGTCAGACCATTTCAGCTTCGATGATATCACTGTCACTGACACTTAC       1140
357  IleLysGluSerAspHisPheSerPheAspAspIleThrValThrAspThrTyr       376

1141 CTGTCTGCCACAAAGTGTCTTTTGATGACACCTGCTTGCCTTCTGAGGTATCCTTTAGC  1200
377  LeuSerAlaThrLysCysLeuLeuMetThrProAlaCysLeuLeuArgTyrProLeuSer  396

1201 CAAGTTGATTCATGAATTAGAAGAAAA                                  1228
397  GlnSer *                                                     398
```

FIG. 4B

| NO | TARGET FILE | KEY | TARGET | OVERLAP | MATCH | PERCENTAGE |
|---|---|---|---|---|---|---|
| 1 | RTRHR. AMI | 1 | 1 | 399 | 374 | 93.73% |

```
            10        20        30        40        50        60        70
h   MENETVSELNQTQLQPRAVVALEYQVVTILLVLIICGLGIVGNIMVLVVMRTKHMRTPTNCYLVSLAVA
    ********** * ********************** *** ****************** *******
r   MENETVSELNQTDLPPQVAVALEYQVVTILLVVICGLGIVGNIMVLVVMRTKHMRTATNCYLVSLAVA
            10        20        30        40        50        60        70

80        90        100       110       120       130       140
h   DLMVLVAAGLPNITDSIYGSWVYGYVGCLCITYLQYLGINASSCSITAFTIERYIAICHPIKAQFLCTFS
    ****************************************************************
r   DLMVLVAAGLPNITDSIYGSWVYGYVGCLCITYLQYLGINASSCSITAFTIERYIAICHPIKAQFLCTFS
            80        90        100       110       120       130       140

150       160       170       180       190       200       210
h   RAKKIIIFVWAFTSLYCMLWFFLLDLNISTYKDAIVISCGYKISRNYYSPIYLMDFGVFYVVPMILATVL
    *********** ************************** *** ************************
r   RAKKIIIFVWAFTSIYCMLWFFLLDLNISTYKDAIVISCGYKISRNYYSFIYLMDFGVFYVMPMILATVL
            150       160       170       180       190       200       210

220       230       240       250       260       270       280
h   YGFIARILFLNPIPSDPKENSKTWKNDSTHQNTNLNVNTSNRCFNSTVSSRKQYTKMLAVVVILFALLWM
    ************************** *  *   **************** ****************
r   YGFIARILFLNPIPSDPKENSKTWKNDSTHQNKMNLNTTNRCFNSTVSSRKQVTKMLAVVVILFALLWM
            220       230       240       250       260       270       280

290       300       310       320       330       340       350
h   PYRTLVVVNSFLSSPFQENWFLLFCRICIYLNSAINPVIYNLMSQKFRAAFRKLCNCKQKPTEKPANYSV
    *********** ********************************** ********* ** **  ****
r   PYRTLVVNSKLSSPFQENWFLLFCRICIYLNSAINPVIYNLMSQKFRAAFRKLCNGKQKPTEKAANYSV
            290       300       310       320       330       340       350

360       370       380       390
h   ALNYSVIKESDHFSTELDDITVTDTYLSAATKVSFDDTCLASEVSFSQS*      -C
    ***************** ********  ****************
r   ALNYSVIKESDRFSTELDDITVTDTYVSTTKVSFDDTCLASEKNGPSSC      -C
            360       370       380       390
```

FIG. 5

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 398 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Met Glu Asn Glu Thr Val Ser Glu Leu Asn Gln Thr Gln Leu Gln Pro
1               5                   10                  15

Arg Ala Val Val Ala Leu Glu Tyr Gln Val Val Thr Ile Leu Leu Val
            20                  25                  30

Leu Ile Ile Cys Gly Leu Gly Ile Val Gly Asn Ile Met Val Val Leu
        35                  40                  45

Val Val Met Arg Thr Lys His Met Arg Thr Pro Thr Asn Cys Tyr Leu
    50                  55                  60

Val Ser Leu Ala Val Ala Asp Leu Met Val Leu Val Ala Ala Gly Leu
```

|   |   |   |   | 65 |   |   |   |   | 70 |   |   |   |   | 75 |   |   |   |   | 80 |
|---|---|---|---|----|---|---|---|---|----|---|---|---|---|----|---|---|---|---|----|
| Pro | Asn | Ile | Thr | Asp 85 | Ser | Ile | Tyr | Gly | Ser 90 | Trp | Val | Tyr | Gly | Tyr 95 | Val |
| Gly | Cys | Leu | Cys 100 | Ile | Thr | Tyr | Leu | Gln 105 | Tyr | Leu | Gly | Ile | Asn 110 | Ala | Ser |
| Ser | Cys | Ser 115 | Ile | Thr | Ala | Phe | Thr 120 | Ile | Glu | Arg | Tyr | Ile 125 | Ala | Ile | Cys |
| His | Pro 130 | Ile | Lys | Ala | Gln | Phe 135 | Leu | Cys | Thr | Phe | Ser 140 | Arg | Ala | Lys | Lys |
| Ile 145 | Ile | Ile | Phe | Val | Trp 150 | Ala | Phe | Thr | Ser | Leu 155 | Tyr | Cys | Met | Leu | Trp 160 |
| Phe | Phe | Leu | Leu | Asp 165 | Leu | Asn | Ile | Ser | Thr 170 | Tyr | Lys | Asp | Ala | Ile 175 | Val |
| Ile | Ser | Cys | Gly 180 | Tyr | Lys | Ile | Ser | Arg 185 | Asn | Tyr | Tyr | Ser | Pro 190 | Ile | Tyr |
| Leu | Met | Asp 195 | Phe | Gly | Val | Phe | Tyr 200 | Val | Val | Pro | Met | Ile 205 | Leu | Ala | Thr |
| Val | Leu 210 | Tyr | Gly | Phe | Ile | Ala 215 | Arg | Ile | Leu | Phe | Leu 220 | Asn | Pro | Ile | Pro |
| Ser 225 | Asp | Pro | Lys | Glu | Asn 230 | Ser | Lys | Thr | Trp | Lys 235 | Asn | Asp | Ser | Thr | His 240 |
| Gln | Asn | Thr | Asn | Leu 245 | Asn | Val | Asn | Thr | Ser 250 | Asn | Arg | Cys | Phe | Asn 255 | Ser |
| Thr | Val | Ser | Ser 260 | Arg | Lys | Gln | Val | Thr 265 | Lys | Met | Leu | Ala | Val 270 | Val | Val |
| Ile | Leu | Phe 275 | Ala | Leu | Leu | Trp | Met 280 | Pro | Tyr | Arg | Thr | Leu 285 | Val | Val | Val |
| Asn | Ser 290 | Phe | Leu | Ser | Ser | Pro 295 | Phe | Gln | Glu | Asn | Trp 300 | Phe | Leu | Leu | Phe |
| Cys 305 | Arg | Ile | Cys | Ile | Tyr 310 | Leu | Asn | Ser | Ala | Ile 315 | Asn | Pro | Val | Ile | Tyr 320 |
| Asn | Leu | Met | Ser | Gln 325 | Lys | Phe | Arg | Ala | Ala 330 | Phe | Arg | Lys | Leu | Cys 335 | Asn |
| Cys | Lys | Gln | Lys 340 | Pro | Thr | Glu | Lys | Pro 345 | Ala | Asn | Tyr | Ser | Val 350 | Ala | Leu |
| Asn | Tyr | Ser 355 | Val | Ile | Lys | Glu | Ser 360 | Asp | His | Phe | Ser | Thr 365 | Glu | Leu | Asp |
| Asp | Ile | Thr 370 | Val | Thr | Asp | Thr | Tyr 375 | Leu | Ser | Ala | Thr | Lys 380 | Val | Ser | Phe |
| Asp 385 | Asp | Thr | Cys | Leu | Ala 390 | Ser | Glu | Val | Ser | Phe 395 | Ser | Gln | Ser |   |   |

( 2 ) INFORMATION FOR SEQ ID NO:2:

( i ) SEQUENCE CHARACTERISTICS:
        ( A ) LENGTH: 1194 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

```
ATGGAAAACG AGACAGTCAG TGAACTGAAC CAAACACAGC TTCAGCCACG AGCAGTGGTG        60
GCCTTAGAAT ACCAGGTGGT CACCATCTTA CTTGTACTCA TTATTTGTGG CCTGGGCATT       120
GTAGGCAACA TCATGGTAGT CCTGGTTGTC ATGAGAACCA AGCACATGAG GACCCCCACA       180
```

| | | | | | |
|---|---|---|---|---|---|
| AACTGCTACC | TGGTGAGCCT | GGCAGTAGCT | GATCTCATGG | TCTTGGTGGC | CGCAGGCCTC | 240 |
| CCCAACATAA | CAGACAGTAT | CTACGGTTCC | TGGGTCTATG | CTATGTTGG | ATGCCTCTGC | 300 |
| ATTACTTACC | TCCAGTATTT | GGGAATTAAT | GCATCCTCTT | GTTCAATAAC | AGCCTTTACC | 360 |
| ATTGAGAGGT | ACATAGCAAT | CTGTCACCCC | ATCAAAGCCC | AGTTTCTCTG | CACATTTTCC | 420 |
| AGAGCCAAAA | AGATTATCAT | CTTTGTCTGG | GCTTTCACAT | CTCTTTACTG | TATGCTCTGG | 480 |
| TTCTTCTTGC | TGGATCTCAA | TATTAGCACC | TACAAGATG | CTATTGTGAT | ATCCTGTGGC | 540 |
| TACAAGATCT | CCAGGAATTA | CTACTCACCT | ATTTACCTAA | TGGACTTTGG | TGTCTTTTAT | 600 |
| GTTGTGCCAA | TGATCCTGGC | TACCGTCCTC | TATGGATTCA | TAGCTAGAAT | CCTTTTCTTA | 660 |
| AATCCCATTC | CTTCAGATCC | TAAAGAAAAC | TCTAAGACAT | GGAAAAATGA | TTCAACCCAT | 720 |
| CAGAACACAA | ATCTGAATGT | AAATACCTCT | AATAGATGTT | TCAACAGCAC | AGTATCTTCA | 780 |
| AGGAAGCAGG | TCACCAAGAT | GCTGGCAGTG | GTTGTAATTC | TGTTTGCCCT | TTTATGGATG | 840 |
| CCCTACAGGA | CTCTAGTGGT | TGTCAACTCA | TTTCTCTCCA | GTCCTTTCCA | AGAAAATTGG | 900 |
| TTTTTGCTCT | TTTGCAGAAT | TTGCATTTAT | CTCAACAGTG | CCATCAACCC | GGTGATTTAC | 960 |
| AATCTCATGT | CCCAGAAATT | CCGTGCAGCC | TTCAGAAAGC | TCTGCAACTG | CAAGCAGAAG | 1020 |
| CCAACAGAGA | AACCTGCTAA | CTACAGTGTG | GCCCTAAATT | ACAGCGTCAT | CAAGGAGTCA | 1080 |
| GACCATTTCA | GCACAGAGCT | TGATGATATC | ACTGTCACTG | ACACTTACCT | GTCTGCCACA | 1140 |
| AAAGTGTCTT | TTGATGACAC | CTGCTTGGCT | TCTGAGGTAT | CCTTTAGCCA | AAGT | 1194 |

(2) INFORMATION FOR SEQ ID NO:3:

(i) SEQUENCE CHARACTERISTICS:
        (A) LENGTH: 1228 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

| | | | | | |
|---|---|---|---|---|---|
| AAGCTTCTAA | AGATGGAAAA | CGAGACAGTC | AGTGAACTGA | ACCAAACACA | GCTTCAGCCA | 60 |
| CGAGCAGTGG | TGGCCTTAGA | ATACCAGGTG | GTCACCATCT | TACTTGTACT | CATTATTTGT | 120 |
| GGCCTGGGCA | TTGTAGGCAA | CATCATGGTA | GTCCTGGTTG | TCATGAGAAC | CAAGCACATG | 180 |
| AGGACCCCCA | CAAACTGCTA | CCTGGTGAGC | CTGGCAGTAG | CTGATCTCAT | GGTCTTGGTG | 240 |
| GCCGCAGGCC | TCCCCAACAT | AACAGACAGT | ATCTACGGTT | CCTGGGTCTA | TGGCTATGTT | 300 |
| GGATGCCTCT | GCATTACTTA | CCTCCAGTAT | TTGGGAATTA | ATGCATCCTC | TTGTTCAATA | 360 |
| ACAGCCTTTA | CCATTGAGAG | GTACATAGCA | ATCTGTCACC | CCATCAAAGC | CCAGTTTCTC | 420 |
| TGCACATTTT | CCAGAGCCAA | AAAGATTATC | ATCTTTGTCT | GGGCTTTCAC | ATCTCTTTAC | 480 |
| TGTATGCTCT | GGTTCTTCTT | GCTGGATCTC | AATATTAGCA | CCTACAAAGA | TGCTATTGTG | 540 |
| ATATCCTGTG | GCTACAAGAT | CTCCAGGAAT | TACTACTCAC | CTATTTACCT | AATGGACTTT | 600 |
| GGTGTCTTTT | ATGTTGTGCC | AATGATCCTG | GCTACCGTCC | TCTATGGATT | CATAGCTAGA | 660 |
| ATCCTTTTCT | TAAATCCCAT | TCCTTCAGAT | CCTAAAGAAA | ACTCTAAGAC | ATGGAAAAAT | 720 |
| GATTCAACCC | ATCAGAACAC | AAATCTGAAT | GTAAATACCT | CTAATAGATG | TTTCAACAGC | 780 |
| ACAGTATCTT | CAAGGAAGCA | GGTCACCAAG | ATGCTGGCAG | TGGTTGTAAT | TCTGTTTGCC | 840 |
| CTTTTATGGA | TGCCCTACAG | GACTCTAGTG | GTTGTCAACT | CATTTCTCTC | CAGTCCTTTC | 900 |
| CAAGAAAATT | GGTTTTTGCT | CTTTTGCAGA | ATTTGCATTT | ATCTCAACAG | TGCCATCAAC | 960 |

| | | | | | |
|---|---|---|---|---|---|
| CCGGTGATTT | ACAATCTCAT | GTCCCAGAAA | TTCCGTGCAG | CCTTCAGAAA | GCTCTGCAAC 1020 |
| TGCAAGCAGA | AGCCAACAGA | GAAACCTGCT | AACTACAGTG | TGGCCCTAAA | TTACAGCGTC 1080 |
| ATCAAGGAGT | CAGACCATTT | CAGCACAGAG | CTTGATGATA | TCACTGTCAC | TGACACTTAC 1140 |
| CTGTCTGCCA | CAAAAGTGTC | TTTTGATGAC | ACCTGCTTGG | CTTCTGAGGT | ATCCTTTAGC 1200 |
| CAAAGTTGAT | TCATGAATTA | GAAGAAAA | | | 1228 |

( 2 ) INFORMATION FOR SEQ ID NO:4:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: Other nucleic acid, synthetic DNA ( x i ) SEQUENCE DESCRIPTION: SEQ ID NO:4:

TCTAAAGCTT GAAGATGGAG AATGAAACCG TCAGTGA        37

( 2 ) INFORMATION FOR SEQ ID NO:5:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: Other nucleic acid, Synthetic DNA ( x i ) SEQUENCE DESCRIPTION: SEQ ID NO:5:

GTCTTCTAGA AGTTCATATT TTCTCCTGTT TGGCAGT        37

( 2 ) INFORMATION FOR SEQ ID NO:6:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: Other nucleic acid, Synthetic DNA ( x i ) SEQUENCE DESCRIPTION: SEQ ID NO:6:

GCGCAAGCTT CTAAAGATGG AAAACGAG        28

( 2 ) INFORMATION FOR SEQ ID NO:7:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: Other nucleic acid, Synthetic DNA ( x i ) SEQUENCE DESCRIPTION: SEQ ID NO:7:

TCTAATTCTA GAATCAACTT TGGCTAAA        28

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid, Synthetic DNA ( x i ) SEQUENCE DESCRIPTION: SEQ ID NO:8:

CACCGGGTTG ATGGCAC 17

( 2 ) INFORMATION FOR SEQ ID NO:9:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: Other nucleic acid, Synthetic DNA ( x i ) SEQUENCE DESCRIPTION: SEQ ID NO:9:

TCAAGGAAGC AG 12

( 2 ) INFORMATION FOR SEQ ID NO:10:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: Other nucleic acid, Synthetic DNA ( x i ) SEQUENCE DESCRIPTION: SEQ ID NO:10:

GTGACCTGCT TCC 13

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: Other nucleic acid, Synthetic DNA ( x i ) SEQUENCE DESCRIPTION: SEQ ID NO:11:

GTCGACGAAT TCATCGATAC TAGTGCTAGC 30

( 2 ) INFORMATION FOR SEQ ID NO:12:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: Other nucleic acid, Synthetic DNA ( x i ) SEQUENCE DESCRIPTION: SEQ ID NO:12:

TCGAGCTAGC ACTAGTATCG ATGAATTCGT CGAC 34

( 2 ) INFORMATION FOR SEQ ID NO:13:

( i ) SEQUENCE CHARACTERISTICS:
        ( A ) LENGTH: 936 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

AAGCTTCTAA AGATGGAAAA CGAGACAGTC AGTGAACTGA ACCAAACACA GCTTCAGCCA 60

CGAGCAGTGG TGGCCTTAGA ATACCAGGTG GTCACCATCT TACTTGTACT CATTATTTGT 120

-continued

| | | | | | |
|---|---|---|---|---|---|
| GGCCTGGGCA | TTGTAGGCAA | CATCATGGTA | GTCCTGGTTG | TCATGAGAAC | CAAGCACATG | 180 |
| AGGACCCCCA | CAAACTGCTA | CCTGGTGAGC | CTGGCAGTAG | CTGATCTCAT | GGTCTTGGTG | 240 |
| GCCGCAGGCC | TCCCCAACAT | AACAGACAGT | ATCTACGGTT | CCTGGGTCTA | TGGCTATGTT | 300 |
| GGATGCCTCT | GCATTACTTA | CCTCCAGTAT | TTGGGAATTA | ATGCATCCTC | TTGTTCAATA | 360 |
| ACAGCCTTTA | CCATTGAGAG | GTACATAGCA | ATCTGTCACC | CCATCAAAGC | CCAGTTTCTC | 420 |
| TGCACATTTT | CCAGAGCCAA | AAAGATTATC | ATCTTTGTCT | GGGCTTTCAC | ATCTCTTTAC | 480 |
| TGTATGCTCT | GGTTCTTCTT | GCTGGATCTC | AATATTAGCA | CCTACAAAGA | TGCTATTGTG | 540 |
| ATATCCTGTG | GCTACAAGAT | CTCCAGGAAT | TACTACTCAC | CTATTTACCT | AATGGACTTT | 600 |
| GGTGTCTTTT | ATGTTGTGCC | AATGATCCTG | GCTACCGTCC | TCTATGGATT | CATAGCTAGA | 660 |
| ATCCTTTTCT | TAAATCCCAT | TCCTTCAGAT | CCTAAGAAA | ACTCTAAGAC | ATGGAAAAAT | 720 |
| GATTCAACCC | ATCAGAACAC | AAATCTGAAT | GTAAATACCT | CTAATAGATG | TTTCAACAGC | 780 |
| ACAGTATCTT | CAAGGAAGCA | GGTAAGCAAA | ACTGAAACTC | CAAGTCAATA | GAGGAAATGT | 840 |
| GGGATAGAGT | TCCTTGGAGA | TGGGAAACAA | CTTTTCCCTG | TTTAGCTGAT | GGCGAAACCA | 900 |
| AAATACAATC | ATGCAAATGT | TTCACAGTGT | AAGCTT | | | 936 |

( 2 ) INFORMATION FOR SEQ ID NO:14:

( i ) SEQUENCE CHARACTERISTICS:
( A ) LENGTH: 480 base pairs
( B ) TYPE: nucleic acid
( C ) STRANDEDNESS: single
( D ) TOPOLOGY: linear ( x i ) SEQUENCE DESCRIPTION: SEQ ID NO:14:

| | | | | | |
|---|---|---|---|---|---|
| GTTTGTACAG | CATTTCTCTC | TATTTCTCCC | TAGGTCACCA | AGATGCTGGC | AGTGGTTGTA | 60 |
| ATTCTGTTTG | CCCTTTTATG | GATGCCCTAC | AGGACTCTAG | TGGTTGTCAA | CTCATTTCTC | 120 |
| TCCAGTCCTT | TCCAAGAAAA | TTGGTTTTTG | CTCTTTTGCA | GAATTTGCAT | TTATCTCAAC | 180 |
| AGTGCCATCA | ACCGGTGAT | TTACAATCTC | ATGTCCCAGA | AATTCCGTGC | AGCCTTCAGA | 240 |
| AAGCTCTGCA | ACTGCAAGCA | GAAGCCAACA | GAGAAACCTG | CTAACTACAG | TGTGGCCCTA | 300 |
| AATTACAGCG | TCATCAAGGA | GTCAGACCAT | TCAGCACAG | AGCTTGATGA | TATCACTGTC | 360 |
| ACTGACACTT | ACCTGTCTGC | CACAAAAGTG | TCTTTTGATG | ACACCTGCTT | GGCTTCTGAG | 420 |
| GTATCCTTTA | GCCAAAGTTG | ATTCATGAAT | TAGAAGAAAA | TGGATGACAA | AGAAAATGAG | 480 |

( 2 ) INFORMATION FOR SEQ ID NO:15:

( i ) SEQUENCE CHARACTERISTICS:
( A ) LENGTH: 398 amino acids
( B ) TYPE: amino acid
( C ) STRANDEDNESS: single
( D ) TOPOLOGY: linear ( x i ) SEQUENCE DESCRIPTION: SEQ ID NO:15:

| Met | Glu | Asn | Glu | Thr | Val | Ser | Glu | Leu | Asn | Gln | Thr | Asp | Leu | Pro | Pro |
|---|---|---|---|---|---|---|---|---|---|---|---|---|---|---|---|
| 1 | | | | 5 | | | | | 10 | | | | | 15 | |

| Gln | Val | Ala | Val | Ala | Leu | Glu | Tyr | Gln | Val | Val | Thr | Ile | Leu | Leu | Val |
|---|---|---|---|---|---|---|---|---|---|---|---|---|---|---|---|
| | | | 20 | | | | | 25 | | | | 30 | | | |

| Val | Val | Ile | Cys | Gly | Leu | Gly | Ile | Val | Gly | Asn | Ile | Met | Val | Val | Leu |
|---|---|---|---|---|---|---|---|---|---|---|---|---|---|---|---|
| | | 35 | | | | | 40 | | | | | 45 | | | |

| Val | Val | Met | Arg | Thr | Lys | His | Met | Arg | Thr | Ala | Thr | Asn | Cys | Tyr | Leu |
|---|---|---|---|---|---|---|---|---|---|---|---|---|---|---|---|
| | 50 | | | | | 55 | | | | | 60 | | | | |

| Val | Ser | Leu | Ala | Val | Ala | Asp | Leu | Met | Val | Leu | Val | Ala | Ala | Gly | Leu |
|---|---|---|---|---|---|---|---|---|---|---|---|---|---|---|---|
| 65 | | | | | 70 | | | | | 75 | | | | | 80 |

-continued

```
Pro  Asn  Ile  Thr  Asp  Ser  Ile  Tyr  Gly  Ser  Trp  Val  Tyr  Gly  Tyr  Val
                    85                           90                      95
Gly  Cys  Leu  Cys  Ile  Thr  Tyr  Leu  Gln  Tyr  Leu  Gly  Ile  Asn  Ala  Ser
               100                 105                      110
Ser  Cys  Ser  Ile  Thr  Ala  Phe  Thr  Ile  Glu  Arg  Tyr  Ile  Ala  Cys  His
          115                      120                      125
Pro  Ile  Lys  Ala  Gln  Phe  Leu  Cys  Thr  Phe  Ser  Arg  Ala  Lys  Lys  Ile
     130                      135                 140
Ile  Ile  Phe  Val  Trp  Ala  Phe  Thr  Ser  Ile  Tyr  Cys  Met  Leu  Trp  Phe
145                      150                      155                      160
Phe  Leu  Leu  Asp  Leu  Asn  Ile  Ser  Thr  Tyr  Lys  Asp  Ala  Ile  Val  Ile
                    165                      170                      175
Ser  Cys  Gly  Tyr  Lys  Ile  Ser  Arg  Asn  Tyr  Tyr  Ser  Pro  Ile  Tyr  Leu
               180                 185                      190
Met  Asp  Phe  Gly  Val  Phe  Tyr  Val  Met  Pro  Met  Ile  Leu  Ala  Thr  Val
          195                 200                      205
Leu  Tyr  Gly  Phe  Ile  Ala  Arg  Ile  Leu  Phe  Leu  Asn  Pro  Ile  Pro  Ser
     210                      215                 220
Asp  Pro  Lys  Glu  Asn  Ser  Lys  Thr  Trp  Lys  Asn  Asp  Ser  Thr  His  Gln
225                      230                 235                           240
Asn  Lys  Asn  Met  Asn  Leu  Asn  Thr  Thr  Asn  Arg  Cys  Phe  Asn  Ser  Thr
                    245                      250                      255
Val  Ser  Ser  Arg  Lys  Gln  Val  Thr  Lys  Met  Leu  Ala  Val  Val  Val  Ile
               260                      265                 270
Leu  Phe  Ala  Leu  Leu  Trp  Met  Pro  Tyr  Arg  Thr  Leu  Val  Val  Val  Asn
          275                 280                      285
Ser  Lys  Leu  Ser  Ser  Pro  Phe  Gln  Glu  Asn  Trp  Phe  Leu  Leu  Phe  Cys
     290                      295                      300
Arg  Ile  Cys  Ile  Tyr  Leu  Asn  Ser  Ala  Ile  Asn  Pro  Val  Ile  Tyr  Asn
305                      310                 315                           320
Leu  Met  Ser  Gln  Lys  Phe  Arg  Ala  Ala  Phe  Arg  Lys  Leu  Cys  Asn  Cys
               325                      330                      335
Lys  Gln  Lys  Pro  Thr  Glu  Lys  Ala  Ala  Asn  Tyr  Ser  Val  Ala  Leu  Asn
               340                      345                 350
Tyr  Ser  Val  Ile  Lys  Glu  Ser  Asp  Arg  Phe  Ser  Thr  Glu  Leu  Asp  Asp
          355                      360                 365
Ile  Thr  Val  Thr  Asp  Thr  Tyr  Val  Ser  Thr  Thr  Lys  Val  Ser  Phe  Asp
     370                 375                      380
Asp  Thr  Cys  Leu  Ala  Ser  Glu  Lys  Asn  Gly  Pro  Ser  Ser  Cys
385                      390                 395
```

METHOD OF SCREENING FOR INHIBITORS OF HUMAN THYROTROPIN RELEASING HORMONE (TRH) RECEPTOR

FIELD OF THE INVENTION

The present invention relates to a human receptor protein capable of binding TRH which can be used as a diagnostic composition for neuropathy, a DNA comprising a DNA fragment coding for said protein which can be used as a pharmaceutical composition, a method for preparing said protein, and use of said protein and said DNA.

BACKGROUND

TRH (thyrotropin releasing hormone) was discovered from the hypothalami as a peptide promoting secretion of thyroid stimulating hormone and prolactin of the pituitary glands [A. V. Schally et al., Biochem. Biophys. Res. Commun., 25, 165–169 (1966)]. It has been reported that TRH is widely distributed in almost all sites of the brains other than the hypothalami, the spinal cords, the intestines, the pancreases, the adrenals and the like [J. E. Morley et al., Life Sciences, 25, 1539–1550 (1979)]. The fact that TRH is also distributed in the brains and the spinal cords suggests that TRH plays an important role in the function of the central nerve system. For example, the actual administration of TRH to organisms has been found to bring about various central nerve actions in animals [R. Guillemin, Recent Prog. Horm. Res., 33, 1–28 (1977)]. Also clinically, the administration of TRH has been reported to have therapeutic effect to schizophrenia [K. Inagata et al., Arch. Gen. Psychiatry, 35, 1011–1014 (1978)], melancholia [C. Hatanaka et al., Biochem. Biophys. Res. Commun., 60, 1350 (1974)], spinocerebellar degeneration [I. Sobue et al., Lancet, 1, 419 (1980)], as well as the improvement of disturbance of consciousness. Further, the existence of TRH in the nerve synapsis in the brains suggests that TRH acts as a neurotransmitter [T. Hokfelt et al., Eur. J. Pharmacol., 34, 389–392 (1975)].

On the other hand, binding tests using isotope-labeled TRH reveal that TRH receptors widely exist not only in the pituitary glands, but also in the brains and the spinal cords [N. A. Sharif, Ann. N. Y. Acad. Sci., 553, 147–175 (1989)]. Although there is a report that Scatchard plot analysis proves that TRH receptor molecules differ from one another in affinity between the pituitary and brain [K. Funatsu et al., J. Neurochem., 45, 390–397 (1985)], it is also reported that only one kind of receptor exist in the pituitary and brain [N. Ogawa et al., Peptides, 5, 743–746 (1984)]. TRH receptor-cDNAs have been cloned from pituitary tumor cell line of mice [R. E. Straub et al., Proc. Nat. Acad. Sci.. U.S.A., 87, 954–958 (1990)] and rats [P. Pena et al., Biochem. J., 284, 891–899 (1992); and D. Zhao et al., Endocrinology, 130, 3529–3536 (1992)]. Mouse TRH receptor cDNA has been reported to code for 393 amino acids. On the other hand, two isoforms are coded by the rat TRH receptor cDNA, i.e. 412 amino acids and 387 amino acids respectively, which are considered to be produced by alternative splicing [P. Pena et al., J. Biol. Chem., 267, 25708–25708 (1992)]. Further, primary sequences of amino acids encoded by these cDNAs suggest that TRH receptor is a member of G-protein couple receptors with 7 transmembrane domains. It is not known whether receptor subtypes exist in addition to the TRH receptors. Certain experiments using tumor cells $GH_3$ of the rat pituitary glands have been reported to provide an indication that a signal transduction of the TRH receptors is conjugated with an inositol phosphate turnover and calcium mobilization [T. F. J. Martin et al., J. Biol. Chem., 261, 10141–10146 (1986)]. It is reported that the TRH receptors in the rat brain are conjugated with the inositol lipid metabolic turnover and the formation of cAMP [M. Mori et al., Research Communications in Chemical Pathology and Pharmacology, 71, 17–26 (1991)].

Synthesis of certain derivatives of TRH have been reported, and binding activity to TRH receptors has been examined. It has been observed that some of these compounds bind to the TRH receptors [S. M. Simasko and A. Horita, Life Sci., 30, 1793–1799 (1982)] and also have effect on the central nerve system including acetylcholine-release stronger than TRH [M. Shikata et al., Japan. J. Pharmacol., 32, 883–891 (1982); and P. H. Huston et al., Neurosci. Lett., 116, 149–155 (1990)]. Some agonists or antagonists to the TRH receptors may be useful as drugs acting on the human central nerve system. When the agonists or the antagonists to the TRH receptors as the drugs acting on the human central nerve system are screened, it is conceivable to use human tissue or cells in which the TRH receptors are expressed, thereby screening substances binding to the receptors as primary screening. However, it is generally not possible to obtain such human tissue. Also, culture cells in which the human TRH receptors are expressed are little known. On the other hand, it is possible to use animal tissue or cells in which the TRH receptors are expressed, thereby conducting screening. In this case, however, the difference in characteristics of the receptors between animal species, so-called species specificity of the receptors, is a problem. In addition to the above, no culture cells in which the human TRH receptors are expressed have been available, so that there has been no means for examining the signal transduction of the human TRH receptors at all.

As a means for solving such a problem, if human TRH receptor genes can be cloned, the human TRH receptors can be expressed in animal cells and the like using them by an appropriate means. It is therefore considered that screening and studies of the human TRH receptor agonists and antagonists can be largely advanced. However, there is no information for human genes of the receptor proteins capable of binding human TRH as yet.

SUMMARY OF THE INVENTION

An object of the present invention is to provide a human receptor protein capable of binding TRH which is useful for screening of human TRH receptor agonists or antagonists acting on the human central nerve system.

Another object of the present invention is to provide a DNA coding for said protein.

A further object of the present invention is to provide a method for preparing said protein.

The present inventors conducted intensive investigations, in view of the above-mentioned situation, considering that the preparation of human TRH receptor genes by cloning according to recombinant technology will greatly contribute to the studies of TRH, TRH receptor agonists and TRH receptor antagonists, and the development of drugs using them. Among other things, the present inventors succeeded in cloning a DNA fragment coding for a human TRH receptor from a human genomic DNA library, and in determining its nucleotide sequence. Additionally, an amino acid sequence of a human receptor protein capable of binding TRH was determined.

More particularly, the present invention includes:

(1) A human receptor protein capable of binding TRH, or a salt thereof;

(2) The receptor protein of (1) which comprises an amino acid sequence represented by SEQ ID NO: 1;

(3) A receptor fragment containing a sufficient portion of a human receptor protein to bind TRH, or a salt thereof;

(4) The receptor or the salt thereof of (3) which comprises
1) from about the 1st to 13th residues of the sequence represented by SEQ ID NO:1;
2) from about the 1st to 20th residues of the sequence represented by SEQ ID NO:1;
3) from about the 50th to 59th residues of the sequence represented by SEQ ID NO:1;
4) from about the 180th to 187th residues of the sequence represented by SEQ ID NO:1;
5) from about the 221st to 252nd residues of the sequence represented by SEQ ID NO:1;
6) from about the 232nd to 251st residues of the sequence represented by SEQ ID NO:1;
7) from about the 255th to 262nd residues of the sequence represented by SEQ ID NO:1;
8) from about the 292nd to 297th residues of the sequence represented by SEQ ID NO:1;
9) from about the 331st to 345th residues of the sequence represented by SEQ ID NO:1;
10) from about the 353rd to 366th residues of the sequence represented by SEQ ID NO:1; or
11) from about the 384th to 398th residues of the sequence represented by SEQ ID NO:1;

(5) A DNA comprising a DNA sequence having a nucleotide sequence coding for a human receptor protein capable of binding TRH;

(6) The DNA of (5), wherein the receptor protein comprises an amino acid sequence represented by SEQ ID NO: 1;

(7) The DNA of (6), wherein the DNA sequence has a nucleotide sequence represented by SEQ ID NO: 2;

(8) A vector containing the DNA of (5);

(9) A transformant containing the DNA of (5) or the vector of (8);

(10) A method for preparing a human receptor protein capable of binding TRH or a salt thereof comprising cultivating the transformant of (9), and accumulating said receptor protein in a culture product;

(11) A pharmaceutical composition comprising a neuropathy treatment effective amount of the DNA of (5);

(12) The pharmaceutical composition of (11), which is for vertebrocerebellum degeneration, disorder of consciousness, schizophrenia, depression, dementia or Alzheimer's disease;

(13) A pharmaceutical composition for releasing acetylcholine or arachidonic acid comprising the DNA of (5);

(14) A diagnostic composition suitable for testing for a neuropathy condition comprising the receptor protein or the salt thereof of (1), or the receptor fragment or the salt thereof of (3);

(15) The diagnostic composition of (14), which is for vertebrocerebellum degeneration, disorder of consciousness, schizophrenia, depression, dementia or Alzheimer's disease;

(16) A method for determining the concentration of TRH contained in a test sample comprising contacting the test sample with 1) the receptor protein or the salt thereof of (1), or 2) the receptor fragment or the salt thereof of (3);

(17) A method for diagnosing neuropathy comprising contacting the test sample with 1) the receptor protein or the salt thereof of (1), or 2) the receptor fragment or the salt thereof of (3);

(18) The method of (17), wherein said neuropathy is vertebrocerebellum degeneration, disorder of consciousness, schizophrenia, depression, dementia or Alzheimer's disease;

(19) A method for screening a compound that can antagonize binding of TRH to a human TRH receptor, or a salt thereof, comprising using the receptor protein or the salt thereof of (1), or the receptor fragment or the salt thereof of (3);

(20) A method for screening a compound that can antagonize binding of TRH to a human TRH receptor, or a salt thereof, comprising using the DNA of (5);

(21) A method for screening a compound that can antagonize binding of TRH to a human TRH receptor, or a salt thereof, comprising comparing the amounts of a labeled ligand bound to the receptor protein or the salt thereof of (1), or to the receptor fragment or the salt thereof of (3) determined from the following steps (a) and (b);

(a) contacting the labeled ligand with the receptor protein or the salt thereof of (1), or with the receptor fragment or the salt thereof of (3), (b) contacting the labeled ligand and a test compound with the receptor protein or the salt thereof of (1), or with the receptor fragment or the salt thereof of (3);

(22) The method of (21), wherein the steps (a) and (b) are (a) contacting the labeled ligand with a cell which contains the receptor protein or the salt thereof of (1), (b) contacting the labeled ligand and a test compound with a cell which contains the receptor protein or the salt thereof of (1);

(23) The method of (21), wherein the steps (a) and (b) are (a) contacting said labeled ligand with a membrane fraction of a cell containing the receptor protein of (1), (b) contacting said ligand and said test compound with the membrane fraction of the cell containing the receptor protein of (1);

(24) A method for screening a compound that can antagonize binding of TRH to a human TRH receptor, or a salt thereof, comprising comparing the amounts of a labeled ligand bound to a receptor protein or the salt thereof in steps of (a) and (b);

(a) contacting the labeled ligand with the TRH receptor protein which was expressed on a cell membrane by cultivating the transformant comprising the DNA of (5), (b) contacting the labeled ligand and a test compound with the TRH receptor protein which was expressed on a cell membrane by cultivating the transformant comprising the DNA of (5);

(25) The method of (21) to (24), wherein said labeled ligand is [$^3$H]TRH;

(26) A method for screening a compound that can antagonize binding of TRH to a human TRH receptor, or a salt thereof, comprising comparing cell stimulating activities (for example, mobilization of $Ca^{2+}$ in the cells, hyper metabolism of inositole phosphate, activation of adenylate cyclase and activation of c-fos) through a TRH receptor determined from the following steps (a) and (b);

(a) contacting a TRH receptor-activating compound with a cell which comprises the receptor protein of (1), (b) contacting a TRH receptor-activating compound and a test compound with a cell which comprises the receptor protein of (1);

(27) A method for screening a compound that can antagonize binding of TRH to a human TRH receptor, or a salt thereof, comprising comparing cell stimulating activities through a TRH receptor in cases of (a) and (b);

(a) contacting a TRH receptor-activating compound with the TRH receptor protein which was expressed on a cell membrane by cultivating the transformant comprising the DNA of (5), (b) contacting a TRH receptor-activating compound and a test compound with the TRH receptor protein which was expressed on a cell membrane by cultivating the transformant comprising the DNA of (5);

(28) The method of (26) or (27), wherein said TRH receptor-activating compound is TRH;

(29) A compound or a salt thereof obtained by the method of (19) to (28);

(30) A pharmaceutical composition comprising a neuropathy treatment effective amount of the compound or salt thereof of (29);

(31) The pharmaceutical composition of (30), which is for vertebrocerebellum degeneration, disorder of consciousness, schizophrenia, depression, dementia or Alzheimer's disease;

(32) A pharmaceutical composition for releasing acetylcholine or arachidonic acid comprising a compound or a salt thereof of (29);

(33) A compound that can antagonize binding of TRH to a human TRH receptor and having TRH receptor agonist activity or a salt thereof obtained by the method of any one of (19) to (28);

(34) A pharmaceutical composition for neuropathy comprising a compound that can antagonize binding of TRH to a human TRH receptor and having TRH receptor agonist activity or a salt thereof obtained by the method of any one of (19) to (28);

(35) The pharmaceutical composition of (34) which is for vertebrocerebellum degeneration, disorder of consciousness, schizophrenia, depression, dementia or Alzheimer's disease;

(36) A pharmaceutical composition for releasing acetylcholine or arachidonic acid comprising a compound that can antagonize binding of TRH to a human TRH receptor and having TRH receptor agonist activity or a salt thereof obtained by the method of any one of (19) to (28);

(37) A kit for screening a compound that can antagonize binding of TRH to a human TRH receptor, or a salt thereof, comprising the receptor protein or the salt thereof of (1), or the receptor fragment or the salt thereof of (3);

(38) The kit of (37) comprising a cell containing the TRH receptor protein of (1);

(39) The kit of (37) comprising a membrane fraction of a cell containing the TRH receptor protein of (1);

(40) A compound or a salt thereof obtained by use of the kit of any one of (37) to (39);

(41) A pharmaceutical composition for neuropathy comprising the compound or the salt thereof of (40);

(42) The pharmaceutical composition of (41) which is for dementia or Alzheimer's disease;

(43) A pharmaceutical composition for releasing acetylcholine or arachidonic acid comprising the compound or the salt thereof of (40);

(44) A compound that can antagonize binding of TRH to a human TRH receptor and having TRH receptor agonist activity or a salt thereof obtained by use of the kit of any one of (37) to (39);

(45) A pharmaceutical composition for neuropathy comprising a compound that can antagonize binding of TRH to a human TRH receptor and having TRH receptor agonist activity or a salt thereof obtained by use of the kit of any one of (37) to (39);

(46) The pharmaceutical composition of (45) which is for vertebrocerebellum degeneration, disorder of consciousness, schizophrenia, depression, dementia or Alzheimer's disease;

(47) A pharmaceutical composition for releasing acetylcholine or arachidonic acid comprising a compound that can antagonize binding of TRH to a human TRH receptor and having TRH receptor agonist activity or a salt thereof obtained by use of the kit of any one of (37) to (39);

(48) An antibody that binds to the receptor protein or the salt thereof of (1), or to the receptor fragment or the salt thereof of (3);

(49) A method of treating a mammal that is suffering from or susceptible to a neuropathic condition, comprising administering an effective amount of the DNA of (5) to mammal; and

(50) The method of (49), wherein the neuropathic condition is vertebrocerebellum degeneration, disorder of consciousness, schizophrenia, depression, dementia or Alzheimer's disease.

BRIEF DESCRIPTION OF THE DRAWINGS

FIG. 1 shows a restriction enzyme cleavage map of a genomic DNA fragment coding for a human TRH receptor protein, and a procedure of analysis of a nucleotide sequence. Fragment (A) is inserted into phTRHR919, and fragment (B) into phTRHR316;

FIG. 2 shows a nucleotide sequence (SEQ ID NO: 13) of the genome DNA fragment coding for the human TRH receptor protein inserted into phTRHR919. A translation initiation codon ATG and a splicing signal GTAAGC are underlined;

FIG. 3 shows a nucleotide sequence (SEQ ID NO: 14) of the genome DNA fragment coding for the human TRH receptor protein inserted into phTRHR316. A splicing signal TTCTCCCTAG and a translation termination codon TGA are underlined;

FIG. 4 shows a nucleotide sequence (SEQ ID NO: 3) of a translation frame of a human TRH receptor protein (SEQ ID NO: 1) gene deduced from phTRHR919 and phTRHR316. An intron-inserted portion is indicated by the arrow;

FIG. 5 shows amino acid sequences of human (SEQ ID NO: 1) and rat TRH receptor (SEQ ID NO: 15) proteins in comparison with each other. Amino acid residues which agree with each other between the human sequence (h) and the rat sequence (r) are indicated by asterisks (*);

DESCRIPTION OF THE PREFERRED EMBODIMENTS

Figure 6A:
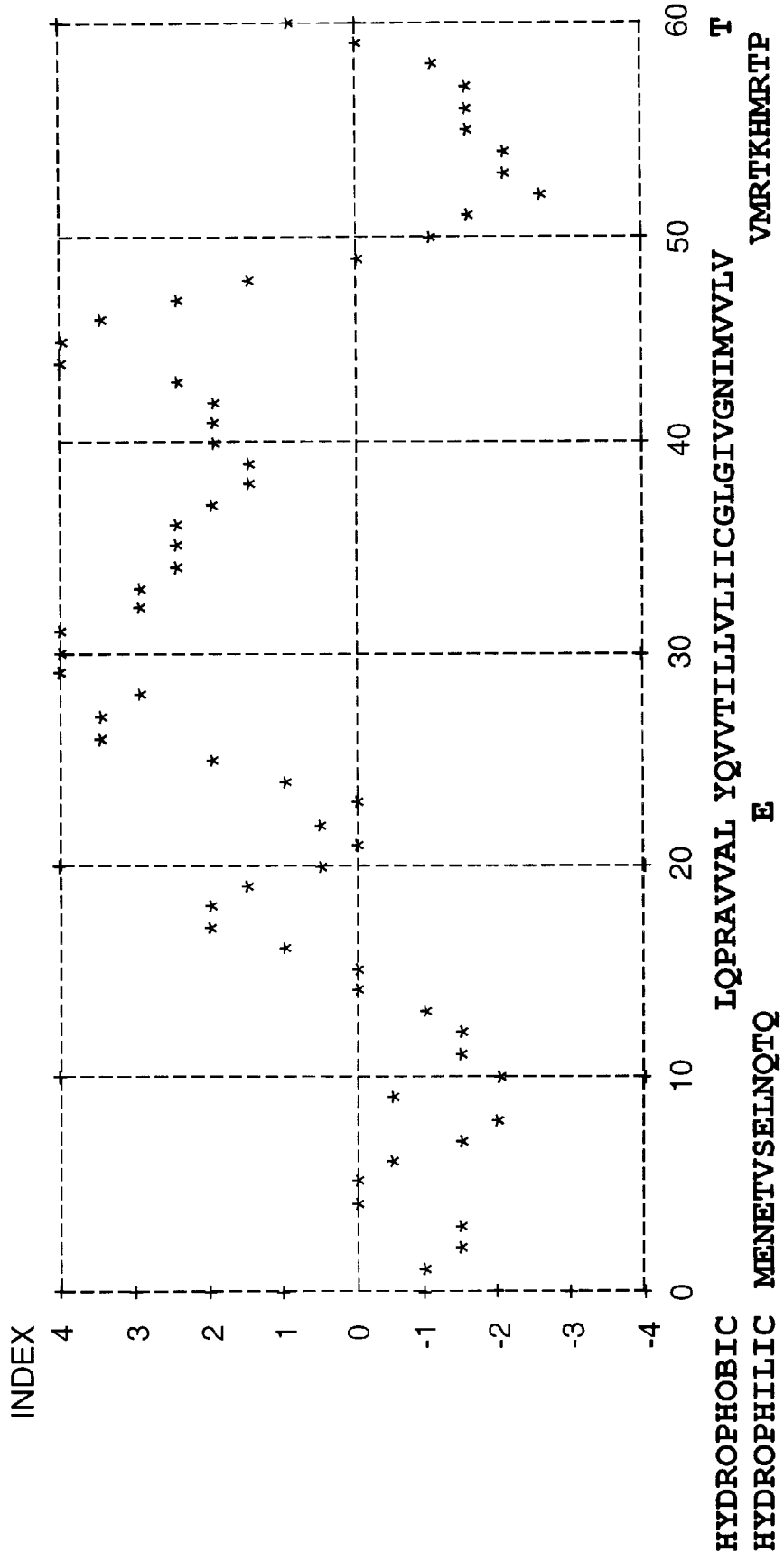
FIG. 6 shows graphs based on the degree of hydrophobicity of a human TRH receptor protein.
Figure 6B:
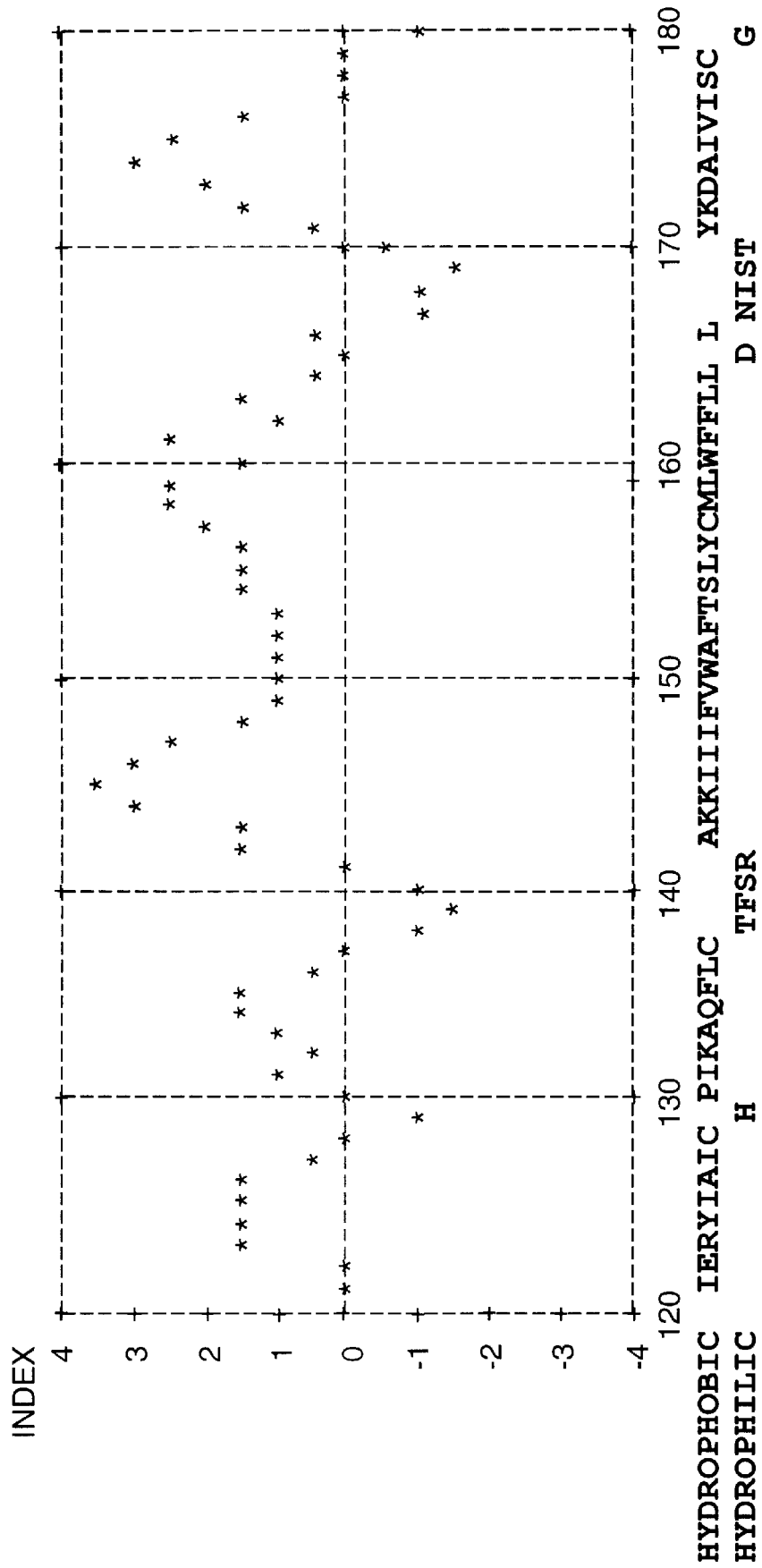
Figure 6C:
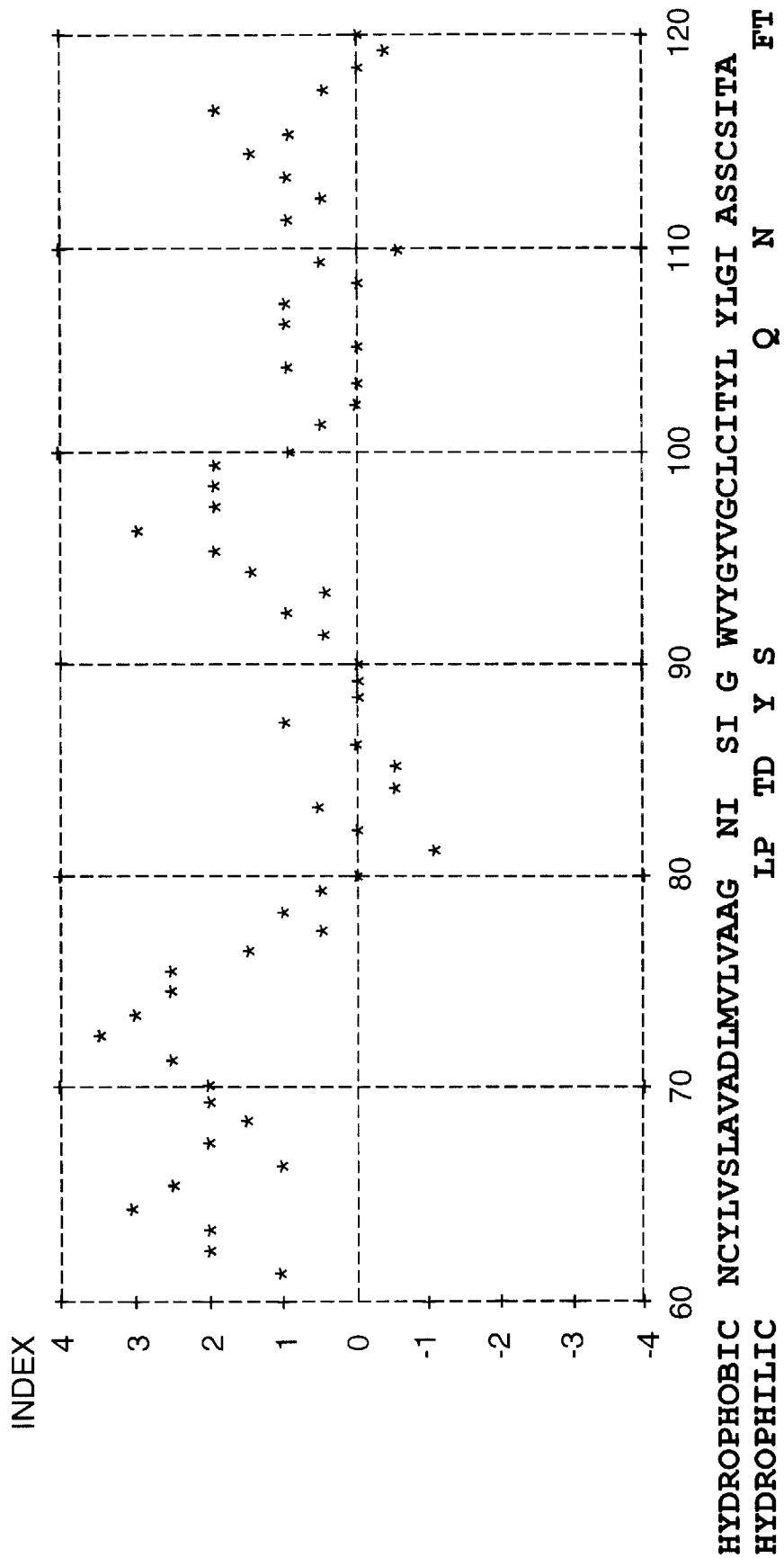
Figure 6D:
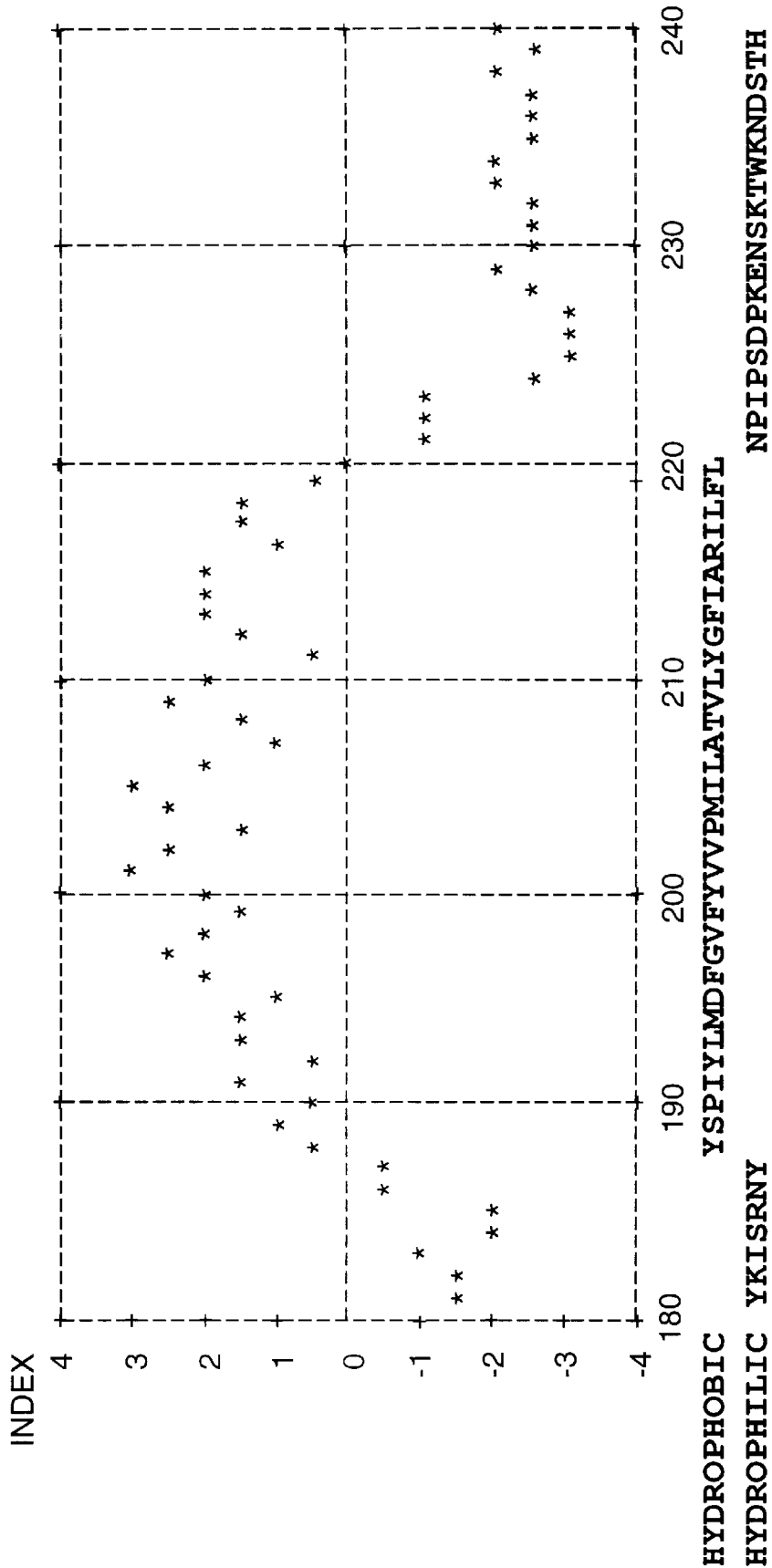

More specifically, the present inventors cloned two kinds of DNA fragments (A) and (B) shown in FIG. 1 as DNA fragments coding for the human TRH receptor proteins, and determined their nucleotide sequences (FIGS. 2 and 3). In FIG. 1, the box portions show regions coding for the human TRH receptor proteins. Fragment (A) was inserted into phTRHR919, and fragment (B) into phTRHR316. In FIG. 2, a translation initiation codon ATG and a splicing signal GTAAGC are underlined. In FIG. 3, a splicing signal TTCTCCCTAG and a translation termination codon TGA are underlined. The complete primary structure of the protein in a translation region derived therefrom was deduced (FIG. 4). In FIG. 4, an intron-inserted portion is indicated by the arrow. The amino acid sequence of SEQ ID NO: 1 shown in the sequence listing indicates the amino acid sequence of the human TRH receptor protein shown in FIG. 4. The nucleotide sequence of SEQ ID NO: 2 shown in the sequence listing indicates a nucleotide sequence coding the protein out of the nucleotide sequence shown in FIG. 4. The nucleotide sequence of SEQ ID NO: 3 shown in the sequence listing indicates the whole nucleotide sequence of FIG. 4. In the sequences shown in FIGS. 2 and 3, there exist the initiation codon ATG, the termination codon TGA and the sequences TTCTCCCTAG and GTAAGC which agree very well with the splicing signals, respectively. Based on these sequences, a translation frame as shown in FIG. 4 was obtained from a sequence bound excluding the sequence of the intron portion. The protein deduced from this translation frame was composed of 398 amino acid residues. The amino acid sequence of this human TRH receptor protein showed 93.75% identity with the amino acid sequence of the rat TRH receptor already reported, which revealed that it coded for the human TRH receptor protein (FIG. 5). In the receptor protein capable of binding rat TRH (hereinafter referred to as the rat TRH receptor protein), an intron is considered not to exist at a position at which it exists in the human TRH receptor protein [P. Pena et al., *J. Biol. Chem.*, 267, 25703–25708 (1992)]. Further, the third exon coding for an additional amino acid sequence possibly exists at this position. The structure of the human TRH receptor protein derived such a human gene is similar to that of the rat TRH receptor protein, but shows the difference in amino acids, and an intron which possibly contains the unknown exon is contained in its translation frame. Accordingly, clarification of the structure of the human TRH receptor protein is required to promote the development of drugs acting through the TRH receptors.

The human TRH receptor proteins of the present invention may be any proteins, as long as they have human-derived TRH receptor activity (the TRH receptor activity means the action of specifically binding to TRH). Binding affinity of human TRH receptor protein of the present invention on TRH is about $5.0\times10^{-7}$M to about $5.0\times10^{-11}$M, and preferably about $5.0\times10^{-8}$M to about $5.0\times10^{-10}$M. Examples thereof include proteins having amino acid sequences containing the amino acid sequence represented by SEQ ID NO: 1.

Furthermore, the human TRH receptor proteins of the present invention also comprise proteins in which the N-terminal Met residues are protected with protective groups (for example, $C_{1-6}$ acyl groups such as formyl and acetyl), a protein in which the N-terminal side of Glu in the amino acid sequence represented by SEQ ID NO: 1 is cleaved in vivo and the Glu residue is pyroglutaminated, proteins in which side chains of amino acids in molecules are protected with appropriate protective groups, and conjugated proteins such as so-called glycoproteins to which sugar chains are bound.

As the salts of the human TRH receptor proteins of the present invention, physiologically acceptable acid addition salts are preferred among others. Examples of such salts include salts with inorganic acids (such as hydrochloric acid, phosphoric acid, hydrobromic acid and sulfuric acid) and salts with organic acids (such as acetic acid, formic acid, propionic acid, fumaric acid, maleic acid, succinic acid, tartaric acid, citric acid, malic acid, oxalic acid, benzoic acid, methanesulfonic acid and benzenesulfonic acid).

The human TRH receptor proteins or the salts thereof of the present invention can be produced by known methods for purifying proteins, and can also be produced by use of DNAs coding for the human TRH receptor proteins described below.

Figure 7A:
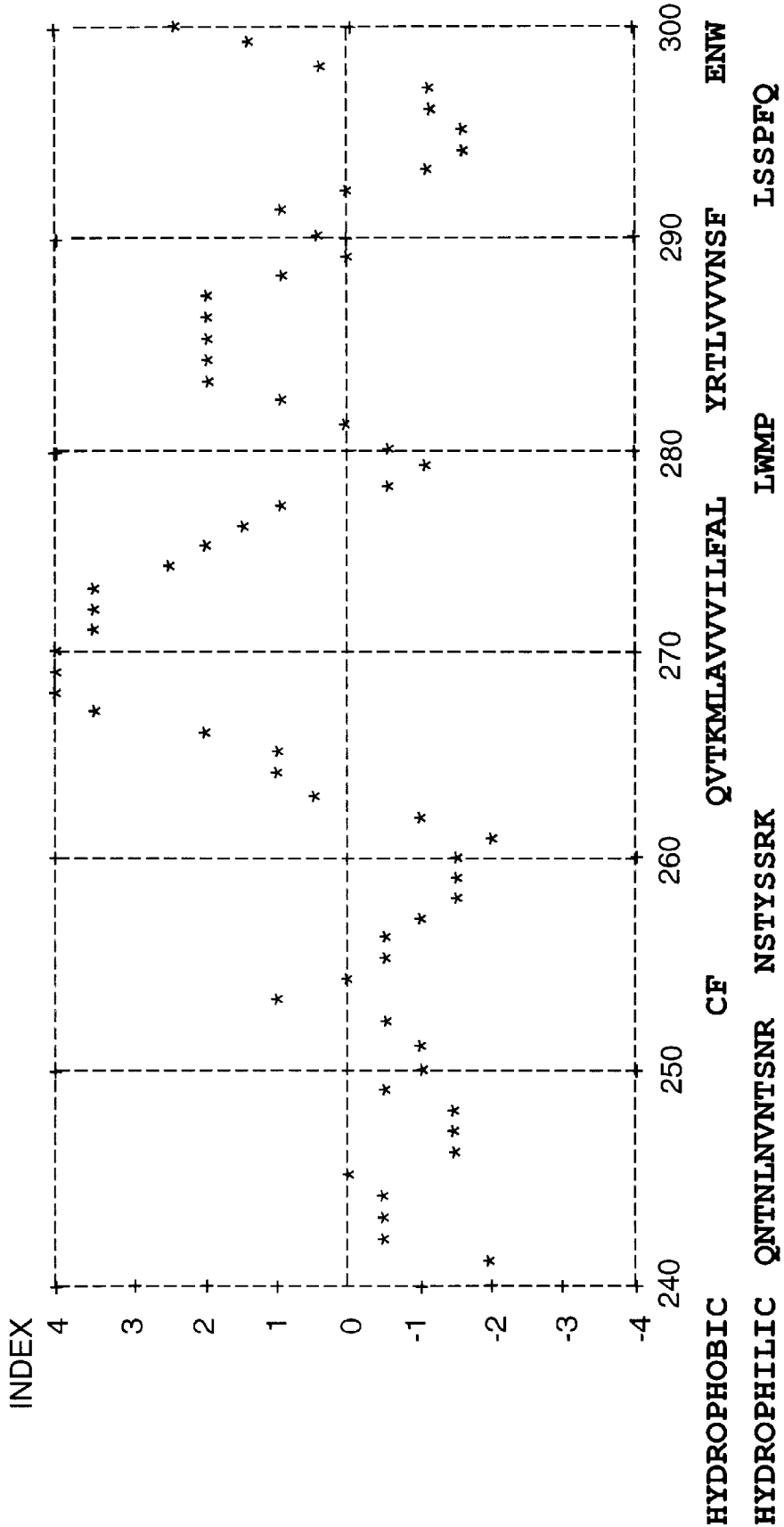
FIG. 7 shows graphs based on the degree of hydrophobicity of a human TRH receptor protein.
Figure 7B:
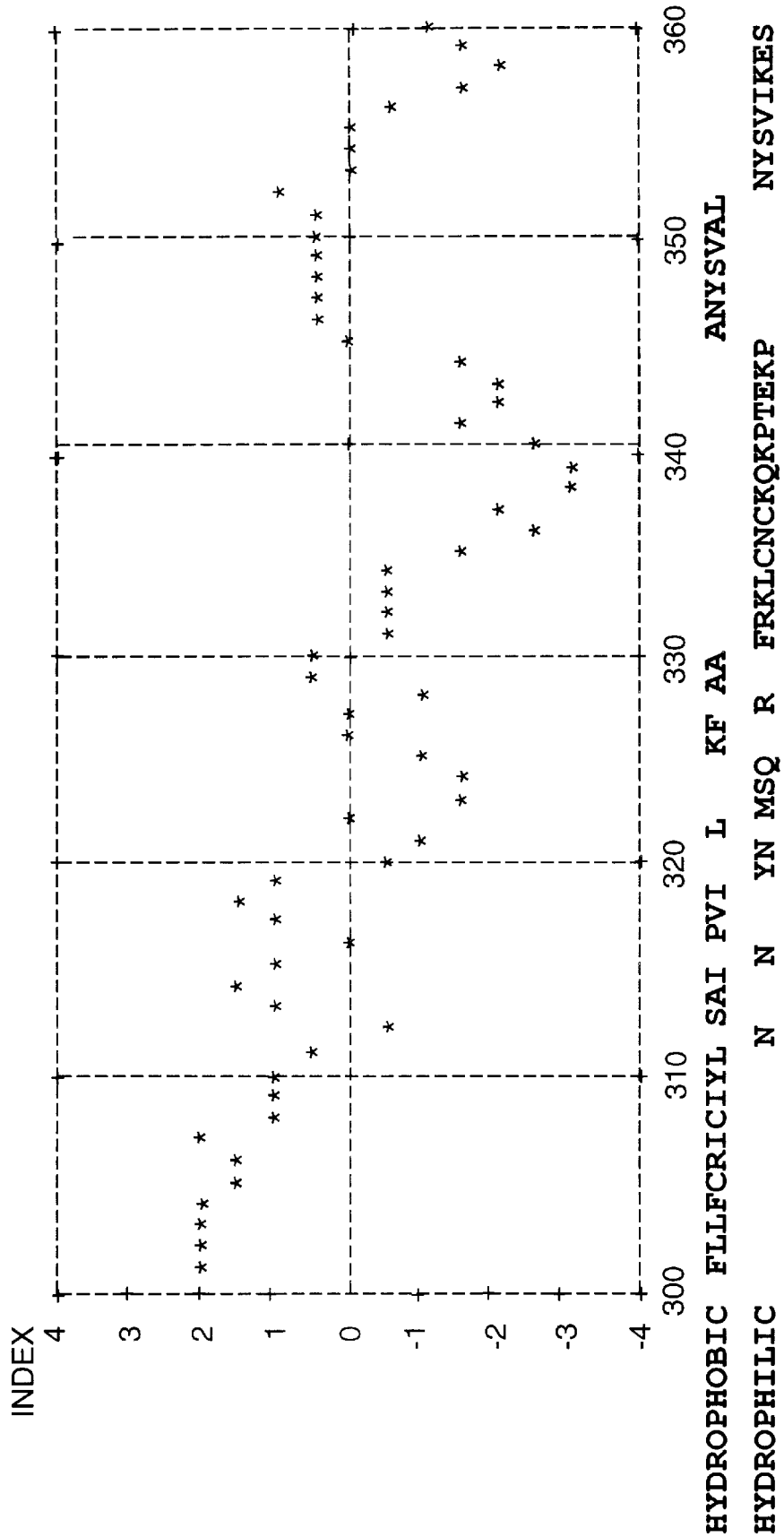
Figure 7C:
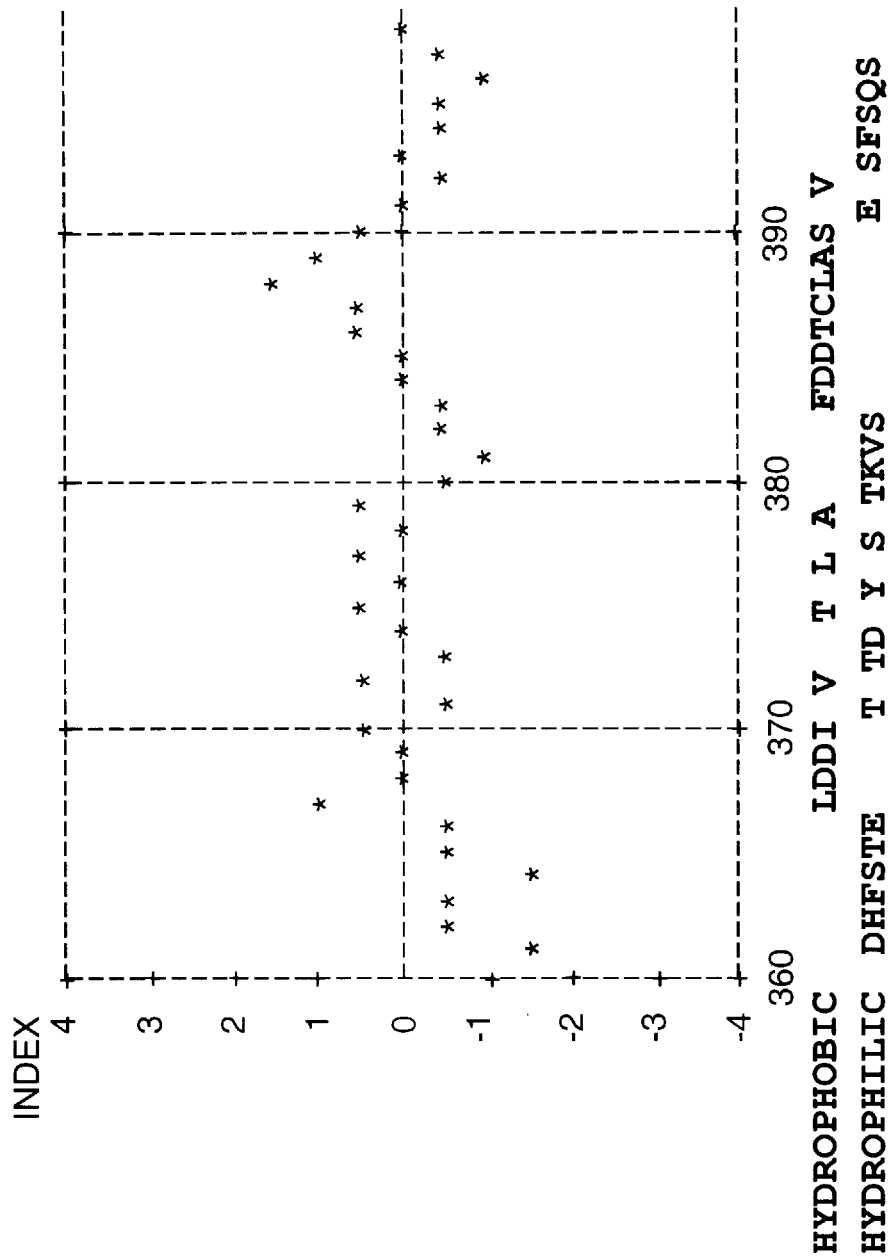

The human TRH receptor fragments of the present invention may be any peptides, as long as they have human-derived TRH receptor activity. That is, human TRH receptor fragments of the present invention bind to TRH. For example, sites of TRH receptor protein molecules exposed out of cell membranes are used. Specifically, they are partial peptides deduced to be extracellular regions (hydrophilic sites) in hydrophobic plot analysis shown in FIGS. 6 and 7. Examples thereof include peptides comprising; (1) from the 1st to 13th residues of the sequence represented by SEQ ID NO:1; (2) from the 50th to 59th residues of the sequence represented by SEQ ID NO:1; (3) from the 180th to 187th residues of the sequence represented by SEQ ID NO:1; (4) from the 221st to 252nd residues of the sequence represented by SEQ ID NO:1; (5) from the 255th to 262nd residues of the sequence represented by SEQ ID NO:1; (6) from the 292nd to 297th residues of the sequence represented by SEQ ID NO:1; (7) from the 331st to 345th residues of the sequence represented by SEQ ID NO:1; or (8) from the 353rd to 366th residues of the sequence represented by SEQ ID NO:1.

Further preferred TRH recetor fragments of the invention include those specific to human TRH receptor, including peptides that comprise (1) from the 1st to 20th residues of the sequence represented by SEQ ID NO:1; (2) from the 232nd to 251st residues of the sequence represented by SEQ ID NO:1; or (3) from the 384th to 398th residues of the sequence represented by SEQ ID NO:1.

As the salts of the human TRH receptor fragments of the invention, physiologically acceptable acid addition salts are preferred among others. Examples of such salts include salts with inorganic acids (such as hydrochloric acid, phosphoric acid, hydrobromic acid and sulfuric acid) and salts with organic acids (such as acetic acid, formic acid, propionic acid, fumaric acid, maleic acid, succinic acid, tartaric acid, citric acid, malic acid, oxalic acid, benzoic acid, methanesulfonic acid and benzenesulfonic acid).

The human TRH receptor protein and human TRH receptor protein fragments or the salts thereof of the present invention can be produced by known methods for synthesizing peptides or by cleaving the human TRH receptor proteins with appropriate peptidases. As the methods for synthesizing peptides, for example, either solid phase synthesis methods or liquid phase synthesis methods may be employed. Namely, the desired peptides can be produced by condensing partial peptides or amino acids which can constitute the proteins of the present invention with residual moieties, and eliminating protective groups when the products have the protective groups. Known condensing methods and elimination of the protective groups include, for example, methods described in the following documents (1) to (5):

(1) M. Bodansky and M. A. Ondetti, *Peptide Synthesis,* Interscience Publishers, New York (1966);

(2) Schroeder and Luebke, *The Peptide,* Academic Press, New York (1965);

(3) N. Izumiya et al., *Peptide Gosei no Kiso to Jikken* (*Fundamentals and Experiments of Peptide Synthesis*), Maruzen (1985);

(4) H. Yazima, S. Sakakibara et al., *Seikagaku Jikken Koza* (*Course of Biochemical Experiments*), 1, *Chemistry of Proteins IV,* 205 (1977); and (5) *Zoku Ivakuhin no Kaihatu* (*Development of Drugs*) second series), 14, *Peptide Synthesis,* supervised by H. Yazima, Hirokawa Shoten.

After reaction, the proteins of the present invention can be isolated by combinations of usual purification methods such as solvent extraction, distillation, repreciptation, column chromatography, liquid chromatography, and recrystallization. When the proteins are obtained in the free form by the above-mentioned methods, they can be converted to appropriate salts by known methods. Conversely, when the proteins are obtained in the salt state, they can be converted to the free forms by known methods.

The DNAs coding for the human TRH receptor proteins or fragments thereof of the present invention may be any, as long as they have nucleotide sequences coding for the human TRH receptor proteins or fragments. Namely, the DNAs encoding the human TRH receptor proteins of the present invention may be either of cDNA, and genomic DNA. Examples of the DNAs used herein include the DNA having the nucleotide sequence of SEQ ID NO: 2 coding for the human TRH receptor proteins and the DNA having the nucleotide sequence of SEQ ID NO: 3 containing the DNA having the nucleotide sequence of SEQ ID NO: 2. Screening of the DNAs can be conducted by general genetic engineering techniques or methods based thereon, for example, based on examples given below. As DNAs coding for a fragment of the human TRH receptor protein, a DNA fragment that encodes the peptide fragment of the nucleotide sequence of SEQ ID NO:2 can be used.

Expression vectors for the human TRH receptor proteins can be produced by (a) restricting desired DNA fragments from the DNAs encoding the human TRH receptor proteins, and (b) ligating the DNA fragments downstream from promoters in appropriate vectors.

The cloned DNAs encoding the human TRH receptor proteins can be used as such, or after digestion with restriction enzymes or addition of linkers if desired, depending on their purpose.

The DNA may have ATG as a translation initiation codon on the 5'-terminal side, and TAA, TGA or TAG as a translation termination codon on the 3'-terminal side. The translation initiation codon and translation termination codon may be added by use of an appropriate synthetic DNA adaptor. A promoter is further ligated upstream therefrom to express the DNA.

The vectors include plasmids derived from *Escherichia coli* (for example, pBR322, pBR325, pUC12 and pUC13), plasmids derived from *Bacillus subtilis* (for example, pUB110, pTP5 and pC194), plasmids derived from yeast (for example, pSH19 and PSH15, bacteriophages such as λ phage, and animal viruses such as retroviruses, vaccinia viruses and baculoviruses.

As the promoter used in the present invention, any promoter is available as long as it is suitable for expression corresponding to a host cell used for the gene expression.

When the host cell used for transformation is Escherichia, a trp promoter, a lac promoter, a recA promoter, a λPL promoter or an 1 pp promoter is preferred. When the host cell is Bacillus, an SPO1 promoter, an SPO2 promoter or a penP promoter is preferred. When the host cell is yeast, a PHO5 promoter, a PGK promoter, a GAP promoter or an ADH promoter is preferred.

When the host cell is an animal cell, an SV40-derived promoter, a retrovirus promoter (for example, HTLV-1 LTR-derived SRα promoter), metallothionein promoter, a heat shock promoter or a cytomegalovirus promoter is usable.

An enhancer is also effectively utilized for expression.

Further, a signal sequence corresponding to the host cell is added to the N-terminal side of the TRH receptor protein if necessary. When the host cell is Escherichia, an alkaline phosphatase-signal sequence or an OmpA-signal sequence is available. When the host cell is Bacillus, an α-amylase-signal sequence or a subtilisin-signal sequence is available. When the host cell is yeast, a mating factor α-signal sequence or an invertase-signal sequence is available. When the host cell is an animal cell, for example, an insulin-signal sequence, an α-interferon-signal sequence or an antibody molecule-signal sequence is available.

Using the vectors containing the DNAs coding for the human TRH receptor proteins thus constructed, transformants are prepared.

Examples of the host cells include Escherichia, Bacillus, yeast, insects and animal cells.

Examples of the above-mentioned Escherichia include *E. coli* K12·DH1 [*Proc. Natl. Acad. Sci. U.S.A.*, 60, 160 (1968)], JM103 [*Nucleic Acids Research*, 9, 309 (1981)], JA221 [*Journal of Molecular Biology*, 120, 517, (1978)], HB101 [*Journal of Molecular Biology*, 41, 459 (1969)] and C600 [*Genetics*, 39, 440 (1954)].

Examples of the above-mentioned Bacillus include *Bacillus subtilis* MI114 [*Gene*, 24, 255 (1983)] and 207–21 [*Journal of Biochemistry*, 95, 87 (1984)].

Examples of the above-mentioned yeast include *Saccharomyces cerevisiae* AH22, AH22R$^-$, NA87-11A, DKD-5D and 20B-12.

Examples of the insects include larvae of silk worms [Maeda et al., *Nature*, 315, 592 (1985)].

Examples of the animal cells include monkey cell COS-7, Vero, Chinese hamster cell (CHO), mouse L cell, mouse myeloma cell and human FL cell.

The transformation of the above-mentioned Escherichia is conducted, for example, according to the method described in *Proc. Natl. Acad. Sci. U.S.A.*, 69, 2110 (1972), *Gene*, 17, 107 (1982) or the like.

The transformation of the Bacillus is carried out, for example, according to the method described in *Molecular & General Genetics*, 168, 111 (1979) or the like.

The transformation of the yeast is performed, for example, according to the method described in *Proc. Natl. Acad. Sci. U.S.A.*, 75, 1929 (1978).

The transformation of the insects is conducted, for example, according to the method described in *Bio/Technology*, 6, 47–55 (1988) or the like.

The transformation of the animal cells is carried out, for example, according to the method described in *Virology*, 52, 456 (1973).

Thus, the transformants transformed with the expression vectors containing the cDNAs coding for the human TRH receptor proteins are obtained.

When the bacterial transformants are cultivated, a liquid medium is typically used for cultivation. Carbon sources, nitrogen sources, inorganic compounds and other nutrients necessary for growth of the transformants are contained therein. Examples of the carbon sources include glucose, dextrin, soluble starch and sucrose. Examples of the nitrogen sources include inorganic or organic materials such as ammonium salts, nitrates, corn steep liquor, peptone, casein, meat extracts, soybean meal and potato extract solution. The inorganic compounds include, for example, calcium chloride, sodium dihydrogenphosphate and magnesium chloride. Yeast, vitamins and growth promoting factors, etc. may be further added. The pH of the medium is preferably about 5 to about 8.

When the Escherichia transformants are cultivated, M9 medium containing glucose and Casamino Acids [Miller, *Journal of Experiments in Molecular Genetics*, 431–433, Cold Spring Harbor Laboratory, New York (1972)] is preferably used to cultivate the transformants. In order to allow the promoters to act more efficiently, for example, drugs such as 3β-indolyl acrylic acid may be added thereto if necessary.

The Escherichia transformants are usually cultivated at about 15° to about 43° C. for about 3 to about 24 hours with aeration or agitation if necessary.

The Bacillus transformants are usually cultivated at about 30° to about 40° C. for about 6 to about 24 hours with aeration or agitation if necessary.

When the yeast transformants are cultivated, a preferred medium is Burkholder minimum medium [K. L. Bostian, *Proc. Natl. Acad. Sci. U.S.A.*, 77, 4505 (1980)] or SD medium containing 0.5% Casamino Acids [G. A. Bitter et al., *Proc. Natl. Acad. Sci. U.S.A.*, 81, 5330 (1984)]. The pH of the medium is preferably adjusted to about 5 to about 8. The cultivation is usually carried out at about 20° to about 35° C. for about 24 to about 72 hours with aeration or agitation if necessary.

When the insect transformants are cultivated, examples of media used include Grace's insect medium [(T. C. C. Grace, *Nature*, 195, 788 (1962)] supplemented with an additive such as 10% inactivated bovine serum. The pH of the medium is preferably adjusted to about 6.2 to about 6.4. The cultivation is usually carried out at about 27° C. for about 3 to about 5 days with aeration or agitation if necessary.

When the animal cell transformants are cultivated, examples of media used include MEM medium containing about 5 to about 20% fetal calf serum [*Science*, 122, 501 (1952)], DMEM medium [*Virology*, 8, 396 (1959)], RPMI 1640 medium [*Journal of the American Medical Association*, 199, 519 (1967)] and 199 medium [*Proceeding of the Society for the Biological Medicine*, 73, 1 (1950)]. The pH is preferably about 6 to about 8. The cell culture is usually carried out at about 30° to about 40° C. for about 15 to about 60 hours, with aeration or agitation if necessary.

The isolation and purification of the human TRH receptor proteins from the above-mentioned culture products can be carried out, for example, according to the following methods.

When the human TRH receptor protein is to be extracted from cultured cells, the cells are collected by methods known in the art after cultivation. Then, the collected cells are suspended in an appropriate buffer solution, and disrupted by ultrasonic treatment, lysozyme treatment and/or freeze-thawing, thereby releasing the receptor protein, followed by centrifugation to obtain a crude extract of the receptor protein. The buffer solution may contain a protein denaturant such as urea or guanidine hydrochloride, or a detergent such as Triton X-100 (registered trade mark, hereinafter also referred to as "TM").

When the human TRH receptor protein is secreted in the culture solution, a supernatant is separated from the cells by methods known in the art after termination of cultivation, and then collected. The separation and purification of the human TRH receptor protein contained in the culture supernatant or the extract thus obtained can be carried out by appropriate combinations of well-known separating and purifying methods. These known separating and purifying methods include methods utilizing a difference in solubility such as salting-out and solvent precipitation, methods mainly utilizing a difference in molecular weight such as dialysis, ultrafiltration, gel filtration and SDS-polyacrylamide gel electrophoresis, methods utilizing a difference in electric charge such as ion-exchange chromatography, methods utilizing specific affinity such as affinity chromatography, methods utilizing a difference in hydrophobicity such as reverse phase high performance liquid chromatography, and methods utilizing a difference in isoelectric point such as isoelectric point electrophoresis.

When the human TRH receptor proteins are obtained in the free form, they can be converted to appropriate salts by known methods or methods based thereon. Conversely, when the receptor proteins are obtained in the salt state, they can be converted to the free forms or other salts by known methods or methods based thereon.

Before or after purification, an appropriate protein modifying enzyme can also be reacted with the human TRH receptor protein produced by a recombinant to arbitrarily modify the protein or to partially eliminate a polypeptide therefrom. The protein modifying enzymes used include trypsin, chymotrypsin, arginyl endopeptidase and protein kinase.

The activity of the human TRH receptor proteins thus obtained can be measured by binding experiments with labeled TRH and enzyme immunoassays using specific antibodies.

Uses for the DNAs coding for the human TRH receptor proteins and said receptor protein of the present invention include (i) acquisition of antibodies and antisera, (ii) construction of expression systems of recombinant receptor proteins, (iii) development of receptor binding assay systems and cell stimulation assay systems using said expression systems and screening of potential compounds for drugs, (iv) execution of drug design based on the comparison of ligands and receptors which are structurally similar to each other, (v) preparation of probes and PCR primers in gene diagnosis, (vi) detection of human TRH or human TRH receptors in vivo and (vii) gene therapy. In particular, the information hitherto obtained suggests that TRH is deeply related to the functions of the central nerve system, etc. Accordingly, elucidation of the structure and properties of the human TRH receptors can contribute to the development of unique drugs acting on these systems. In particular, the human TRH receptor proteins, the receptor fragments or the DNAs of the present invention are derived from humans, so that they are useful as diagnostic compositions or pharmaceutical compositions for human neuropathy (for example, dementia). Furthermore, the TRH receptor agonists or antagonists specific to humans can be screened by the receptor binding assay systems using the expression systems of the recombinant receptor proteins, and said agonists and antagonists can be used as pharmaceutical compositions for neuropathy (for example, dementia). The use of the proteins, the receptor fragments or the DNAs of the present invention will be described in detail below.

(1) TRH is known to have the function of secreting acetylcholine, a neurotransmitter of the central nerve system, in vivo. Accordingly, decreased or injured TRH receptors in vivo conceivably results in a reduction in the function of the central nerve system, which causes central neuropathy such as dementia.

Then, when a patient who can not exhibit the effect of TRH sufficiently in vivo, because of decreased TRH receptors in central nerve cells, such as a patient with dementia or Alzheimer's disease, is discovered, the expression amount of the TRH receptors in the central nerve cells of the patient can be increased to exhibit the function of TRH sufficiently, by (a) inserting the DNA coding for the human TRH receptor protein of the present invention into the patient to express it, or (b) inserting the DNA coding for the human TRH receptor protein of the present invention into central nerve cells to express it, followed by implantation of the central nerve cells in the patient. The DNAs of the present invention can be therefore used as safe, low toxic acetylcholine liberators, and further as safe, low toxic preventive-therapeutic compositions for neuropathy (for example, preventive-pharmaceutical compositions for vertebrocerebellum degeneration, disorder of consciousness, schizophrenia, depression, dementia and Alzheimer's disease). The DNAs of the present invention can be given as the above-mentioned pharmaceutical compositions according to methods known in the art. For example, they can be given orally as tablets coated with sugar as required, capsules, elixirs and microcapsules, or parenterally in the form of injections such as sterile solutions or suspensions with water or with pharmaceutically acceptable solutions other than water. For example, the DNAs of the present invention can be mixed with carriers, flavoring agents, excipients, vehicles, preservatives, stabilizing agents, binders, etc. in the form of unit dosage required for generally accepted pharmaceutical practice to prepare preparations. The amount of active ingredients in these preparations is adjusted so as to obtain appropriate doses within specified ranges.

Additives which can be mixed with tablets, capsules, etc. include, for example, binders such as gelatin, corn starch, tragacanth and gum arabic; excipients such as crystalline cellulose; swelling agents such as corn starch, gelatin and alginic acid; lubricants such as magnesium stearate; sweeteners such as sucrose, lactose and saccharine; and flavoring agents such as peppermint, acamono oil and cherry. When the preparation unit is in the capsule form, liquid carriers such as fat and oil may further be added to materials of the above-mentioned types. Sterile compositions for injection can be formulated according to usual pharmaceutical practice such as dissolution or suspension of active substances and naturally occurring vegetable oils such as sesame oil and coconut oil in vehicles such as water for injection. Aqueous solutions for injection include physiological saline and isotonic solutions containing glucose or other adjuvants (for example, D-sorbitol, D-mannitol and sodium chloride), and may be used in combination with appropriate solubilizing adjuvants such as alcohols (for example, ethanol), polyalcohols (for example, polypropylene glycol and polyethylene glycol) and nonionic detergents (for example, Polysolvate 80 (TM) and HCO-50). Oily solutions include sesame oil and soybean oil, and may be used in combination with solubilizing adjuvants such as benzyl benzoate, benzyl alcohol, etc. The preparations may further contain buffers (for example, phosphate buffer and sodium acetate buffer), soothing agents (for example, benzalkonium chloride and procaine hydrochloride), stabilizing agents (for example, human serum albumin and polyethylene glycol), preservatives (for example, benzyl alcohol and phenol), antioxidants, etc. The injections thus prepared are usually filled into appropriate ampuls. The preparations thus obtained are safe and low toxic, so that they can be given to, for example, warm-blooded animals (such as rats, rabbits, sheep, pigs, cattle, cats, dogs, monkeys, humans and so on). Although the dosage of the DNAs varies depending upon the symptom, the oral dosage is generally about 0.1 to 100 mg per day, preferably 1.0 to 50 mg, and more preferably 1.0 to 20 mg, for adults (taken as 60 kg). When the preparations are parenterally given, the dose varies depending upon the object to which the preparations are given, the organ to which they are given, the symptom, the route of administration, etc. For example, when the preparations are given in the injection form, it is advantageous that they are intravenously injected in a dosage of about 0.01 to 30 mg per day, preferably 0.1 to 20 mg, and more preferably 0.1 to 10 mg, for adults (taken as 60 kg). They can also be given to other animals in an amount converted to a value per 60 kg.

(2) The human TRH receptor proteins or the salts thereof, or the receptor fragments thereof or the salts thereof of the present invention have binding activity to TRH, so that the TRH concentration in vivo can be determined with high sensitivity. They can be therefore effectively used as diagnostic compositions for neuropathy such as dementia. When the human TRH receptor proteins or the salts thereof, or the receptor fragments thereof or the salts thereof of the present invention are used as diagnostic compositions which can determine the TRH concentration in test samples, they can be used, for example, in combination with competitive assays. Namely, the test samples are brought into contact with the human TRH receptor proteins or the salts thereof, or the receptor fragments thereof or the salts thereof of the present invention to determine the concentration of TRH contained in the test samples, whereby neuropathy such as vertebrocerebellum degeneration, disorder of consciousness, schizophrenia, depression, dementia can be diagnosed. Specifically, for example, the methods described in the following (i) or (ii), or methods based thereon can be used:

(i) *Radioimmunoassay,* edited by H. Irie, Kodansha (1974), and (ii) *Radioimmunoassay (second series),* edited by H. Irie, Kodansha (1979)

(3) Compounds that can antagonize binding of TRH to the human TRH receptors (for example, peptides, proteins, non-peptide compounds, synthetic compounds and fermentation products) or salts thereof can be screened by using the human TRH receptor proteins or the salts thereof, or the receptor fragments thereof or the salts thereof of the present invention, or by constructing expression systems of recombinant receptor proteins and employing receptor binding assay systems using said expression systems. Such compounds include compounds having cell stimulating activity (for example, acetylcholine releasing activity, arachidonic acid releasing activity, mobilization of $Ca^{2+}$ in the cells, hyper metabolism of inositole phosphate, activation of adenylate cyclase and activation of c-fos etc.) through the TRH receptors (that is, by binding to the TRH receptors) like TRH (so-called TRH receptor agonists), and compounds having no cell stimulating activity (so-called TRH receptor antagonists). That is to say, the present invention provides:

(i) A method for screening a compound that can antagonize binding of TRH to a human TRH receptor, or a salt thereof, comprising comparing the amounts of a labeled ligand bound to a human receptor protein capable of binding TRH or a salt thereof, or a receptor fragment containing a sufficient portion of a human receptor protein to bind TRH or a salt thereof of the present invention in the two cases of (a) and (b);

(a) contacting the labeled ligand with the receptor protein or the salt thereof, or with the receptor fragment or the salt thereof, (b) contacting the labeled ligand and a test compound with the receptor protein or the salt thereof, or with the receptor fragment or the salt thereof;

(ii) A method for screening a compound that can antagonize binding of TRH to a human TRH receptor comprising comparing the amounts of a labeled ligand bound to a cell or a cell membrane fraction which contains a human TRH receptor protein capable of binding TRH in the two cases of (a) and (b);

(a) contacting the labeled ligand with the cell or the cell memebrane fraction, (b) contacting the labeled ligand and a test compound with the cell or the cell memebrane fraction;

(iii) A method for screening a compound that can antagonize binding of TRH to a human TRH receptor, or a salt thereof, comprising comparing the amounts of a labeled ligand bound to a receptor protein or the salt thereof in the two cases of (a) and (b);

(a) contacting the labeled ligand with the TRH receptor protein which was expressed on a cell membrane by cultivating the transformant comprising the DNA which codes for human TRH receptor protein of the present invention, (b) contacting the labeled ligand and a test compound with the TRH receptor protein which was expressed on a cell membrane by cultivating the transformant comprising the DNA which codes for human TRH receptor protein of the present invention;

(iv) A method for screening a compound that can antagonize binding of TRH to a human TRH receptor, or a salt thereof, comprising comparing cell stimulating activity (for example, acetylcholine releasing activity, arachidonic acid releasing activity, mobilization of $Ca^{2+}$ in the cells, hyper metabolism of inositole phosphate, activation of adenylate cyclase and activation of c-fos etc.) through the TRH receptor (that is, by binding to the TRH receptor) in the two cases of (a) and (b);

(a) contacting a TRH receptor-activating compound (for example, TRH, a TRH analog compound, etc.) with a cell which comprises the receptor protein of the present invention, (b) contacting a TRH receptor-activating compound and a test compound with a cell which comprises the receptor protein of the present invention; and (v) A method for screening a compound that can antagonize binding of TRH to a human TRH receptor, or a salt thereof, comprising comparing cell stimulating activity (for example, acetylcholine releasing activity, arachidonic acid releasing activity, mobilization of $Ca^{2+}$ in the cells, hyper metabolism of inositole phosphate, activation of adenylate cyclase and activation of c-fos etc.) through the TRH receptor (that is, by binding to the TRH receptor) in the two cases of (a) and (b);

(a) contacting a TRH receptor-activating compound (for example, TRH, a TRH analog compound, etc.) with the TRH receptor protein which was expressed on a cell membrane by cultivating the transformant comprising the DNA which codes for human TRH receptor protein of the present invention, (b) contacting a TRH receptor-activating compound and a test compound with the TRH receptor protein which was expressed on a cell membrane by cultivating the transformant comprising the DNA which codes for human TRH receptor protein of the present invention.

As mentioned above, the method for screening of this invention is conducted by determining and comparing the amount of a labeled ligand (ex. [$^3$H]TRH) bound to a human TRH receptor in case of (a) contacting the labeled ligand with the human TRH receptor, with the amount of a labeled ligand bound to a human TRH receptor in case of (b) contacting the labeled ligand and a test compound with the human TRH receptor.

When the human TRH-receptor agonists or antagonists were screened prior to acquisition of the human TRH receptor proteins, potential compounds were first obtained by use of rat TRH receptors, etc. (first screening), and thereafter a test for confirming whether the potential compounds actually antagonized binding of TRH to the human TRH receptors or not (second screening) was required.

However, as is apparent from Examples 5 and 6 described below, the use of the receptor proteins of the present invention makes the first screening unnecessary, resulting in efficient screening of compounds that can antagonize binding of TRH to the human TRH receptors. Further, as is apparent from Example 7, it can be evaluated whether a compound screened is a TRH receptor agonist or a TRH receptor antagonist. In particular, the TRH receptor agonists obtained by such screening methods of the present invention have acetylcholine releasing activity and arachidonic acid releasing activity, so that they are useful as drugs for improving the function of the central nerve system (for example, pharmaceutical compositions for vertebrocerebellum degeneration, disorder of consciousness, schizophrenia, depression, dementia and Alzheimer's disease).

The screening methods of the present invention will be described in detail below.

The human TRH receptor proteins used for screening are preferably membrane fractions of the human organs, although they may be any as long as they contain the human TRH receptor proteins or the receptor fragments thereof. However, it is very difficult to obtain the human-derived organs, so that human TRH receptor proteins expressed in large amounts by use of recombinants are suitable as the proteins used for screening.

The above-mentioned methods are used for the production of the human TRH receptor proteins, and can be performed by expressing DNAs coding for said proteins in mammal cells or insect cells. Complementary DNAs are used as the DNA fragments coding desired portions, but the DNA fragments are not necessarily limited thereto. For example, gene fragments or synthetic DNAs may be used. In order to introduce the DNA fragments coding for the human TRH receptor proteins into host animal cells and express them efficiently, it is preferred that said DNA fragments are ligated downstream from polyhedrin promoters of insect nuclear polyhedrosis viruses (NPVs) belonging to Baculoviridae, SV40-derived promoters, retrovirus promoters (for example, HTLV-1 LTR-derived SRα promoter), metallothionein promoters, heat shock promoters, cytomegalovirus promoters, etc. The amount and quality of the expressed receptor can be examined by methods known per se in the art, for example, the method described in P. Nambi et al. *J. Biol. Chem.*, 267, 19555–19559 (1992).

In the screening methods of the present invention, therefore, the receptor proteins containing the human TRH receptor proteins or the receptor fragments thereof may be the human TRH receptor proteins or the receptor fragments thereof purified according to methods known per se in the art. Further, either cells containing the receptor proteins or membrane fractions of cells containing the receptor proteins may be used.

When assaying TRH receptor activity in animal tissues such as rat, porcine, bovine and human, a binding assay using intact cells is usually difficult and cell membrane fragments must be prepared for the assay. However, the present invention can conduct a binding assay using intact cells or fixed cells without preparing the cell membrane fragments, by expression of a cDNA of human TRH receptor in cells that can cultivate the cDNA in vitro.

In the screening methods of the present invention, when the cells containing the human TRH receptor proteins are used, said cells are preferably fixed by glutaraldehyde or formalin. The fixing methods can be conducted according to methods known per se in the art.

The cells containing the human TRH receptor proteins means host cells in which the human TRH receptor proteins are expressed. Said host cells include *E. coli, Bacillus subtilis,* yeast, insect cells and animal cells.

The membrane fractions means fractions in which cell membranes obtained by methods known Per se in the art after cell disruption are contained in large amounts. Methods for disrupting the cells include the method of crushing the cells with a Potter-Elvehjem type homogenizer, disruption with a Worling blender or a Polytron homogenizer (Kinematica), disruption by ultrasonication, and disruption by allowing the cells to jet through a fine nozzle under pressing with a French press, etc. Fractionating methods utilizing centrifugal force such as differential centrifugation and density gradient centrifugation are mainly used for fractionation of the cell membranes. For example, a cell disrupted solution is centrifuged at a low speed (500 to 3000 rpm) for a short period of time (usually about 1 to 10 minutes), and the supernatant is further centrifuged at a high speed (15000 to 30000 rpm), usually for 30 minutes to 2 hours. The resulting precipitate is taken as the membrane fraction. In said membrane fraction, the expressed TRH receptor proteins and membrane components such as cell-derived phospholipids, membrane proteins and so on are contained in large amounts.

The amount of the TRH receptor proteins in the cells or the membrane fractions containing the TRH receptor proteins is preferably $10^3$ to $10^8$ molecules per cell, and suitably $10^5$ to $10^7$ molecules per cell. A greater expression amount results in higher TRH binding activity per membrane fraction (specific activity). That is, human TRH receptor fragments of the invention bind to TRH. Not only construction of a high sensitive screening system becomes possible, but also a large amount of samples can be measured in the same lot.

Binding affinity of cells comprising human TRH receptor protein of the present invention on TRH receptor is about $5.0 \times 10^{-8}$M to about $5.0 \times 10^{-11}$M, preferably about $5.0 \times 10^{-9}$M to about $5.0 \times 10^{-10}$M.

In order to screen compounds that can antagonize the binding of TRH to a human TRH receptor, an appropriate human TRH receptor fraction and a labeled ligand are required. Desirable examples of the human TRH receptor fractions include natural human TRH receptor fractions and recombinant human TRH receptor fractions equivalent thereto in activity, wherein the activity shows ligand-binding activity, etc. As the labeled ligands, labeled TRH and labeled TRH analog compounds are used. For example, TRH labeled with [$^3$H] (du Pont), etc. are commercially available. They can therefore be utilized.

Specifically, when the compounds that can antagonize the binding of TRH to the human TRH receptor is screened, cells or cell membrane fractions containing the human TRH receptor protein are first suspended in a buffer suitable for screening, thereby preparing a receptor sample. The buffer may be any, as long as it is a buffer which does not inhibit the binding of TRH to the receptor, such as phosphate buffer or Tris-HCl buffer having a pH of 4 to 10 (preferably a pH of 6 to 8). For the purpose of decreasing non-specific binding, a detergent such as CHAPS, Tween-20™ (Kao-Atlas), digitonin or deoxycholate may also be added to the buffer. Further, for the purpose of inhibiting decomposition of the receptor or the ligand due to a protease, a protease inhibitor such as PMSF, leupeptin, E-64 (Peptide Laboratory) or pepstatin can also be added. A definite amount (5000 to 500000 cpm) of [$^3$H] TRH is added to 0.01 to 10 ml of the receptor solution, and $10^{-4}$ to $10^{-10}$M test compound, fermentation products, etc. are allowed to coexist at the same time. In order to know the non-specific binding (NSB), a reaction tube to which an unlabeled TRH is added in large excess is prepared. Reaction is conducted at 0° to 50° C., desirably at 4° to 37° C. for 20 minutes to 24 hours, desirably for 30 minutes to 3 hours. After reaction, the reaction product is filtered through a glass fiber filter and washed with an appropriate amount of the same buffer, followed by measurement of [$^3$H] remaining on the glass fiber filter with a liquid scintillator. When the count ($B_0$-NSB) obtained by subtracting NSB from the count ($B_0$) in the absence of an antagonistic substance is taken as 100%, the test compound, the fermentation products, etc. giving a non-specific binding (B-NSB) of 50% or less can be selected as potential materials having antagonistic ability.

The kits of the present invention for screening the compounds that can antagonize the binding of TRH to the human TRH receptors, or the salts thereof, comprise the human TRH receptors or the salts thereof of the present invention, the receptor fragments of the human TRH receptors or the salts thereof, the cells containing the human TRH receptors of the present invention, or the membrane fractions of the cells containing the human TRH receptors of the present invention.

Examples of the kits for screening of the present invention include the following:

1. Reagents for Screening
(i) Buffer for Measurement and Buffer for Washing

Hanks' balanced salt solution (Gibco) supplemented with 0.05% bovine serum albumin (Sigma)

The solution may be sterilized by filtration through a filter having a pore size of 0.45 μm and stored at 4° C., or may be prepared at the time of use.

(ii) Human TRH Receptor Sample

A sample obtained by subculturing 1×10$^5$ CHO cells in which the human TRH receptor protein is expressed to each well of a 12-well plate, and culturing them at 37° C. in an atmosphere of 5% CO$_2$ and 95% air for 2 days (iii) [$^3$H] Labeled TRH

[L-proline-2,3,4,5-$^3$H(N)]-(Pyro)Glu-His-Pro-NH$_2$ (du Pont, NET-577-10 and 20)

This is stored in the aqueous solution state at 4° C. or −20° C., and diluted to 1 μM with the buffer for measurement at the time of use.

(iv) TRH Standard Solution

TRH (Peptide Laboratory) is diluted with PBS containing 0.1% bovine serum albumin (Sigma) to 1 mM, and stored at −20° C.

2. Assays (i) The CHO cells in which the human TRH receptor is expressed, which are cultured on the 12-well tissue culture plate, are washed twice with 1 ml of the buffer for measurement, followed by addition of 490 μl of the buffer for measurement to each well.

(ii) After addition of 10$^{-3}$ to 10$^{-10}$M test compound or 5 μl of an extract of a fermentation product, 5 μl of [$^3$H] labeled TRH is added, followed by reaction for 1 hour at room temperature. In order to examine the non-specific binding, 5 μl of 10$^{-3}$M TRH is added instead of the test compound.

(iii) After removal of the reaction solution, the residue is washed three times with 1 ml of the buffer for washing. [$^3$H] TRH bound to the cells is dissolved in 0.2N NaOH-1% SDS, and the resulting solution is mixed with 4 ml of liquid scintillator A (Wako Pure Chemical Industries).

(iv) [$^3$H] is measured with a liquid scintillation counter, and the percent maximum binding (PMB) is determined from the following equation;

$$PMB = [(B-NSB)/(B_0-NSB)] \times 100$$

PMB: percent maximum binding
B: value when the test compound is added
NSB: non-specific binding
$B_0$: maximum binding The compounds or the salts thereof obtained by use of he screening methods or the kits for screening of the resent invention are compounds that can antagonize the binding of TRH to the TRH receptors, and specifically, compounds having cell stimulating activity through the TRH receptors or salts thereof (TRH receptor agonists) or compounds having no cell stimulating activity (TRH receptor antagonists). Said compounds include peptides, proteins, non-peptide compounds, synthetic compounds and fermentation products. These compounds may be either novel compounds or known compounds.

Binding affinity on human TRH receptor of the compounds that can antagonize binding of TRH to a human TRH receptor, for example, preferably is similar to or more than the binding affinity of TRH on TRH receptor (1.0×10$^{-8}$M). That is about 1.0×10$^{-6}$ to about 1.0×10$^{-10}$M, preferably about 1.0×10$^{-7}$ to about 1.0×10$^{-9}$M.

Examples of the TRH receptor agonists obtained by the screening methods of the present invention include a compound (I) represented by formula (I) or salt thereof:

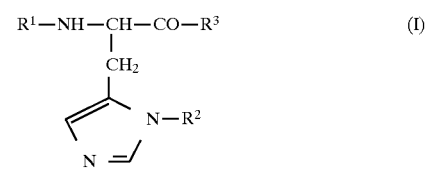

wherein R$^1$ represents a pyroglutamic acid residue (pGlu), a γ-butyrolactone-γ-carbonyl group (Blc), a 2-ketopiperidine-6-carbonyl group (Kpc), a 3-oxoperhydro-1,4-thiazine-5-carbonyl group (Otc) or a glutamic acid residue (Glu); R$^2$ represents a hydrogen atom or a C$_{1-6}$ alkyl group; R$^3$ represents a group indicated by

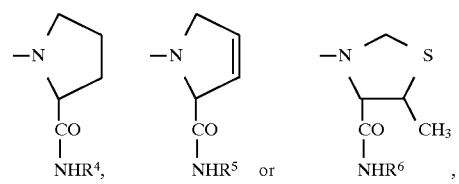

wherein R$^4$, R$^5$ and R$^6$ each represent hydrogen atoms, C$_{1-6}$ alkyl groups or phenyl-C$_{1-3}$ alkyl groups; with the proviso that a compound in which R$^1$ is a pyroglutamic acid residue, R$^2$ is a hydrogen atom, and R$^3$ is

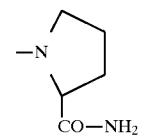

is excluded.

In the above-mentioned compounds represented by formula (I) (hereinafter also referred to as compounds (I)), examples of the C$_{1-6}$ alkyl groups represented by R$^2$, R$^4$, R$^5$ and R$^6$ include methyl, ethyl, n-propyl, i-propyl, n-butyl, i-butyl, tert-butyl, n-pentyl and n-hexyl. C$_{1-4}$ alkyl groups such as methyl, ethyl, n-propyl and n-butyl are preferred among others. Examples of the phenyl-C$_{1-3}$ alkyl groups represented by $R^4$, $R^5$ and $R^6$ include benzyl and phenylethyl. As $R^2$, a hydrogen atom or methyl is preferred. As $R^4$, a hydrogen atom, methyl, butyl or phenylethyl is preferred. As $R^5$, a hydrogen atom is preferred. As $R^6$, a hydrogen atom is preferred. Examples thereof include compounds Nos. 1 to 19 described in Table 2 which are obtained in Example 6 given below.

As the salts of the above-mentioned compounds (I), physiologically acceptable acid addition salts are preferred among others. Examples of such salts include salts with inorganic acids (such as hydrochloric acid, phosphoric acid, hydrobromic acid and sulfuric acid) and salts with organic acids (such as acetic acid, formic acid, propionic acid, fumaric acid, maleic acid, succinic acid, tartaric acid, citric acid, malic acid, oxalic acid, benzoic acid, methanesulfonic acid and benzenesulfonic acid).

The compounds (I) or the salt thereof of the present invention can be produced by known methods or methods based thereon. Further, commercial compounds may be used. For example, compounds Nos. 1 to 4 and 13 to 18 are available from Peninsula, 611 Taylor, Belmont, Calif., U.S.A.

The above-mentioned compounds (I) or the salts thereof have cell stimulating activity through the TRH receptors. Accordingly, the compounds (I) or the salts thereof can be used as acetylcholine releasers or arachidonic acid releasers, and are useful as safe, low toxic preventive-pharmaceutical compositions for neuropathy such as vertebrocerebellum degeneration, disorder of consciousness, schizophrenia, depression, dementia and Alzheimer's disease.

The compounds (I) or the salts thereof can be given as the above-mentioned preparations according to methods known in the art. For example, they can be given orally as tablets coated with sugar as required, capsules, elixirs and microcapsules, or parenterally in the form of injections such as sterile solutions or suspensions with water or with pharmaceutically acceptable solutions other than water. For example, the compounds (I) or the salts thereof can be mixed with carriers, flavoring agents, excipients, vehicles, preservatives, stabilizing agents, binders, etc. in the form of unit dosage required for generally admitted pharmaceutical practice to prepare preparations. The amount of active ingredients in these preparations is adjusted so as to obtain appropriate doses within specified ranges.

Additives which can be mixed with tablets, capsules, etc. include, for example, binders such as gelatin, corn starch, tragacanth and gum arabic; excipients such as crystalline cellulose; swelling agents such as corn starch, gelatin and alginic acid; lubricants such as magnesium stearate; sweeteners such as sucrose, lactose and saccharine; and flavoring agents such as peppermint, acamono oil and cherry. When the preparation unit is in the capsule form, liquid carriers such as fat and oil may further be added to materials of the above-mentioned types. Sterile compositions for injection can be formulated according to usual pharmaceutical practice such as dissolution or suspension of active substances and naturally occurring vegetable oils such as sesame oil and coconut oil in vehicles such as water for injection.

Aqueous solutions for injection include physiological saline and isotonic solutions containing glucose or other adjuvants (for example, D-sorbitol, D-mannitol and sodium chloride), and may be used in combination with appropriate solubilizing adjuvants such as alcohols (for example, ethanol), polyalcohols (for example, polypropylene glycol and polyethylene glycol) and nonionic detergents (for example, Polysolvate 80 (TM) and HCO-50). Oily solutions include sesame oil and soybean oil, and may be used in combination with solubilizing adjuvants such as benzyl benzoate, benzyl alcohol, etc. The preparations may further contain buffers (for example, phosphate buffer and odium acetate buffer), soothing agents (for example, benzalkonium chloride and procaine hydrochloride), stabilizing agents (for example, human serum albumin and polyethylene glycol), preservatives (for example, benzyl alcohol and phenol), antioxidants, etc. The injections thus prepared are usually filled into appropriate ampuls. The preparations thus obtained are safe and low toxic, so that they can be given to, for example, warm-blooded animals (such as rats, rabbits, sheep, pigs, cattle, cats, dogs, monkeys, humans and so on). Although the dosage of the compounds (I) or the salts thereof varies depending upon the symptom, the oral dosage is generally about 0.1 to 100 mg per day, preferably 1.0 to 50 mg, and more preferably 1.0 to 20 mg, for adults (taken as 60 kg). When the preparations are parenterally given, the dose varies depending upon the object to which the preparations are given, the organ to which they are given, the symptom, the route of administration, etc. For example, when the preparations are given in the injection form, it is advantageous that they are intravenously injected in a dosage of about 0.01 to 30 mg per day, preferably 0.1 to 20 mg, and more preferably 0.1 to 10 mg, for adults (taken as 60 kg). They can also be given to other animals in an amount converted to a value per 60 kg.

Antibodies (for example, polyclonal antibodies, monoclonal antibodies) or antisera to the human TRH receptor proteins or the salts thereof, or the receptor fragments of the human TRH receptor proteins of the present invention can be produced according to methods known per se in the art using the human TRH receptor proteins or the salts thereof, or the receptor fragments of the human TRH receptor proteins of the present invention as antigens.

Monoclonal antibodies, for example, can be prepared according to the following method:

(a) Preparation of Monoclonal Antibody-producing cells

Human TRH receptor protein or a salt thereof or a partial peptide of human TRH receptor protein or a salt thereof (hereinafter, sometimes referred to as human TRH receptor) is given alone or together with carriers and diluents to warm-blooded animals at antibody-producible sites. When human TRH receptor protein is given, Freund's complete adjuvant or Freund's incomplete adjuvant may be given to enhance antibody producing ability. The dosing is usually carried out once every 2 to 6 weeks, totally 2 to 10 times. The warm-blooded animals include, for example, monkeys, rabbits, dogs, guinea pigs, mice, rats, sheep, goat and chickens. For preparation of the monoclonal antibodies, mice and rats are preferably used.

In preparing the monoclonal antibodies, individuals showing a high antibody titer are selected from the warm-blooded animals, for example, mice, immunized with the antigens. After 2 to 5 days from the final immunization, the spleens or the lymph nodes are collected therefrom, and antibody-producing cells contained therein are fused with myeloma cells, whereby anti-human TRH receptor monoclonal antibody-producing hybridomas can be prepared. The anti-human TRH receptor antibody titer in the serum is determined, for example, by reacting a labeled human TRH receptor described below with an anti-serum, and then assaying the activity of an labeling agent bound to the antibody. The fusing procedure can be conducted according to methods known in the art, for example, the method of Köhler and Milstein [*Nature*, 256, 495 (1975)]. Fusion accelerators, including polyethylene glycol (PEG) and Sendai virus, may be used. In particular, PEG is preferably used.

Examples of the myeloma cells include NS-1, P3U1, SP2/0 and AP-1, and P3U1 is preferably used. The ratio of the antibody-producing cells (spleen cells) to be used to the myeloma cells is preferably about 1:1 to 20:1. PEG (preferably PEG 1,000 to PEG 6,000) can be added in a concentration of about 10 to 80%, followed by incubation at 20° to 40° C., preferably 30° to 37° C., for 1 to 10 minutes, thereby effectively performing cell fusion.

Various methods can be used for screening the anti-human TRH receptor antibody-producing hybridomas. Examples of such methods include a method comprising adding a hybridoma culture supernatant to a solid phase (for example, a microplate) by which a human TRH receptor is allowed to be adsorbed directly or together with a carrier, and then, adding an anti-immunoglobulin antibody (when a mouse cell is used for cell fusion, an anti-mouse immunoglobulin antibody is used) or protein A labeled with a radioactive material or an enzyme to detect an anti-human TRH receptor monoclonal antibody bound to the solid phase; and a method comprising adding a hybridoma culture supernatant to a solid phase by which an anti-immunoglobulin antibody or protein A is allowed to be adsorbed, and adding a human TRH receptor labeled with a radioactive material or an enzyme to detect an anti-human TRH receptor monoclonal antibody bound to the solid phase.

Selection of the anti-human TRH receptor monoclonal antibody can be conducted in a method per se known in the art or a similar method. Medium for animal cells supplemented with HAT (hypoxanthine, aminopterin and thymidine) is usually used. Mediums for selection and breeding of the anti-human TRH receptor monoclonal antibody may be any as long as hybridomas can grow in the medium. For example, RPMI 1640 supplemented with 1–20%, preferably 10–20% fetal calf serum, GIT medium (Wako Pure Chemical Co. Ltd., Japan) supplemented with 1–10% fetal calf serum or serum-free medium for culture of hybridomas(SFM-101, Nissui Seiyaku Co. Ltd., Japan) can be used. The cultivation temperature is usually 20° to 40° C., preferably about 37° C. The cultivation time is usually 5 days to 3 weeks, preferably 1 week to 2 weeks. Cultivation is usually conducted under 5% $CO_2$. Antibody titer of the hybridoma culture supernatant can be assayed in a manner similar to the above-mentioned assay of the anti-human TRH receptor monoclonal antibody in the anti-serum.

(b) Purification of Monoclonal Antibodies

Separation and purification of the anti-human TRH receptor monoclonal antibodies are carried out similarly to usual separation and purification of polyclonal antibodies according to separating and purifying methods of immunoglobulin [for example, salt precipitation, alcohol precipitation, isoelectric precipitation, electrophoresis, adsorption and desorption with ion exchange materials (for example, DEAE), ultracentrifugation, gel filtration and specific purification in which only the antibodies are collected with active adsorbing agents such as antigen-binding solid phases, protein A and protein G].

The antibody of the present invention thus obtained which specifically recognize the human TRH receptor, and therefore used for determination of the human TRH receptor in a test solution, particularly determination by the sandwich immunoassay.

Namely, the present invention provides:

(1) a method for determining a human TRH receptor in a test solution which comprises competitively reacting an antibody of the present invention to the human TRH receptor with the test solution and a labeled human TRH receptor, and measuring the ratio of the labeled human TRH receptor bound to said antibody;

(2) a method for determining a human TRH receptor in a test solution which comprises reacting an antibody to a human TRH receptor insolubilized on a carrier, a labeled antibody to a TRH receptor and the test solution with one another at the same time or successively, and then, measuring the activity of a labeling agent on the carrier, in the method, one of the antibodies recognizes N-terminal side of the human TRH receptor and the other one reacts to C-terminal side of the human TRH receptor.

The monoclonal antibodies of the present invention capable of recognizing the human TRH receptors (hereinafter sometimes referred to as anti-human TRH receptor antibody) can assay human TRH receptor, and the detection by tissue staining of the human TRH receptors can be conducted. For these purposes, either the antibodies themselves or F(ab')$_2$, Fab' or Fab fractions of the antibody molecules may be used. The measuring methods using the antibodies of the present invention are not particularly limited. Any measuring method may be used, as long as the amount of the antibodies, the antigens or the antibody-antigen complexes corresponding to the amount of the antigens (for example, the amount of the human TRH receptors) in solutions to be measured is detected by chemical or physical means, and calculated from standard curves prepared by the use of standard solutions containing the antigens in known amounts. For example, nephelometry, a competitive method, an immunometric method and a sandwich method are suitably used. With respect to sensitivity and specificity, it is particularly preferred to use the sandwich method described below.

In measuring methods using labeling substances, radioisotopes, enzymes, fluorescent substances, luminous substances, etc. are used as labelling agents. Examples of the radioisotopes include 125I, $^{131}$I, $^{3}$H and $^{14}$C. As the above-mentioned enzymes, it is preferred that they are stable and have a high specific activity. Examples thereof include β-galactosidase, β-glucosidase, alkaline phosphatase, peroxidase and malate dehydrogenase. Examples of the fluorescent substances include fluorescamine and fluorescein isothiocyanate. The luminous substances include, for example, luminol, luminol derivatives, luciferin and lucigenin. Further, biotin-avidin systems can also be used for binding of the antibodies or the human TRH receptors with the labeling agents.

When the antigens or the antibodies are insolubilized, either physical adsorption or chemical binding usually used for insolubilization or fixation of proteins or enzymes may be employed. Examples of the carriers include insoluble polysaccharides such as agarose, dextran and cellulose, synthetic resins such as polystyrene, polyacrylamide and silicone polymers, and glass.

In the sandwich method, the test solutions are reacted with the insolubilized anti-human TRH receptor antibodies (the first reaction), further, the labeled anti-human TRH receptor antibodies are reacted (the second reaction), and then, the activity of the labeling agents on the insolubilized carriers is assayed, whereby the amount of the human TRH receptors in the test solutions can be determined. The first reaction and the second reaction may be conducted in reverse order, concurrently or sequentially. The labeling agents and the insolubilizing methods can be used in accordance with those described above. Further, in the immunoassays by the sandwich method, the antibodies used as the antibodies for solid phases or the antibodies to be labeled are not necessarily of one kind, but two or more kinds of antibodies may be used as mixtures for the purpose of enhancing the measuring sensitivity, etc.

In the methods of the present invention for measuring the human TRH receptors by the sandwich methods, the anti-human TRH receptor antibodies used in the first reaction are preferably different from those used in the second reaction in sites at which the antibodies bound to the human TRH receptors. For example, when the antibody used in the second reaction recognizes the C-terminal side of the human TRH receptor, the antibody used in the first reaction preferably recognizes other than the C-terminal side (for example, the N-terminal side).

The monoclonal antibodies of the present invention can also be used in assay systems other than the sandwich method, for example, a competitive method, an immunometric method and nephelometry. In the competitive method, antigens in test solutions and labeled antigens are competitively reacted with the antibodies, followed by separation of the unreacted labeled antigens (F) from the labeled antigens (B) bound to the antibodies (B/F separation). Then, the labeled amount of either B or F is measured to determine the amount of the antigens in the test solutions. This method includes a liquid phase method in which soluble antibodies are used as the antibodies, and polyethylene glycol and the second antibodies to the above-mentioned antibodies are used for B/F separation, and a solidifying method in which solidified antibodies are used as the first antibodies, or soluble antibodies are used as the first antibodies and solidified antibodies are used as the second antibodies.

In the immunometric method, antigens in test solutions and solidified antigens are competitively reacted with a specified amount of labeled antibodies, followed by separation of solid phases from liquid phases, or antigens in test solutions are reacted with excess labeled antibodies, and then, solidified antigens are added to allow the unreacted labeled antibodies to bind to solid phases, followed by separation of the solid phases from liquid phases. Then, the labeled amount of either phases is measured to determine the amount of the antigens in the test solutions.

In the nephelometry, the amount of insoluble precipitates produced as a result of antigen-antibody reaction in gels or solutions is measured. Even when the amount of antigens in test solutions is slight, and the precipitates are obtained only in small amounts, laser nephelometry utilizing laser scattering is suitably used.

When these immunological assays are applied to the present invention, particular conditions and operations are not required to be established. Usual technical consideration of those skilled in the art may be added to ordinary conditions and operations in the respective assays to construct assay systems of the human TRH receptors. Details of these general technical means can be referred to reviews and books [for example, *Radioimmunoassays* edited by H. Irie (published by Kodansha in 1974), *Radioimmunoassays, second series,* edited by H. Irie (published by Kodansha in 1979), *KOSO MENEKI SOKUTEIHO(Enzyme Immunoassays*), edited by E. Ishikawa et al. (published by Igaku Shoin in 1978), *KOSO MENEKI SOKUTEIHO (Enzyme Immunoassays*) (*second edition*), edited by E. Ishikawa et al. (published by Igaku Shoin in 1982), *KOSO MENEKI SOKUTEIHO(Enzyme Immunoassays*) (*third edition*), edited by E. Ishikawa et al. (published by Igaku Shoin in 1987), *Methods in ENZYMOLOGY,* Vol. 70 (Immunochemical Techniques (Part A) published by Academic Press, ibid., Vol. 73 (Immunochemical Techniques (Part B), ibid., Vol. 74 (Immunochemical Techniques (Part C), ibid., Vol. 84 (Immunochemical Techniques (Part D: Selected Immunoassays), ibid., Vol. 92 (Immunochemical Techniques (Part E: Monoclonal Antibodies and General Immunoassay Methods), and ibid., Vol. 121 (Immunochemical Techniques (Part I: Hybridoma Technology and Monoclonal Antibodies)].

As described above, the human TRH receptor antibodies of the present invention can determine the human TRH receptors with a high sensitivity.

The antibodies of the present invention bind to human TRH receptor protein or fragments thereof with selectivity, and preferably antagonize binding of TRH to human TRH receptor protein.

When nucleotides, amino acids and so on are indicated by abbreviations in the specification and drawings, the abbreviations adopted by the IUPAC-IUB Commission on Biochemical Nomenclature or commonly used in the art are employed. For example, the following abbreviations are used. When the amino acids are capable of existing as optical isomers, it is understood that the L-forms are represented unless otherwise specified.

DNA: Deoxyribonucleic acid
cDNA: Complementary deoxyribonucleic acid
A: Adenine
T: Thymine
G: Guanine
C: Cytosine
RNA: Ribonucleic acid
mRNA: Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediaminetetraacetic acid
SDS: Sodium dodecyl sulfate
EIA: Enzyme immunoassay
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine
NVal: Norvaline
pGlu: Pyroglutamic acid
Blc: γ-Butyrolactone-γ-carbonyl group
Kpc: 2-Ketopiperidine-6-carbonyl group
Otc: 3-Oxoperhydro-1,4-thiazine-5-carbonyl group Me: Methyl group Et: Ethyl group Bu: Butyl group Ph: Phenyl group TC: Thiazolidine-4(R)-carboxyamido group In the human receptor proteins of the present invention, the amino acid sequences thereof may be partially modified (addition, elimination or substitution with other amino acids).

Transformant *Escherichia coli* MV1184/phTRHR316 and transformant *E. coli* MV1184/phTRHR919 each obtained in Example 1 (3) given below were deposited with the Institute for Fermentation, Osaka, Japan (IFO) under the accession numbers IFO 15522 and IFO 15523, respectively, on Aug. 4, 1993, and deposited with the National Institute of Bioscience and Human-technology (NIBH), the Agency of Industrial Science and Technology, the Ministry of International Trade and Industry, Japan, under the accession numbers FERM BP-4380 and FERM BP-4381, respectively, on Aug. 6, 1993.

All documents cited herein are incorporated herein by reference.

The present invention will be described in more detail through the following examples. It is understood of course that they are not intended to limit the scope of the invention.

[EXAMPLE 1]

Screening of Human TRH Receptor Genomic DNA and Sequence Analysis (1) Preparation of Probe A poly(A)+ RNA fraction was prepared from rat pituitary tumor cells GH$_3$ by use of a mRNA isolation kit (Invirogen). Then, a random DNA hexamer (BRL) was added thereto as a primer, and complementary DNA was synthesized by use of a reverse transcriptase of the Moloney's leukemia virus (BRL). Then, based on the nucleotide sequence of rat TRH receptor cDNA already known, the following synthetic DNA primers containing restriction enzyme sequences of HindIII or XbaI at both ends thereof were synthesized.

(i) 5'-TCTAAAGCTTGAAGATGGAGAATG-AAACCGTCAGTGA-3' (SEQ ID NO: 4 in the sequence listing)

(ii) 5'-GTCTTCTAGAAGTTCATATTTTCTCC-TGTTTGGCAGA-3' (SEQ ID NO: 5 in the sequence listing)

Using the above-mentioned primers, and using the complementary DNA prepared above as a template, polymerase chain reaction (PCR) was conducted [R. K. Sakai et al., *Science*, 239, 487–491 (1988)]. The reaction solution was subjected to agarose gel electrophoresis, followed by staining with ethidium bromide. As a result, a band was observed in the vicinity of 1.3 kbp. DNA was therefore extracted therefrom, and cleaved with HindIII and XbaI (Takara), followed by subcloning to plasmid pUC118 (Takara). The whole nucleotide sequence of the subcloned DNA fragment was determined, resulting in approximately complete agreement with the sequence of known rat TRH receptor cDNA. In FIG. 5, amino acid residues which agree with each other between the human sequence (h) and the rat sequence (r) are indicated by asterisks (*). This DNA fragment was allowed to entrap [$^{32}$P] dCTP (du Pont) by use of a random prime DNA labeling kit (Amersham), thereby labeling the DNA fragment, and the labeled DNA fragment was used as a probe.

(2) Screening of Human Genomic DNA Library

As a human genomic DNA library, a library using EMBL-3 phage vector (Clontech) was employed. 2×10$^6$ pfu (plaque forming unit) of the human genomic DNA library was mixed with magnesium sulfate-treated *E. coli* K803, and incubated at 37° C. for 15 minutes. Then, 0.5% agarose (Pharmacia) LB was added thereto, followed by seeding on a 1.5% agar (Wako Pure Chemical Industries) LB plate. A nitrocellulose filter was placed on the plate on which a plaque is formed, and the plaque was transferred onto the filter. After denaturation of this filter by alkali treatment, the DNA was fixed by heating at 80° C. for 3 hours. This filter was incubated overnight with the probe labeled above in 0.5M phosphate buffer (pH 7.2) containing 1 mM EDTA, 1% bovine serum albumin (Sigma) and 7% SDS to hybridize it [G. M. Church and Gilbert, *Proc. Natl. Acad. Sci. U.S.A.*, 81, 1991–1995 (1984)]. Washing was carried out with 2× SSC, 0.1% SDS at 50° C. for 1 hour, and then, autoradiography was conducted at −80° C. to detect hybridized plaques.

(3) DNA Sequence Analysis

By this screening, the hybridization signal was observed in 20 independent plaques. Of these, 6 clones were separated as singleplaques. DNAs were prepared from these 6 clones, and digested with HindIII. After agarose gel electrophoresis, analysis was conducted by the Southern blotting technique using the same probe as used in screening. As a result, two kinds of clones were observed to one of which the probe hybridizes at a band of about 2 kbp, and to the other of which the probe hybridizes at a band of about 1 kbp. From the 6 isolated phage clones, one clone giving a band of about 1 kbp in the HindIII-digested products as a result of the Southern blots in (2) mentioned above (λhTRHR9) and one clone giving a band of about 2 kbp (λhTRHR3) were selected. The HindIII fragments having a size for hybridization were subcloned to the HindIII site of plasmid pUC119, and then, *E. coli* MV1184 was transformed with this plasmid to obtain transformants *E. coli* MV1184/phTRHR316 (IFO 15522, FERM BP-4380) and *E. coli* MV1184/phTRHR919 (IFO 15523, FERM BP-4381). Based on the method of P. C. Yanish, et al. (*Gene*, 33, 103–119), these plasmids were further cleaved stepwise by exonuclease III and exonuclease VII, followed by self cyclization to prepare template plasmids for sequence analysis. Further, unnecessary portions were removed utilizing cleavage sites with restriction enzymes existing in the HindIII fragments inserted into pTRHR316 and pTRHR919, respectively, or necessary fragments were subcloned to prepare template plasmids for sequence analysis. For sequence determination, a 370A DNA sequencer (Applied Biosystems) was used, and for data analysis, a DNASIS (Hitachi Software Engineering) was used.

A nucleotide sequence encoded by phTRHR919 is shown in FIG. 2, and a nucleotide sequence encoded by phTRHR316 is shown in FIG. 3. A nucleotide sequence in which the nucleotide sequence of the 1st to 801st residues in the nucleotide sequence shown in FIG. 2 is ligated with the nucleotide sequence of the 34th to 460th residues in the nucleotide sequence shown in FIG. 3 corresponds to the nucleotide sequence (SEQ ID NO: 3 in the sequence listing) shown in FIG. 4. The nucleotide sequence of DNA coding for the human TRH receptor protein (SEQ ID NO: 2 in the sequence listing) corresponds to the nucleotide sequence of the 13th to 1206th residues in the nucleotide sequence (SEQ ID NO: 3 in the sequence listing) shown in FIG. 4.

[EXAMPLE 2]

Cloning of Human TRH Receptor cDNA and Sequence Analysis

Based on the sequence of the DNA fragment coding for the genomic-derived TRH receptor protein cloned in Example 1, primer DNAs for PCR were synthesized.

Sense primer:

5'-GCGCAAGCTTCTAAAGATGGAAAACGAG-3' (SEQ ID NO: 6 in the sequence listing)

Antisense primer:

5'-TCTAATTCTAGAATCAACTTTGGCTAAA-3' (SEQ ID NO: 7 in the sequence primer)

Using 1 ng of human pituitary gland-derived cDNA (Quick-Clone™, Clontech) as a template, and using 1 $\mu$M of each of the sense and antisense primers, PCR was conducted. First, to the resulting DNA solution were added 10 $\mu$l of 2 mM dNTP (Takara), 10× buffer for PCR (100 mM Tris-HCl (pH 8.3)), 500 mM KCl, 15 mM MgCl$_2$ and 10 $\mu$l of 0.01% (s/v) gelatin (Takara), and sterilized distilled water was further added thereto to prepare 99 $\mu$l of a reaction solution in all. Then, several drops of mineral oil (Sigma) were added dropwise to this solution, followed by heat denaturation at 95° C. for 5 minutes. Thereafter, the product was annealed at 65° C. for 5 minutes, and further cooled to room temperature. Finally, 1 $\mu$l of 5 U/$\mu$l AmpliTaq™ DNA polymerase (Perkin Elmer) was added to the reaction solution, and PCR reaction was conducted under the conditions that reactions at 94° C. for 1 minute, at 55° C. at 1 minute and at 72° C. for 2 minutes were repeated 35 times, using DNA Thermal Cycler™ 480 (Perkin Elmer).

After the reaction, the PCR product was separated by 1.2% Seakem™ GTG (FMC) agarose gel electrophoresis, followed by detection by staining with ethidium bromide. As a result, a DNA fragment of about 1.2 kb was detected. Further, this PCR product was completely digested with HindIII and XbaI (Takara), and ultrafiltration was performed by use of UFC3HK (Millipore), followed by subcloning to pUC118.

Then, in order to determine the nucleotide sequence of the inserted fragment, the plasmid was modified as follows. First, the plasmid was digested with HindIII and StuI or HincII, followed by cyclization by use of Klenow fragments (Takara). ssDNA prepared from E. coli having the plasmid according to conventional methods was used for determination of the nucleotide sequence. The nucleotide sequence was determined by use of a −21M13 dye primer and an M13 reverse dye primer with a Taq dye primer cycle sequencing kit (Applied Biosystems). Furthermore, in an undecoding region, the nucleotide sequence was determined by use of the following synthetic primer with a Taq DyeDeoxy™ terminator cycle sequencing kit (Applied Biosystems).

5'-CACCGGGTTGATGGCAC-3' (SEQ ID NO: 8 in the sequence listing)

The results revealed that the nucleotide sequence of this inserted fragment agreed with the nucleotide sequence (SEQ ID NO: 2) of a coding region of the human TRH receptor protein deduced from the human genomic. Further, the results described above proved that the protein encoded by the cDNA cloned this time had the amino acid sequence shown in FIG. 4.

[EXAMPLE 3]

Expression of Human TRH Receptor Using Baculoviruse phTRHR316 obtained in Example 1 was cleaved with HindIII, followed by further cleavage with Sau3AI. A fragment containing the nucleotide sequence (exon2) shown in FIG. 3 was ligated with the BamH site of pUC118 to prepare a plasmid into which the nucleotide sequence (exon2) of FIG. 3 was inserted. Then, phTRHR919 was cleaved with HindIII and BspMI to prepare a fragment corresponding to the HindIII-BspMI portion of the nucleotide sequence shown in FIG. 2. In order to ligate the nucleotide sequence (exon1) of FIG. 2 with the nucleotide sequence (exon2) of FIG. 3., the following synthetic linkers (i) and (ii) were synthesized, based on the sequence of the translation frame (open reading frame) previously deduced, namely the nucleotide sequence of SEQ ID NO: 4.

(i) BspMI-Eco0652, 12mer

5'-TCAAGGAAGCAG-3' (SEQ ID NO: 9 in the sequence listing)

(ii) EcoO652-BspMI, 13mer

5'-GTGACCTGCTTCC-3' (SEQ ID NO: 10 in the sequence listing)

The plasmid into which the nucleotide sequence (exon2) of FIG. 3 was inserted was cleaved with HindIII and Eco0652 to remove a sequence corresponding to the intron portion, and then, the translation frame (open reading frame) of the human TRH receptor was constructed on ligation pVC118 together with the HindIII-BspMI fragment and synthetic linkers (i) and (ii).

Figure 8:
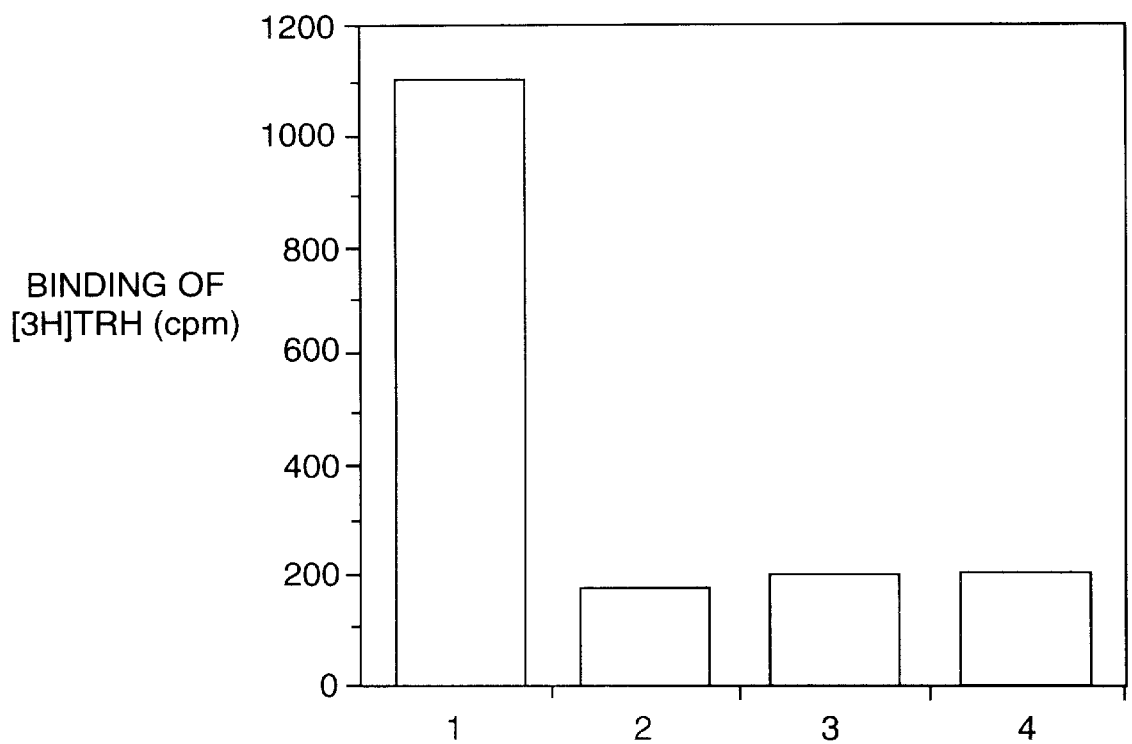
FIG. 8 shows the [$^3$H] TRH binding of a human TRH receptor protein expressed by use of a baculovirus. Columns 1 and 2 on the abscissa indicate Sf9 cells infected with a virus into which human TRH receptor DNAs were introduced, and columns 3 and 4 indicate Sf9 cells infected with no virus. 10 nM of [$^3$H] TRH was added to column 1, 10 nM of [$^3$H] TRH and 10 $\mu$M unlabeled TRH to column 2, 10 nM of [$^3$H] TRH to column 3, and 10 nM of [$^3$H] TRH and 10 $\mu$M unlabeled TRH to column 4. The numbers on the ordinate indicate the [$^3$H] TRH binding (cpm) of the respective cells.

The plasmid having the translation frame (open reading frame) of the human TRH receptor was cleaved with HindIII, and a BamHI linker was added thereto. Further, cleavage with SmaI and addition of a HindIII linker were performed. BamHI and HindIII sites were introduced into both ends of the translation frame (open reading frame) of the human TRH receptor, respectively, by this procedure. The DNA having the BamHI and HindIII sites at both the ends thereof, respectively, was ligated with BglII-HindIII sites of pBlueBacIII to obtain a transfer plasmid. Both the transfer plasmid DNAs and the genomic DNAs of a baculovirus were introduced into Sf9 cells according to the protocol of Invitrogen, and recombinant virus-containing fractions appearing in a supernatant were recovered. The recovered fractions were selected by a plaque assay using a dry agar plate to obtain a recombinant virus. Sf9 cells (2×10$^6$ cells/25 cm$^2$ of flask) were infected with this virus, and cultivated at 27° C. for 5 days. Then, the cells in the flask were recovered by pipetting. After washing the cells with Grace's insect medium containing no serum and no additive, the cells were suspended in Hanks' balanced salt solution (HBSS) supplemented with 0.05% BSA. [$^3$H] TRH (du Pont) was added thereto to give a final concentration of 10 nM, and allowed to stand for 1 hour at room temperature to achieve binding. Further, in order to estimate the non-specific adsorption, a group to which 10 $\mu$M of non-labeled TRH was added was similarly prepared. The cells were recovered by centrifugation, and washed with Hanks' balanced salt solution (HBSS) to remove unbound [$^3$H] TRH. Then, the precipitate was dissolved in 0.2N NaOH and 1% SDS, and the amount of [$^3$H] TRH bound was measured by use of a liquid scintillation counter. As a control, Sf9 cells infected with no virus was used. For the Sf9 cells infected with the virus into which the human TRH receptor genes were introduced, the binding of [$^3$H] TRH was observed, and moreover, the addition of 1000-fold unlabeled TRH to [$^3$H] TRH antagonized the binding, whereby the expression of the human TRH receptor in the cells was confirmed [FIG. 8].

[EXAMPLE 4]

Expression of Human TRH Receptor Protein Using CHO dhfr$^-$ Strain

As an expression vector in CHO cells, pAKKO1.11 was used. pAKKO1.11 was constructed in the following manner.

A 1.4-kb DNA fragment containing an SRα' promoter and a poly(A) signal was obtained from pTB1417 described in Japanese Patent Unexamined Publication (Laid-open) No. 5-076385 by treatment with HindIII and ClaI. Further, a 4.5-kb DNA fragment containing a dihydrofolate reductase (dhfr) gene was obtained from pTB348 [K. Naruo et al., Biochem. Biophys. Res. Commun., 128, 257–264 (1985)] by treatment with ClaI and SalI. The ends of these DNA fragments were made flush by treatment with T4 polymerase, followed by binding by use of T4 ligase to construct pAKKO1.11 plasmid. Then, cloning sites according to the following synthetic DNAs (i) and (ii) were introduced into the SalI site, the sole cloning site of pAKKO1.11. As a result, a plasmid was constructed in which SalI, ClaI, SpeI and NheI sites were added downstream from the SRα' promoter as multi-cloning sites.

(i) 5'-GTCGACGAATTCATCGATACTAGTGCTAGC-3' (SEQ ID NO: 11 in the sequence listing)

(ii) 5'-TCGAGCTAGCACTAGTATCGATGAA-TTCGTCGAC-3' (SEQ ID NO: 12 in the sequence listing)

Figure 9:
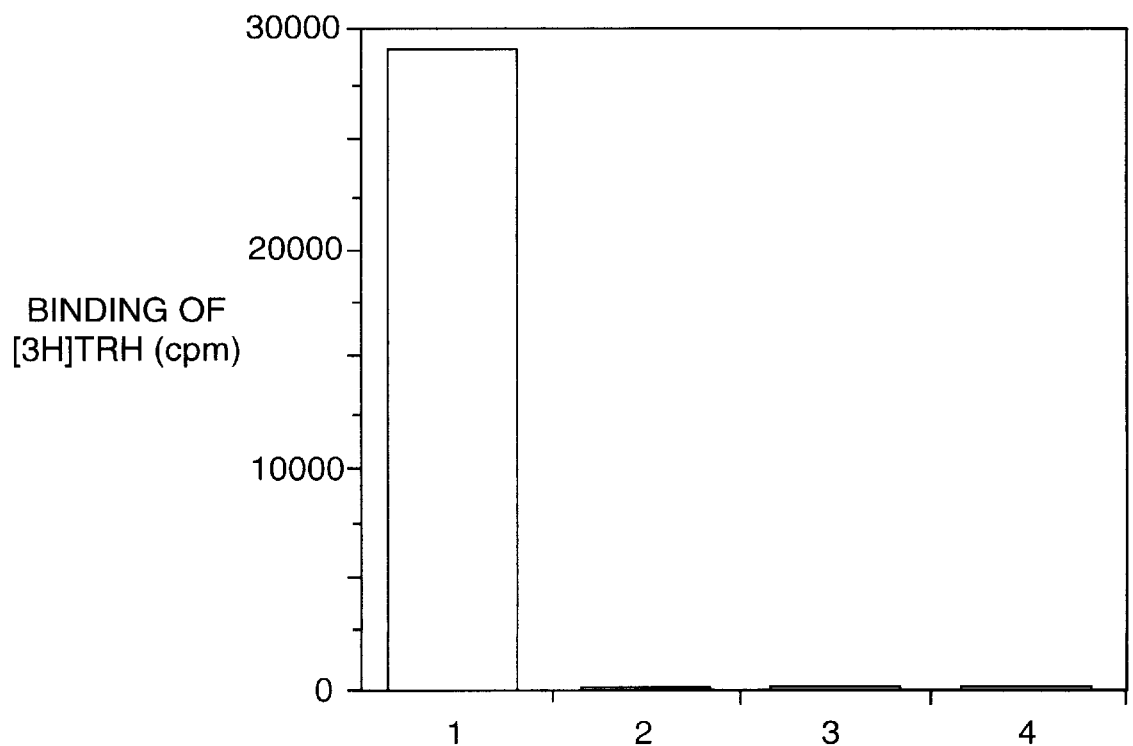
FIG. 9 shows the [$^3$H] TRH binding of a human TRH receptor protein expressed by use of CHOdhfr$^-$ cells. Columns 1 and 2 on the abscissa indicate CHOdhfr$^-$ cells into which human TRH receptor DNAs were introduced, and columns 3 and 4 indicate CHOdhfr⁻ cells as a control. 10 nM of [$^3$H] TRH was added to column 1, 10 nM of [$^3$H] TRH and 10 μM unlabeled TRH to column 2, 10 nM of [$^3$H] TRH to column 3, and 10 nM of [$^3$H] TRH and 10 μM unlabeled TRH to column 4. The numbers on the ordinate indicate the [$^3$H] TRH binding (cpm) of the respective cells.

This plasmid was cleaved with SalI and ClaI. The plasmid obtained in Example 3 in which the translation frame (open reading frame) of the human TRH receptor was constructed on pUC118 was cleaved with HindIII, and repaired with a Klenow fragment, followed by addition of an SalI linker. The resulting fragment was further cleaved with SmaI, and a fragment containing the translation frame (open reading frame) of the human TRH receptor and a ClaI linker were added thereto. This was cleaved with SalI and ClaI, and thereafter, the plasmid DNA previously cleaved with SalI and ClaI was bound thereto to complete an expression plasmid. This plasmid DNA was purified by cesium chloride equilibrium density gradient centrifugation, and partially introduced into the CHO dhfr⁻ cell line with a gene introduction kit (CellPhect, Pharmacia) by the calcium phosphate precipitation method. The original CHO dhfr⁻ cell line is impossible to grow in a medium not containing a nucleoside and a nucleotide, because of lack of dhfr phenotype. However, a transformant cell into which a plasmid having dhfr as a selected marker is introduced is growable in the medium mentioned above. Utilizing this fact, cells into which the human TRH receptor DNAs were introduced were selected. First, gene-introduced cell groups were subcultured at a low density to form colonies. A part thereof was separated for each colony to obtain uniform cell groups. Further, considering the grown cells to be groups containing transformant cells at a high rate, a binding experiment with radio-labeled TRH was conducted. First, $4 \times 10^5$ cells/well of the CHO dhfr⁻ cell line and the transformed cells into which a plasmid having dhfr as a selected marker and $8.0 \times 10^5$ cells/well of $GH_3$ cells (rat pituitary tumor cells expressing the rat TRH receptor protein) were subcultured to a 12-well tissue culture plate, and subjected to the binding experiment after 2 days. After removal of the medium, each cell was washed twice with 1 ml of Hanks' balanced salt solution (HBSS, GIBCO) supplemented with 0.05% BSA. Then, 495 $\mu$l of the Hanks' balanced salt solution and 5 $\mu$l of 1 $\mu$M [$^3$H] TRH were added to a final concentration of 10 $\mu$M. After standing for 1 hour at room temperature, the cells were further washed with three 1 ml portions of the Hanks' balanced salt solution. The cells were dissolved in 500 $\mu$l of 1% SDS and 0.2N NaOH, and the radioactivity contained therein was measured by use of liquid scintillator A. In order to know the non-specific binding, a group was also prepared to which non-labeled TRH was added to a final concentration of 10 $\mu$M in addition to [$^3$H] TRH, and a similar procedure was performed for this group. As a result, the non-specific binding was little detected to the binding of a ligand near 30,000 cpm in radioactivity, and no specific binding was detected at all in the CHO dhfr⁻ cell line into which no human TRH receptor DNA was introduced (FIG. 9).

[EXAMPLE 5]

Screening (1) of Compounds That can Antagonize the Binding of TRH Using CHO dhfr⁻ Cell line Transformed with Human TRH Receptor DNA To each well of a 12-well tissue culture plate (Sumitomo Bakelite) were subcultured $5 \times 10^5$ cells of transformant cells (CHO dhfr⁻ cell line), and the cells were cultivated in a $CO_2$ incubator maintained at a $CO_2$ concentration of 5% at 37° C. for 2 days or for 3 days. The cultivated cells were subjected to a binding experiment. The medium was removed from each well, and each cell was washed twice with 1 ml of Hanks' balanced salt solution (HBSS, GIBCO) supplemented with 0.05% BSA. Then, 490 $\mu$l of the Hanks' balanced salt solution, 5 $\mu$l of a test solution and 5 $\mu$l of 1 $\mu$M [$^3$H] TRH (du Pont/NEN, specific activity: 3072 GBq/mmol) were added, and stirred so as to disperse uniformly. After standing for 1 hour at room temperature, the reaction solution was removed, and the cells were washed three times with 1 ml of the Hanks' balanced salt solution. In order to know the non-specific binding, wells to which 10 $\mu$M non-labeled TRH was added were prepared, and a similar procedure was performed for these wells. The radio-labeled TRH bound to the TRH receptor expressed in the CHO dhfr⁻ cell line was recovered by dissolving the cells in the wells in 0.5 ml of 1% SDS and 0.2N NaOH. The recovered TRH was mixed with 4 ml of liquid scintillator A (Wako Pure Chemical Industries), and measured by use of a liquid scintillation counter (Beckmann). The antagonistic activity of respective test compounds was evaluated by calculating the amounts bound when the test compounds were added as percentage to that of the control, and comparing the values.

As the test compounds, 4 kinds of benzodiazepine compounds, midazolam, chlordiazepoxide, flunitrazepam and oxazepam (all are known compounds), were used to examine the antagonistic binding activity to the human TRH receptor. Each of the test compounds was diluted in three steps to final concentrations of 1 mM, 100 $\mu$M and 10 $\mu$M to examine it. Results thereof are shown in Table 1.

[TABLE 1]

| | Concentration | | |
|---|---|---|---|
| Name of Compound | 1 mM | 100 $\mu$M | 10 $\mu$M |
| Midazolam | 69.7 | 12.0 | 2.6 |
| Chlordiazepoxide | 46.8 | 7.1 | −2.2 |
| Oxazepam | 30.4 | 4.7 | 1.9 |
| Flunitrazepam | −13.7 | −4.0 | −0.5 |

The results shown in Table 1 revealed that the antagonistic activity increased in order of midazolam, chlordiazepoxide and oxazepam. Of the same benzodiazepine compounds, no antagonistic binding was observed at all for flunitrazepam.

These results show that the use of the screening methods of the present invention makes it possible to screen efficiently the compounds that can antagonize the binding of TRH to the human TRH receptor.

[EXAMPLE 6]

Screening (2) of Compounds That can antagonize the Binding of TRH Using CHO dhfr⁻ Cell Line Transformed with Human TRH Receptor DNA Using the same method as with Example 5, the antagonistic binding activity of some TRH analogous compounds to the human TRH receptor was examined. Results thereof are shown in Table 2.

[TABLE 2]

| Structural Formula | Antagonistic Rate (%) at Each Concentration (-log M) | | | | | | | | | |
|---|---|---|---|---|---|---|---|---|---|---|
| | 3 | 4 | 5 | 6 | 7 | 8 | 9 | 10 | 11 | 12 |
| TRH (pGlu His Pro NH$_2$) | | | 99.7 | 98.7 | 90.7 | 52.0 | 7.2 | 0.3 | 0.7 | 0 |
| 1 pGlu His | | -6.7 | -2.6 | | | | | | | |
| 2 Cyclo(His—Pro) His Pro-Diketopiperazine | | -1.1 | 0.6 | | | | | | | |
| 3 pGlu His Pro Gly Lys | | | 31.9 | -0.6 | | | | | | |
| 4 pGLU His Pro | | 40.8 | 11.8 | | | | | | | |
| 5 Blc His Pro NH$_2$ | 98.9 | 89.9 | 54.0 | 12.2 | —0.7 | -2.2 | -0.8 | -2.1 | | |
| 7 Blc His Pro | | 0.7 | -0.1 | | | | | | | |
| 8 Blc His Pro NHMe | 79.8 | 35.1 | 4.6 | 0.7 | 4.8 | 6.7 | 4.7 | 6.1 | | |
| 9 Blc His Pro NMBu | 99.4 | 95.8 | 72.8 | 33.8 | 7.6 | 4.9 | 6.4 | 5.3 | | |
| 10 Kpc His Pro NHBu | | | 99.6 | 97.5 | 83.5 | 38.0 | 4.4 | 5.4 | 6.7 | 3.9 |
| 11 Otc His Pro NHMe | 99.6 | 99.8 | 79.8 | 45.4 | 11.9 | 1.1 | 6.6 | 6.6 | | |
| 12 Otc His Pro NHPhEt | 99.6 | 97.0 | 78.1 | 37.9 | 10.3 | 2.4 | 7.8 | 6.4 | | |
| 13 Glu His Pro NH$_2$(*1) | | | 95.3 | 70.7 | 19.7 | 1.8 | 1.0 | 2.0 | | |
| 14 pGlu Phe Pro NH$_2$ | | 96.2 | 74.2 | | | | | | | |
| 15 pGlu NVal Pro NH$_2$ | | 78.6 | 33.4 | | | | | | | |
| 16 pGlu 3-Me-His Pro NH$_2$ | | | 97.9 | 99.8 | 99.1 | 85.0 | 20.0 | -4.4 | -7.1 | -6.5 |
| 17 pGlu Glu Pro NH$_2$ | | 4.7 | -2.9 | | | | | | | |
| 18 pGlu His 3,4-dihydro-Pro NH$_2$(*1) | | | 99.7 | 98.3 | 84.6 | 39.1 | 7.0 | 2.2 | | |
| 19 OOC His TC NH$_2$ | | | 99.1 | 93.3 | 62.6 | 14.3 | 0.4 | 0.8 | 0.7 | 1.3 |
| TRH (*1) | | | 99.7 | 97.8 | 83.9 | 39.8 | 4.2 | -0.7 | | |

In Table 2, the degree of a reduction in the binding of [$^3$H] TRH in the case where the TRH analogous compound having respective concentrations was added to the total binding of [$^3$H] TRH in the case where no TRH analogous compound existed was indicated as percentage. The specific activity of [$^3$H] TRH used in the experiment was 83.04 Ci/mmol, and this was added to give a concentration of 10 nM in the reaction solution. For the compounds indicated by (*1) in the table, the specific activity of [$^3$H] TRH was 45 Ci/mmol, and this was added to give a concentration of 18.3 nM in the reaction solution.

The results shown in Table 2 revealed that the TRH analogous compounds used in the experiment antagonize the binding of TRH to the human receptor.

[EXAMPLE 7]

Figure 10:
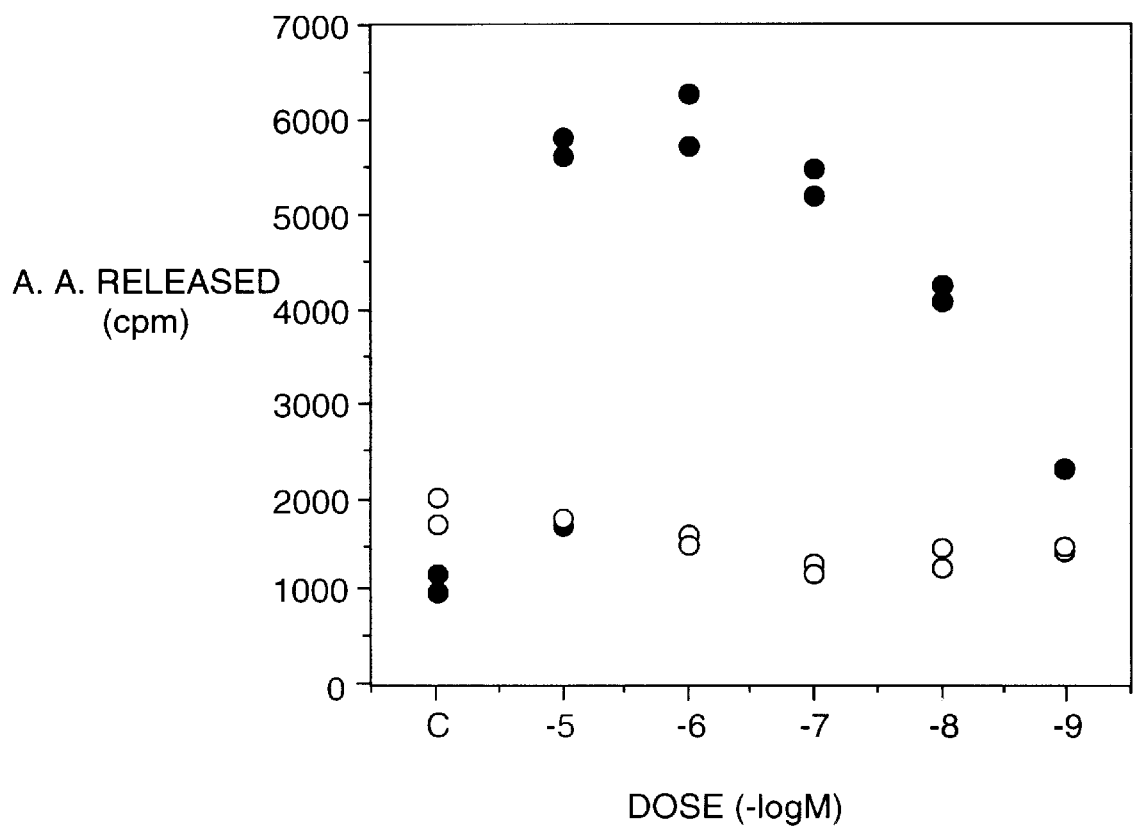
FIG. 10 shows the amount of arachidonic acid released from CHO cells into which human TRH receptor DNAs were introduced (O) and CHOdhfr⁻ cells as a control (●) when TRH was added. The numbers on the abscissa indicate the concentration of TRH, and the numbers on the ordinate indicate the radioactivity of arachidonic acid released.
Figure 11:
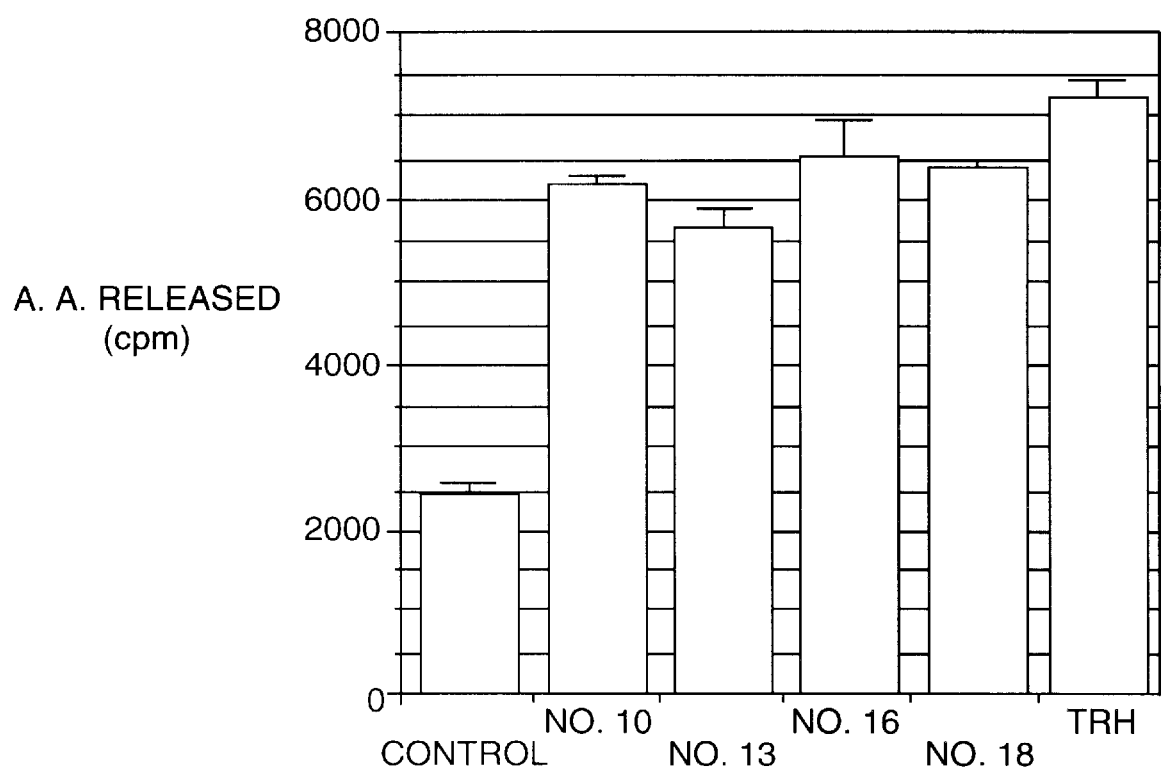
FIG. 11 shows the results of the releasing activity of arachidonic acid evaluated by use of CHO cells into which human TRH receptor DNAs were introduced. The compound Nos. correspond to those of Table 2. The numbers on the abscissa indicate the compound Nos., and the numbers on the ordinate indicate the radioactivity of arachidonic acid released.
Figure 12A:
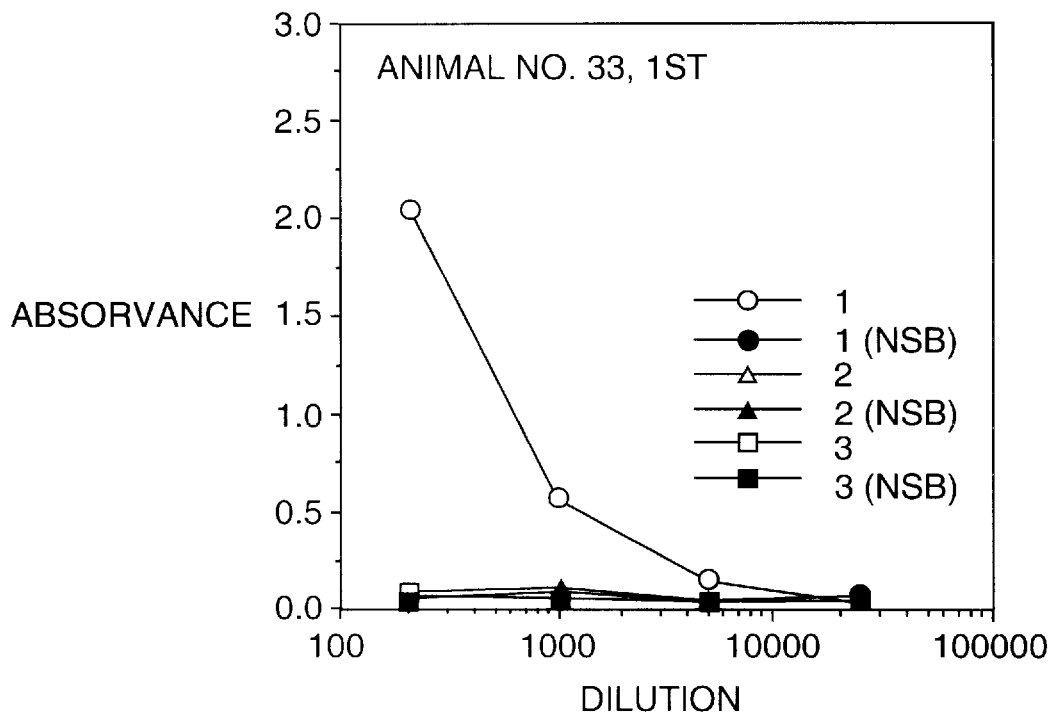
FIG. 12 shows the antibody titers. (A) shows antibody titers in the first blood collection of the rabbit No. 33. B, C and D show antibody titers in the 2nd blood colletion of the rabbit No.33, in the first blood collection of the rabbit No. 34, and in the 2nd blood colletion of the rabbit No.34. In the Figure, 1, 2 and 3 show the results using the synthesized antigen peptides, and NSB show the results of non-specific adsorption to the plates.
Figure 12B:
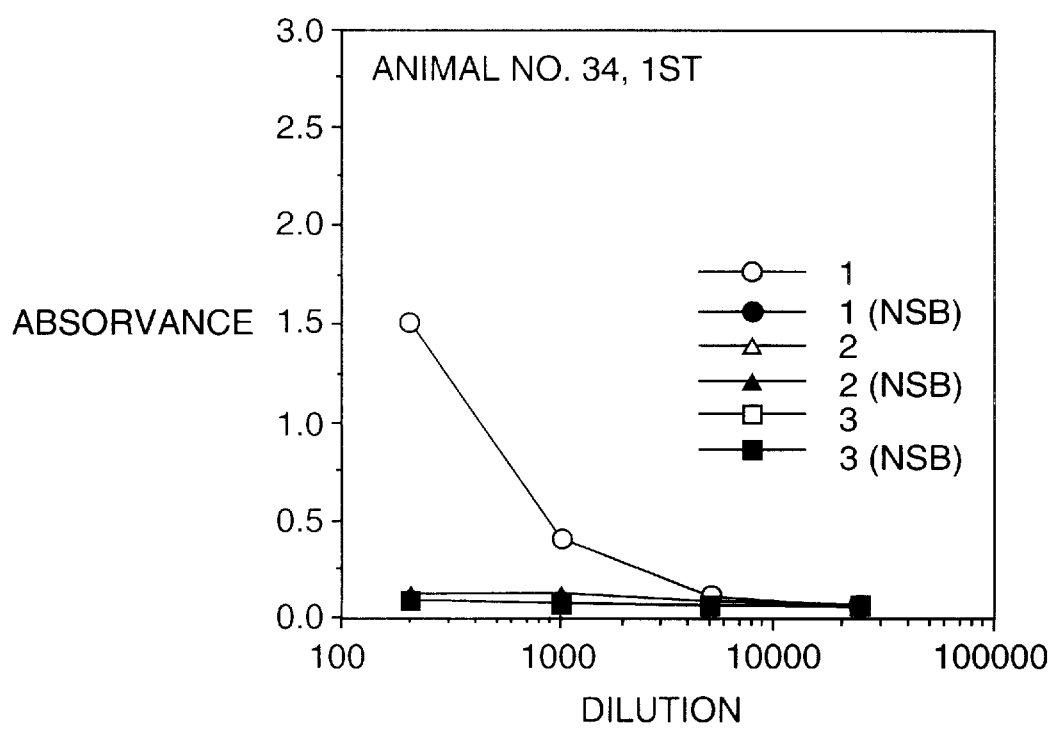
Figure 12C:
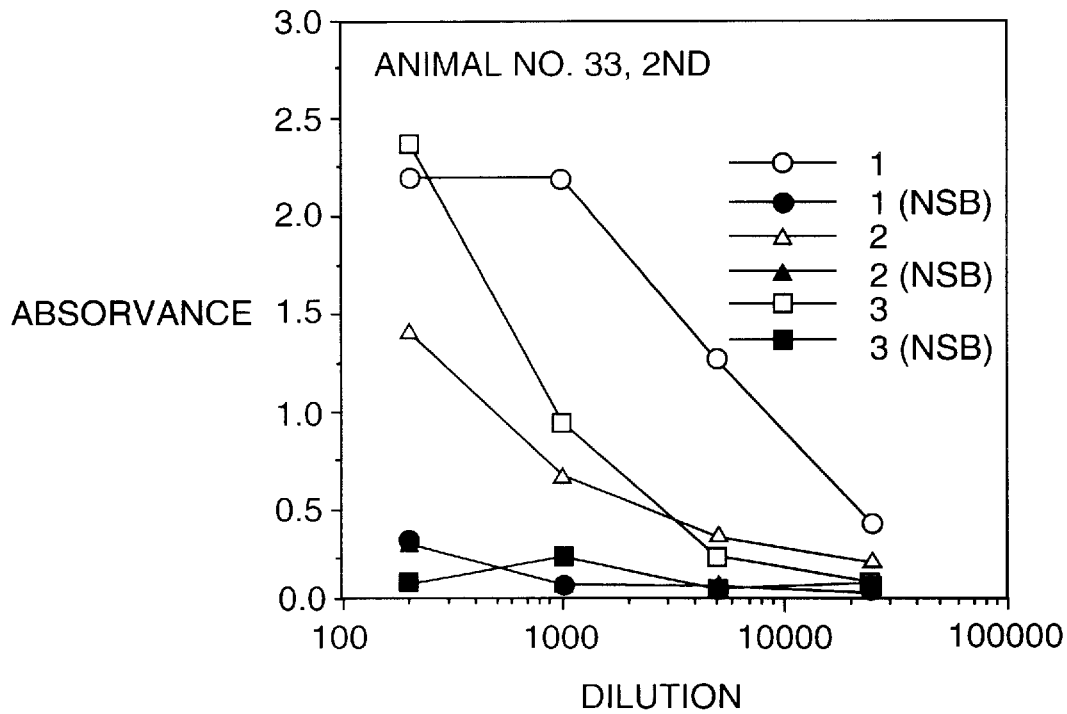
Figure 12D:
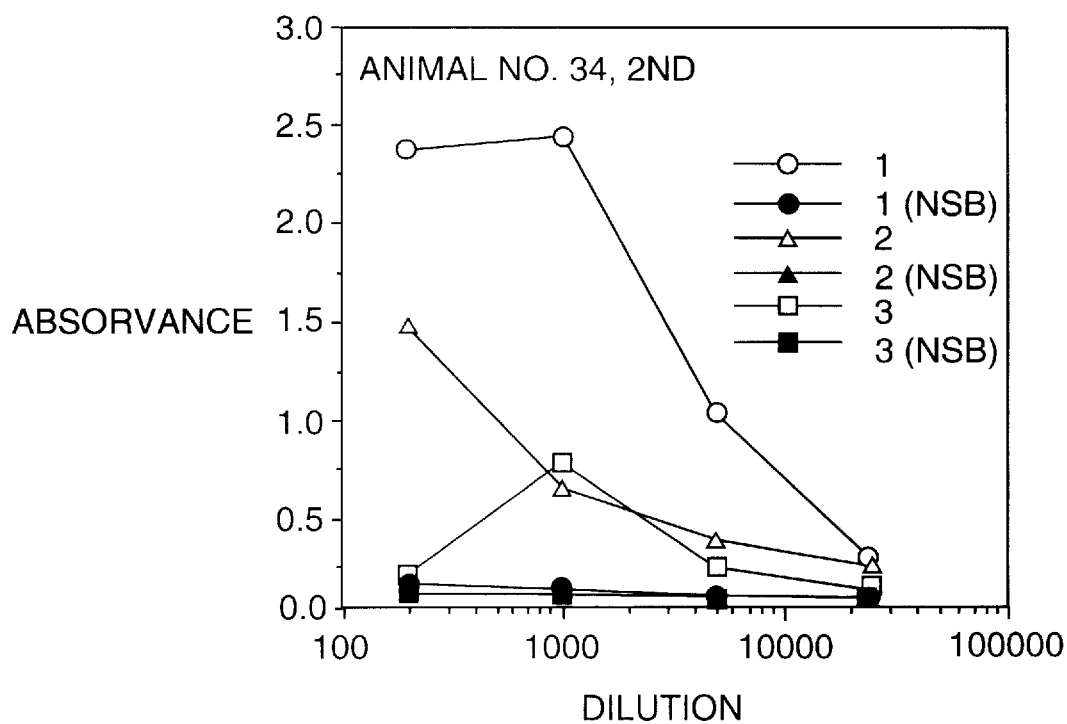

Screening of Human TRH Receptor Agonist and Antagonist Based on Release of Arachidonic Acid CHO cells into which the human TRH receptor DNAs obtained in Example 4 were subcultured at a density of 1.0×10$^6$ cells/well to a 12-well tissue culture plate (Sumitomo Bakelite) and cultivated for 24 hours. The medium was removed and replaced by a fresh medium. Then, [$^3$H] TRH-labeled arachidonic acid (du Pont/NEN, specific activity: 60–100 Ci/mmol) was added to give a concentration of 0.5 μCi/well. After addition of arachidonic acid, the cells were further cultivated for 24 hours, and washed three times with Hanks' balanced salt solution (HBSS) supplemented with 0.05% BSA. Thereafter, 495 μl/well of HBSS supplemented with 0.05% BSA was added thereto. Then, 5 μl of a test solution was added thereto, and incubation was conducted for 30 minutes at room temperature to release arachidonic acid in the medium. HBSS (400 μl) of the supernatant was recovered, and mixed with liquid scintillator A (Wako Pure Chemical Industries). The amount of released [$^3$H]-labeled arachidonic acid was measured by use of a liquid scintillation counter (Beckmann). The CHO cells into which the human TRH receptor DNAs were introduced reacted with TRH to increase the amount of arachidonic acid released depending upon the concentration, compared with the control (HBSS alone). For the CHO dhfr$^-$ cells, no change was observed (FIG. 10).

Further, in the receptor binding experiment of Example 6, the releasing activity of arachidonic acid was measured using 4 kinds of compounds strongly that can antagonize the binding of [$^3$H] TRH (compound Nos. 10, 13, 16 and 18). As a result, all compounds promoted release of arachidonic acid at a concentration of 10 μM similarly to TRH, which revealed that they had agonist activity to the human TRH receptor.

These results shows that TRH receptor agonists and antagonists can be evaluated by the screening methods of the present invention

[EXAMPLE 8]

Preparation of Anti-human TRH receptor Antibody

Peptides which have 1st to 20th, 232th to 251th and 384th to 398th amino acid sequences of SEQ ID NO:1 for human TRH receptor, respectively, were synthesized as Multiple Antigen Peptide: MAP according to Fmoc method.

A mixture of the peptides was made into an antigen peptide solution, and two rabbits were immunized with them. In order to enhance the immunization reaction, Freund's complete adjuvant was used for only the 1st immunization and Freund's incomplete adjuvants were used for the second or later immunizations. After the 4th and 6th subcutaneous immunizations, blood was tentatively collected and antibody titers were assayed on each peptide. The titers were assayed as amounts of the antibodies in serum diluted by 200, 1000, 5000 and 25000 times respectively which were bound to a 96-dish ELISA plate coated with 50 μg/ml of the antigen peptides. The detections thereof were conducted by an HRP (horse radish peroxydase)-labeled antibody. ELISA was conducted according to a standard method, in order of an antigen peptide, a blocking agent (H-BSA), collected and diluted blood and HRP-labeled antibody, incubation thereof was conducted in the well at 37° C. for 1 hour, respectively. Then three washings with Tween 20-PBS respectively were conducted. Staining with 0.025M citric acid-0.05M phosphate buffer containing 0.4 mg/ml of o-phenylenediamine supplemented with 0.2 μl/ml of aqueous hydrogenperoxide was conducted under mixing for 30 minutes and 2M sulfuric acid equivalent amount of the staining solution was added to terminate the staining. Activities of HRP bound were assayed at 492 nm absorption and production of the antibodies to each peptide were detected (A to D in FIG. 12).

[EXAMPLE 9]

Screening of Human TRH Receptor Agonist and Antagonist Using c-fos Promoter

Figure 13:
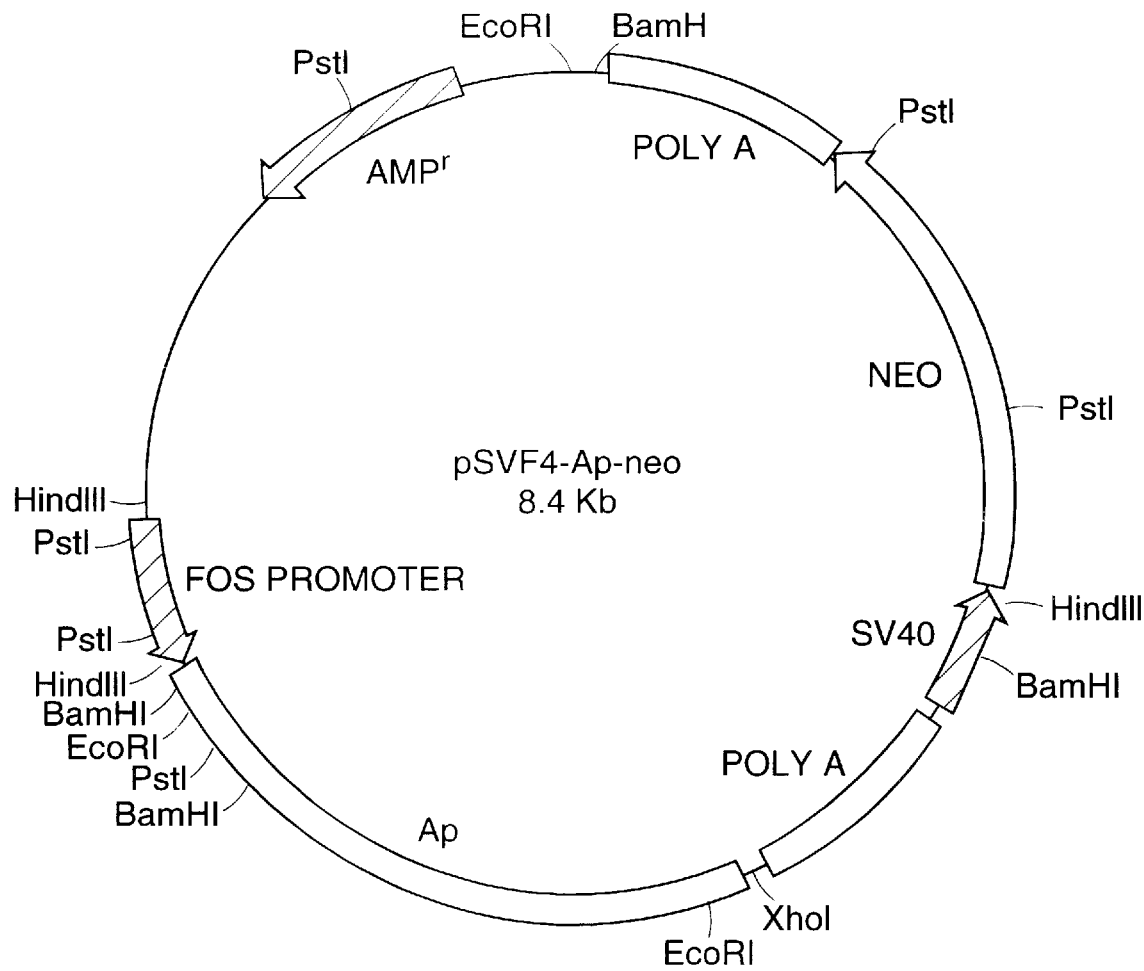
FIG. 13 shows a construction of a vector of pSVF4-Ap-neo. An alkaline phosphatase gene was linked downstream from a c-fos promoter. A neomycin resistant gene was inserted for a selection of an agent.

An insertion of a secretive alkaline phosphatase gene linked to a c-fos promoter into a TRH receptor expression cell was conducted as follows:

$5 \times 10^5$ TRH receptor expression CHO cells were inoculated onto a 10 cm plate and they were cultivated for 24 hours in Ham's F12 medium (Lifetech Oriental) equipped with 10% fetal bovine serum. 3 μg of a vector (pSVP4-Ap-neo, FIG. 13) which was introduced by a secretive alkaline phosphatase gene downstream from the c-fos promoter was introduced into the CHO cells using a gene introducing kit (Cell Phect, Pharmacia) by calcium phosphate method. The cells introduced by the vector were cloned in the above-described medium equipped with 500 μg/ml of G418. 39 clones were isolated and clones which have high TRH responsiveness were further selected.

Figure 14:
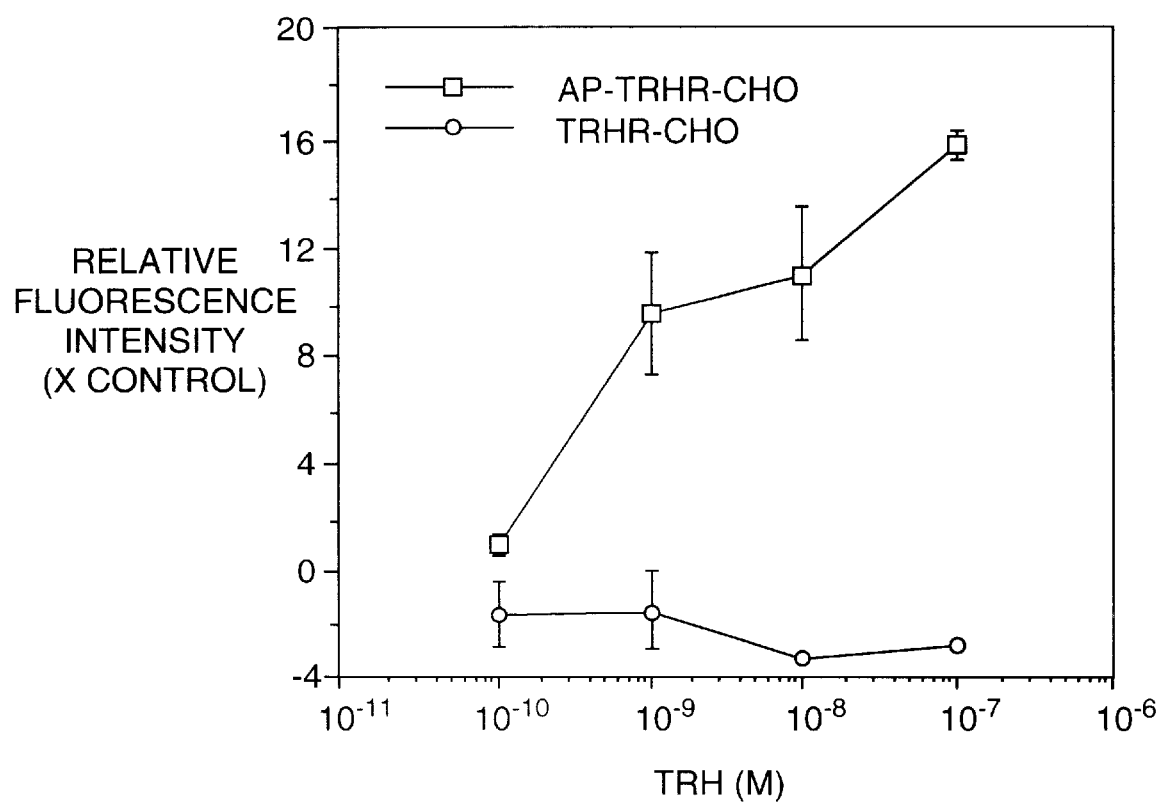
FIG. 14 is a graph which shows an assay of TRH receptor signal transduction system using alkaline phosphatase activity as an indicator. The fluorescence activity intensity by action of TRH was shown as the intensity is 1 when a concentration of TRH in the TRH receptor expression cells which was inserted by an alkaline phosphatase gene is zero (0). AP-TRHR-CHO is a cell which was inserted by an alkaline phosphatase gene and TRHR-CHO is a CHO cell which expresses a TRH receptor.

Cell stimulating activity through a TRH receptor using activation of c-fos promoter as an indicator was assayed as follows:

Each $5 \times 10^4$ of the above-described transformants were inoculated onto 96 hole plates for tissue cultivation (Corning) and they were cultivated for a night. The medium was thrown away next day, each plate was washed with 200 μl of PBS(−) and the each medium was replaced with 120 μl of DMEM (without phenol red, ICN Biomedicals Inc.) to be cultivated at 37° C. for 6 hours. The medium was changed with 100 μl of TRH or of DMEM (with no phenol red) containing test compounds and cultivation was conducted for a night. 20 μl of the supernatant was taken onto a 96 hole fluoro plate (MicroFLUOR, DYNATECH), 100 μl of a reaction buffer [2.5 μg/ml, 4-Metylumbelliferylphosphoric Acid (Wako Pure Chemical); 10% diethanolamine(Wako Pure Chemical); 1 mM $MgCl_2$ (pH 9.8)] was added thereto and the mixture was reacted at 37° C. for 6 hours. The plate was assayed by a fluorescence plate reader (Fluoroskan II, Titertek) at 365 nm of excitation and 450 nm of luminescence. As a result, as shown in FIG. 14, in the human TRH receptor expression CHO cells, alkaline phosphatase secrets into the supernatant depending on the concentration of TRH added. The result shows that this method can screen a human TRH receptor agonist or antagonist.

The human TRH receptor proteins and the DNAs coding for said proteins of the present invention can be used for (i) acquisition of antibodies and antisera, (ii) construction of expression systems of recombinant receptor proteins, (iii) development of receptor binding assay systems and cell stimulation assay systems using said expression systems and screening of potential compounds for drugs, (iv) execution of drug design based on the comparison of ligands and receptors which are structurally similar to each other, (v) preparation of probes and PCR primers in gene diagnosis, (vi) detection of human TRH or human TRH receptors in vivo and (vii) gene therapy. In particular, the information hitherto obtained suggests that human TRH is deeply related to the functions of the central nerve system, etc. Accordingly, elucidation of the structure and properties of the human TRH receptors contributes to the development of unique drugs acting on these systems.

What is claimed is:

1. A method of screening for a compound that inhibits binding of TRH to a human TRH receptor, or a salt thereof, comprising contacting a TRH receptor protein obtained from a cell transformed with an expression vector containing a DNA encoding a TRH receptor having the amino acid sequence of SEQ ID NO: 1, or a sufficient portion thereof to bind TRH, or the salt thereof, with the compound to be screened and TRH, and comparing binding between TRH and the TRH receptor in the absence and presence of the compound, wherein less binding between the TRH and the receptor in the presence of the compound than in the absence of the compound is indicative of the compound inhibiting binding between TRH and the receptor.

2. The method of claim 1, wherein the receptor protein is encoded by the nucleotide sequence of SEQ ID NO: 2.

3. A method of screening for a compound that inhibits binding of TRH to a human TRH receptor, or a salt thereof, comprising comparing the amount of a labeled ligand bound to a receptor protein free of human tissue and having the amino acid sequence of SEQ ID NO:1, or a sufficient portion thereof to bind TRH, or the salt thereof by steps (a) and (b);

(a) contacting the labeled ligand with the receptor protein having the amino acid sequence of SEQ ID NO:1, or a sufficient portion thereof to bind TRH, or a salt thereof, (b) contacting the labeled ligand and a test compound with the receptor protein having the amino acid sequence of SEQ ID NO:1, or a sufficient portion thereof to bind TRH, or the salt thereof, wherein a decrease in labeled ligand binding in step (b) indicates that the compound inhibits binding of TRH to a human TRH receptor, or a salt thereof, further wherein said receptor is from a cell transformed with an expression vector containing a DNA encoding the amino acid sequences of SEQ ID NO:1, or a sufficient portion thereof to bind TRH.

4. The method as claimed in claim 3, wherein
the contacting in (a) is with a cell which contains the receptor protein having the amino acid sequence of SEQ ID NO:1, or a sufficient portion thereof to bind TRH, or the salt thereof and the contacting in (b) is with a cell which contains the receptor protein having the amino acid sequence of SEQ ID NO:1, or a sufficient portion thereof to bind TRH, or the salt thereof.

5. The method as claimed in claim 3, wherein
the contacting in (a) is with a membrane fraction of a cell containing the receptor protein having the amino acid sequence of SEQ ID NO:1, or a sufficient portion thereof to bind TRH, and the contacting in (b) is with the membrane fraction of the cell containing the receptor protein having the amino acid sequence of SEQ ID NO:1, or a sufficient portion thereof to bind TRH.

6. A method of screening for a compound that inhibits binding of TRH to a human TRH receptor, or a salt thereof, comprising comparing the amounts of a labeled ligand bound to a receptor protein free of human tissue having the amino acid sequence of SEQ ID NO:1, or a sufficient portion thereof to bind TRH, or the salt thereof in steps (a) and (b);
  (a) contacting the labeled ligand with the TRH receptor protein which is expressed on a cell membrane, said cell membrane obtained from a cell transformed with a DNA encoding the amino acid sequence of SEQ ID NO:1, or a sufficient portion thereof to bind TRH,
  (b) contacting the labeled ligand and a test compound with the TRH receptor protein which is expressed on a cell membrane, said cell membrane obtained from a cell transformed with a DNA encoding the amino acid sequence of SEQ ID NO:1, or a sufficient portion thereof to bind TRH, wherein a decrease in labeled ligand binding in step (b) indicating that the compound inhibits binding of TRH to a human TRH receptor, or a salt thereof.

7. The method as claimed in claim 6, wherein said labeled ligand is [$^3$H]TRH.

8. A method of screening for a TRH receptor agonist or antagonist comprising measuring cell stimulating activities through a TRH receptor determined from the following steps (a) and (b);
  (a) contacting a test compound with a cell transformed with a DNA encoding the receptor protein having the amino acid sequence of SEQ ID NO:1, or a sufficient portion thereof to bind TRH, referred to as a test screen, and comparing the results to a control wherein the cell does not comprise the receptor, wherein said compound having cell stimulating activity in the test screen but not the control indicates that said compound is a TRH receptor agonist,
  (b) contacting a TRH receptor-activating compound and a test compound with a cell transformed with a DNA encoding the receptor protein having the amino acid sequence of SEQ ID NO:1, or a sufficient portion thereof to bind TRH, referred to as a test screen, and comparing the results to a control wherein the cell does not comprise the receptor, wherein a decrease in cell stimulating activity by the TRH receptor-activating compound in the test screen but not the control indicates that the compound is a TRH receptor antagonist, and further wherein the cell stimulating activities are selected from the group consisting of mobilization of calcium in the cells, hyper metabolism of inositol phosphate, arachidonic acid releasing activity, acetylcholine releasing activity, activation of adenylate cyclase and activation of c-fos.

9. A method of screening for a TRH receptor agonist or antagonist comprising measuring cell stimulating activities through a TRH receptor in steps of (a) and (b);
  (a) contacting a test compound with the TRH receptor protein which is expressed on a cell membrane, said membrane obtained from a cell transformed with a DNA encoding the amino acid sequence of SEQ ID NO:1, or a sufficient portion thereof to bind TRH, referred to as a test screen, and comparing the results to a control wherein the cell does not express the DNA, wherein said compound having cell stimulating activity in the test screen but not the control indicates that said compound is a TRH receptor agonist,
  (b) contacting a TRH receptor-activating compound and a test compound with the TRH receptor protein which is expressed on a cell membrane, said membrane obtained from a cell transformed with a DNA encoding the amino acid sequence of SEQ ID NO:1, or a sufficient portion thereof to bind TRH, referred to as a test screen, and comparing the results to a control wherein the cell does not comprise the receptor, wherein a decrease in cell stimulating activity by the TRH receptor-activating compound in the test screen of step (b) but not the control indicates that the compound is a TRH receptor antagonist, and further wherein the cell stimulating activities are selected from the group consisting of mobilization of calcium in the cells, hyper metabolism of inositol phosphate, arachidonic acid releasing activity, acetylcholine, activation of adenylate cyclase and activation of c-fos.

10. The method as claimed in claim 8 or 9, wherein said TRH receptor-activating compound is TRH.

11. The method of claim 8 or 9, wherein the cell stimulating activity is arachidonic acid releasing activity or activation of c-fos.

12. The method of claim 4, 5, 6, 8 or 9, wherein the cell is monkey cell COS-7, Vero, Chinese hamster cell (CHO), mouse L-cell, mouse myeloma cell or human FL cell.

13. A method of screening for a compound that inhibits binding of TRH to a TRH receptor, or a salt thereof, comprising contacting a TRH receptor protein encoded by the nucleotide sequence of SEQ ID NO:2 with the compound to be screened and TRH and determining whether the compound inhibits the binding of TRH to the TRH receptor, wherein said receptor is from a cell transformed with an expression vector containing the nucleotide sequence of SEQ ID NO:2.

14. A method of screening for a compound that inhibits the binding of TRH to a human TRH receptor, or a salt thereof, comprising comparing the amount of a labeled ligand bound to the receptor protein having the amino acid sequence of SEQ ID NO:1, or a sufficient portion thereof to bind TRH, or the salt thereof determined from the following steps (a) and (b);
  (a) contacting the labeled ligand with a cell which contains the receptor protein having the amino acid sequence of SEQ ID NO:1, or a sufficient portion thereof to bind TRH, or the salt thereof,
  (b) contacting the labeled ligand and a test compound with a cell which contains the receptor protein having the amino acid sequence of SEQ ID NO:1, or a sufficient portion thereof to bind TRH, or the salt thereof, wherein the cell is transformed with a DNA encoding the amino acid sequence of SEQ ID NO:1, or a sufficient portion thereof which bind TRH, and the cell is selected from the group consisting of monkey cell COS-7, Vero, Chinese hamster cell (CHO), mouse L-cell, mouse myeloma cell and human FL cell, and wherein a decrease in labeled ligand binding compared with step (a) indicates that the compound inhibits binding of TRH to a human TRH receptor, or a salt thereof.

15. A method of screening for a compound that inhibits the binding of TRH to a human TRH receptor, or a salt thereof, comprising comparing the amount of a labeled ligand bound to the receptor protein having the amino acid sequence of SEQ ID NO:1, or a sufficient portion thereof to bind TRH, or the salt thereof by steps (a) and (b);

(a) contacting said labeled ligand with a membrane fraction of a cell transformed with a DNA encoding the receptor protein having the amino acid sequence of SEQ ID NO:1, or a sufficient portion thereof to bind TRH, (b) contacting said ligand and said test compound with the membrane fraction of the cell transformed with the DNA encoding the receptor protein having the amino acid sequence of SEQ ID NO:1, or a sufficient portion thereof to bind TRH, wherein the cell is selected from the group consisting of monkey cell COS-7, Vero, Chinese hamster cell (CHO), mouse L-cell, mouse myeloma cell and human FL cell, and wherein a decrease in labeled ligand binding in step (b) indicates that the compound inhibits binding of TRH to a human TRH receptor, or a salt thereof.

16. A method of screening for a compound that inhibits binding of TRH to a human TRH receptor, or a salt thereof, comprising comparing the amounts of a labeled ligand bound to a receptor protein having the amino acid sequence of SEQ ID NO:1, or a sufficient portion thereof to bind TRH, or the salt thereof in steps (a) and (b);

(a) contacting the labeled ligand with the TRH receptor protein which is expressed on a cell membrane, said cell membrane obtained from a cell transformed with a DNA encoding the amino acid sequence of SEQ ID NO:1, or a sufficient portion thereof to bind TRH, (b) contacting the labeled ligand and a test compound with the TRH receptor protein which is expressed on a cell membrane, said cell membrane obtained from a cell transformed with a DNA encoding the amino acid sequence of SEQ ID NO:1, or a sufficient portion thereof to bind TRH, wherein the cell is selected from the group consisting of monkey cell COS-7, Vero, Chinese hamster cell (CHO), mouse L-cell, mouse myeloma cell and human FL cell, and wherein a decrease in labeled ligand binding in step (b) indicates that the compound inhibits binding of TRH to a human TRH receptor, or a salt thereof.

17. A method of screening for a compound that is a TRH receptor agonist or antagonist comprising measuring cell stimulating activities through a TRH receptor determined from the following steps (a) and (b);

(a) contacting a test compound with a cell transformed with a DNA encoding the receptor protein having the amino acid sequence of SEQ ID NO:1, or a sufficient portion thereof to bind TRH, referred to as a test screen, and comparing the results to a control wherein the cell does not comprise the receptor, wherein said compound having cell stimulating activity in the test screen but not the control indicates that said compound is a TRH receptor agonist, (b) contacting a TRH receptor-activating compound and the test compound with a cell transformed with a DNA encoding the receptor protein having the amino acid sequence of SEQ ID NO:1, or a sufficient portion thereof to bind TRH, referred to as a test screen, and comparing the results to a control wherein the cell does not comprise the receptor, wherein a decrease in cell stimulating activity by the TRH receptor-activating compound in the test screen but not the control indicates that the compound is a TRH receptor antagonist, and further wherein the cell is selected from the group consisting of monkey cell COS-7, Vero, Chinese hamster cell (CHO), mouse L-cell, mouse myeloma cell and human FL cell.

18. A method of screening for a compound that is a TRH receptor agonist or antagonist comprising measuring cell stimulating activities through a TRH receptor determined from the following steps (a) and (b);

(a) contacting a test compound with a TRH receptor protein which is expressed on a cell membrane, said cell membrane obtained from a cell transformed with a DNA encoding the amino acid sequence of SEQ ID NO:1, or a sufficient portion thereof to bind TRH, referred to as a test screen, and comparing the results to a control wherein the cell membrane does not comprise the receptor, wherein said compound having cell stimulating activity in the test screen but not the control indicates that said compound is a TRH receptor agonist, (b) contacting a TRH receptor-activating compound and the test compound with the TRH receptor protein which is expressed on a cell membrane, said cell membrane obtained from a cell transformed with a DNA encoding the amino acid sequence of SEQ ID NO:1, or a sufficient portion thereof to bind TRH, referred to as a test screen, and comparing the results to a control wherein the cell membrane does not comprise the receptor, wherein a decrease in cell stimulating activity by the TRH receptor-activating compound in the test screen but not the control indicates that the compound is a TRH receptor antagonist, and further wherein the cell is selected from the group consisting of monkey cell COS-7, Vero, Chinese hamster cell (CHO), mouse L-cell, mouse myeloma cell and human FL cell.

19. A method of screening for a compound that is evaluated as TRH receptor agonist or antagonist that inhibits binding of TRH to a human TRH receptor, or a salt thereof, comprising:

(i) identifying a compound that inhibits binding of TRH to a human TRH receptor, or a salt thereof comprising comparing the amounts of a labeled ligand bound to a receptor protein free of human tissue and having the amino acid sequence of SEQ ID NO:1, or a sufficient portion thereof to bind TRH, or the salt thereof by steps (a) and (b);

(a) contacting the labeled ligand with the receptor protein having the amino acid sequence of SEQ ID NO:1, or a sufficient portion thereof to bind TRH, or the salt thereof, (b) contacting the labeled ligand and a test compound with the receptor protein having the amino acid sequence of SEQ ID NO:1, or a sufficient protein thereof to bind TRH, or the salt thereof, wherein a decrease in labeled ligand binding in step (b) indicates that the compound inhibits binding or TRH to a human TRH receptor, or a salt thereof, and (ii) determining whether said compound which inhibits binding of TRH to a human TRH receptor, or a salt thereof, is a TRH receptor agonist or TRH receptor antagonist by measuring cell stimulating activities through a TRH receptor comprising contacting said compound with a cell transformed with a DNA encoding the receptor protein having the amino acid sequence of SEQ ID NO:1, or a sufficient portion thereof to bind TRH, referred to as a test screen, and comparing the results to a control wherein the cell does not comprise the receptor, wherein said compound having cell stimulating activity in the test screen but not the control indicates that said compound is a TRH receptor agonist, and said compound having no cell stimulating activity in the test screen and the control indicates that said compound is a TRH receptor antagonist, wherein the cell stimulating activities are selected from the group consisting of mobilization of calcium in the cells, hyper metabolism of inositol phosphate, arachidonic acid releasing activity, acetylcholine releasing activity, activation of adenylate cyclase and activation of c-fos.

* * * * *